United States Patent
Maw et al.

(10) Patent No.: US 6,200,978 B1
(45) Date of Patent: Mar. 13, 2001

(54) COMPOUNDS AS DELTA OPIOID AGONISTS

(75) Inventors: Graham Nigel Maw; Donald Stuart Middleton, both of Sandwich (GB)

(73) Assignee: Pfizer Inc., New York, NY (US)

( * ) Notice: Subject to any disclaimer, the term of this patent is extended or adjusted under 35 U.S.C. 154(b) by 0 days.

(21) Appl. No.: 09/261,540

(22) Filed: Mar. 3, 1999

(30) Foreign Application Priority Data

Mar. 5, 1998 (GB) .................................................. 9804734

(51) Int. Cl.[7] .................. A61K 31/496; A61K 31/4985; C07D 403/10; C07D 413/10; C07D 417/10

(52) U.S. Cl. ..................... 514/254.05; 544/359; 544/365; 544/366; 544/367; 544/369; 544/236; 514/249; 514/254.03

(58) Field of Search ..................... 544/365, 366, 544/367, 369, 359, 236; 514/249, 254.03, 254.05

(56) References Cited

FOREIGN PATENT DOCUMENTS

| 0133323 | * | 2/1985 | (EP) . |
|---|---|---|---|
| WO9315062 | * | 8/1993 | (WO) . |
| WO9504051 | * | 2/1995 | (WO) . |
| WO9723466 | * | 7/1997 | (WO) . |
| WO9723467 | * | 7/1997 | (WO) . |
| WO9852929 | * | 11/1998 | (WO) . |

\* cited by examiner

*Primary Examiner*—Laura L. Stockton
(74) *Attorney, Agent, or Firm*—Peter C. Richardson; Gregg C. Benson; A. Dean Olson

(57) ABSTRACT

Compounds of the formula (I)—shown below—are described.

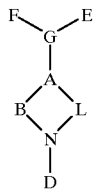

(I)

The compounds are useful in the manufacture of a pharmaceutical composition for preventing or treating inflammatory diseases such as arthritis, psoriasis, asthma, or inflammatory bowel disease, disorders of respiratory function, gastrointestinal disorders such as functional bowel disease, functional GI disorders such as irritable bowel syndrome, functional diarrhoea, functional distension, functional pain, non-ulcerogenic dyspepsia or others associated with disorders of motility or secretion, urogenital tract disorders such as incontinence, as analgesics for treating pain including non-somatic pain, or as immunosuppressants to prevent rejection in organ transplant and skin graft.

16 Claims, No Drawings

COMPOUNDS AS DELTA OPIOID AGONISTS

This application claims priority from U.K. application serial no. 9804734.3 which was filed on Mar. 5, 1998.

The present invention relates to compounds, including inter alia pharmaceutical compositions comprising the same and methods for making the same.

In particular, the present invention relates to compounds that are capable of treating gastrointestinal disorders such as irritable bowel syndrome and diarrhoea, urinary urge incontinence, and pain.

More particularly, this invention relates to cyclic compounds and compositions comprising the same—as well as their preparation—and their use as selective agonists for the delta (δ) receptor.

In particular, the present invention provides compounds that are suitable for use as δ opioid agonists.

Agonists and antagonists are agents that recognise and bind to receptors thereby affecting biochemical and/or physiological pathways. Agonists inhibit or suppress neurotransmitter outputs in tissues containing receptors—e.g. they can inhibit pain responses—or they can affect other output-related phenomena. Antagonists also bind to receptors but they do not inhibit neurotransmitter outputs. Thus, antagonists are capable of binding to the receptor sites and thereby block the binding of agonist species which are selective for the same species.

At least four subtypes of opioid receptors—namely δ, mu (μ) and kappa (κ)—are described and documented in the scientific literature. At least the δ, μ and κ receptors are present in the central and peripheral nervous systems of many species including man. A brief introduction to opioid receptors may also be found in WO 95/04051, WO 97/23467, WO 93/15062, and WO 97/23466.

For example, it is known that μ receptors mediate analgesia, respiratory depression and inhibition of gastrointestinal transit.

According to WO 95/04051, the existence of the opioid δ receptor is a fairly recent discovery. δ receptors mediate analgesia, but do not appear to inhibit intestinal transit as do the μ receptors. Activation of δ receptors is known to produce antinociception in rodents and can induce analgesia in man, in addition to influencing motility of the gastrointestinal tract [see Burks, T.F. (1995) in "The pharmacology of opioid peptides", Tseng L. F. ed. Harwood Academic Publishers].

WO 97/23467 states that the δ receptor has been identified as having a role in many bodily functions such as circulatory and pain systems. Hence, ligands for the δ receptor may therefore find potential use as analgesics and/or antihypertensive agents. In addition, ligands for the δ receptor have also been shown to possess immunomodulatory activities.

WO 97/23467 further states that with few exceptions, currently selective opioid δ ligands are peptidic in nature and are unsuitable for administration by systemic routes. Moreover, some non-peptidic δ antagonists are available but these compounds (e.g. naltrindole) suffer from poor selectivity for the δ receptor vs the μ receptor binding and exhibit no analgesic activity—a fact which highlights the need for the development of selective δ ligands.

WO 95/04051 also states that opioid receptors are characterised as either agonists or antagonists. WO 95/04051 further states that δ receptor agonists and antagonists can be distinguished by their activity in the electrically stimulated mouse vas deferens assay. Further details on this assay are presented in this document.

In more detail, WO 95/04051 discloses diarylmethyl piperazine compounds that are said to bind to the μ, δ and κ receptors. These diarylmethyl piperazine compounds have the general formula:

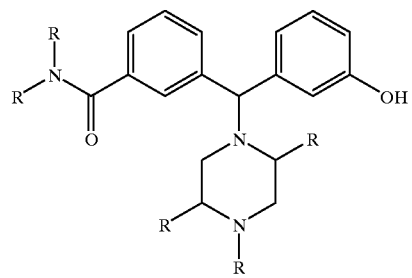

One of the underlined R groups (i.e. R) can be a phenyl group that may be optionally substituted. For the definitions of the other R groups see WO 95/040501.

WO 93/15062 discloses diarylmethyl piperazine compounds and diarylmethyl piperidine compounds that are said to bind to the μ, δ, σ and κ receptors.

WO 97/23466 discloses substituted 7 membered N ring compounds for the treatment of pain. In particular, Examples 14 and 15 of WO 97/23466 disclose a compound of the formula:

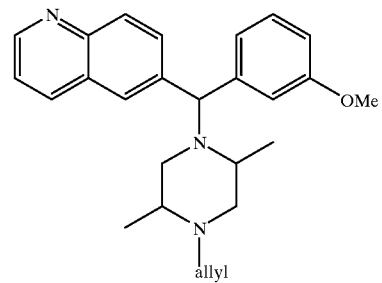

For ease of reference this compound will be called the '466 compound.

WO 97/23467 discloses substituted 7 membered N ring compounds for the treatment of pain.

EP-A-0133 323 discloses antihistaminic benzhydrylpiperazines.

WO 98/52929 (published Nov. 26, 1998; filed Apr. 17, 1998) discloses anti-inflammatory piperazinyl-benzyl-tetrazole derivatives.

According to WO 95/0401, there is a continuing need in the art for improved opioid compounds, particularly compounds which are free of adverse side effects of conventional opiates such as morphine (which is selective for the μ receptor).

The present invention seeks to provide novel compounds and compositions comprising the same that are capable of treating inter alia gastro-intestinal disorders.

Aspects of the present invention are presented in the accompanying claims and in the following text.

According to the present invention there is provided a compound of the formula (I)

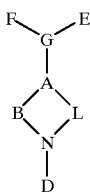

wherein:
A is N or C-X
wherein X is H or $C_{1-4}$ alkyl;
G is C-Y
wherein Y is H or $C_{1-4}$ alkyl;
B is an optional $C_{1-6}$ hydrocarbyl group, optionally substituted;
L is an optional $C_{1-6}$ hydrocarbyl group, optionally substituted;
and wherein A, B, and L in combination with the N constitute a first ring structure which has from 5–7 atoms in the ring;
further wherein:
either D is H or a $C_{1-10}$ hydrocarbyl group,
or D is a $C_{1-10}$ hydrocarbyl group linked to B or L to form a second ring structure which includes the N of the first ring structure, which second ring structure is fused to the first ring structure and which second ring structure has from 5–7 atoms in the ring;
E is a phenyl group substituted by at least one or more of hydroxy, $C_{1-4}$ alkoxy, or $NH_2SO_2$—$C_{1-4}$ alkylene;
F represents a combination of a phenyl group and a heterocyclic group, wherein (i) the heterocyclic group is not a tetrazole,
(ii) the phenyl group is positioned intermediate (in between) G and the heterocyclic group,
(iii) the phenyl group is fused to the heterocyclic group or is linked directly to the heterocyclic group or is attached via a spacer group to the heterocyclic group, wherein the spacer group is any one of $C_{1-4}$ alkylene, carbonyl or $SO_2$, and
(iv) the heterocyclic group is substituted by at least one or more of: a —COOH group, a bio-isostere of a —COOH group, a biolabile ester derivative of a —COOH group, a $C_{1-10}$ hydrocarbyl group comprising one or more —COOH groups, a $C_{1-10}$ hydrocarbyl group comprising one or more bio-isosteres of a —COOH group, or a $C_{1-10}$ hydrocarbyl group comprising one or more biolabile ester derivatives of a —COOH group, or a pharmaceutically acceptable salt of the compound, or a pharmaceutically acceptable solvate of the compound or salt.

It will be appreciated that what is to be claimed includes the following:

(i) a compound of the formula (I) or a pharmaceutically acceptable salt thereof;
(ii) one or more processes for the preparation of a compound of the formula (I) or a pharmaceutically acceptable salt thereof;
(iii) novel intermediates for use in those processes;
(iv) a pharmaceutical composition comprising a compound of the formula (I), or a pharmaceutically acceptable salt thereof, admixed with a pharmaceutically acceptable diluent, carrier or excipient;
(v) a compound of the formula (I), or a pharmaceutically acceptable salt or composition thereof, for use as a medicament;
(vi) the use of a compound of the formula (I), or of a pharmaceutically acceptable salt or composition thereof, for the manufacture of a medicament for the treatment of a gastro-intestinal disease or disorder;
(vii) the use of a compound of the formula (I), or of a pharmaceutically acceptable salt or composition thereof, for the manufacture of a medicament for use as an agonist for δ preceptor;
(viii) a method for the treatment of a gastro-intestinal disease or disorder which method comprises administering to a subject an effective amount of a compound of the formula (I) or a pharmaceutically acceptable salt or composition thereof;
(ix) a method for agonising a δ receptor which method comprises administering to a subject an effective amount of a compound of the formula (I) or a pharmaceutically acceptable salt or composition thereof.

In the above-mentioned uses and methods, the subject is typically a mammal.

The present invention also includes derivatives of the compounds of the present invention, such as peptide conjugate derivatives thereof, hydrates thereof, polymorphs thereof and pro-drug derivatives thereof.

A key advantage of the present invention is that it provides compounds, and compositions comprising the same, that are useful in the treatment of inter alia gastro-intestinal disorders.

The compounds are also advantageous as they are generally less lipophilic than the prior art compounds. Hence the compounds of the present invention may be peripherally active. This is a particularly advantageous feature.

Preferably Y is H. Preferably L and B are a $C_{1-6}$ hydrocarbon group optionally substituted by one or more $C_{1-4}$ alkyl groups. Preferably, G is CH.

E may be optionally further substituted one or more of halo, $C_{1-4}$ alkyl, and halo-$C_{1-4}$ alkyl.

The phenyl group of F may be optionally further substituted with any one or more of halo, hydroxy, cyano, $C_{1-4}$ alkyl, $C_{1-6}$ alkenyl, $C_{1-4}$ alkoxy, $NH_2SO_2$—$C_{1-4}$ alkylene, halo-$C_{1-4}$ alkyl, or other $C_{1-10}$ hydrocarbyl.

If the phenyl group of F is substituted, then preferably the optional substituent(s) is at least any one or more of halo, hydroxy, cyano, $C_{1-4}$ alkyl, $C_{1-4}$ alkenyl, $C_{1-4}$ alkoxy, or halo-$C_{1-4}$ alkyl.

The heterocyclic group of F may be optionally further substituted with any one or more of halo, hydroxy, cyano, $C_{1-4}$ alkyl, $C_{1-6}$ alkenyl, $C_{1-4}$ alkoxy, $NH_2SO_2$—$C_{1-4}$ alkylene, halo-$C_{1-4}$ alkyl, or other $C_{1-10}$ hydrocarbyl.

If the heterocyclic group of F is optionally substituted, then preferably the substituent(s) is at least any one or more of halo, hydroxy, cyano, $C_{1-4}$ alkyl, $C_{1-4}$ alkenyl, $C_{1-4}$ alkoxy, or halo-$C_{1-4}$ alkyl.

For the compounds of formula (I), each of the $C_{1-4}$ alkyl, $C_{1-6}$ alkenyl, $C_{1-4}$ alkoxy, $NH_2SO_2$—$C_{1-4}$ alkylene, halo-$C_{1-4}$ alkyl, and other $C_{1-10}$ hydrocarbyl groups may independently be branched or linear.

The term "hydrocarbyl group" means a group comprising at least C and H and may optionally comprise one or more other suitable substituents. Examples of such substituents may include halo-, alkoxy-, nitro-, an alkyl group, a cyclic group etc. In addition to the possibility of the substituents being a cyclic group, a combination of substituents may form a cyclic group. If the hydrocarbyl group comprises more than one C then those carbons need not necessarily be linked to each other. For example, at least two of the carbons may be linked via a suitable element or group (e.g. carbonyl). Thus, the hydrocarbyl group may contain hetero atoms. Suitable hetero atoms will be apparent to those skilled in the art and include, for instance, sulphur, nitrogen and oxygen.

Preferably, the hydrocarbyl group is any one or more of an alkyl group, an alkylene group, an alkenylene group, an alkenyl group, an alkynylene group, or an aryl group, including combinations thereof (e.g. an arylalkyl group)—which groups may optionally contain one or more heteroatoms or groups, and may further comprise substituents on the chain or rings.

In one preferred embodiment of the present invention, the hydrocarbyl group is a hydrocarbon group.

Here the term "hydrocarbon" means any one of an alkyl group, an alkenyl group, an alkynyl group, which groups may be linear, branched or cyclic, or an aryl group, or combinations thereof (e.g. an arylalkyl group). The term hydrocarbon also includes those groups but wherein they have been optionally substituted. If the hydrocarbon is a branched structure having substituent(s) thereon, then the substitution may be on either the hydrocarbon backbone or on the branch; alternatively the substitutions may be on the hydrocarbon backbone and on the branch.

Preferably D is H or a hydrocarbon.

Preferably D is H, alkyl, alkenyl or aryl alkyl.

Preferably, D is H, $C_1$–$C_6$ alkyl, $C_2$–$C_6$ alkenyl, $C_2$–$C_6$ alkynyl, $C_2$–$C_6$ alkanoyl, $C_3$–$C_7$ cycloalkyl, ($C_3$–$C_7$ cycloalkyl)-($C_1C_4$ alkyl), ($C_1$–$C_4$ alkoxy)-($C_1$–$C_4$ alkyl), carboxy-($C_1$–$C_4$ alkyl), aryl-($C_1$–$C_4$ alkyl) or heteroaryl-($C_1$–$C_4$ alkyl).

Preferably, D is H, $C_1$–$C_6$ alkyl, $C_2$–$C_6$ alkenyl, or aryl-($C_1$–$C_4$ alkyl).

More preferably, D is H, $C_1$–$C_3$ alkyl, $C_2$–$C_4$ alkenyl, or phenyl-($C_1$–$C_3$ alkyl).

For formula (I), each of the optional groups B and L may independently be a branched or a linear $C_1$–$C_6$ alkylene.

As indicated above, compounds of the formula (I) comprise a first ring structure and an optional second ring structure. The compounds of the formula (I) may optionally comprise one or more further cyclic groups. For example, these cyclic groups may be a component of group D. One or more of each of the cyclic groups may independently comprise at least 3 ring members. One or more of each of the cyclic groups may be optionally substituted. One or more of the cyclic groups may be a homocyclic ring structure—such as an $C_6$ aryl group—or a heterocyclic group. An example of an heterocyclic group is piperazine, which may optionally be substituted. For example, with compounds of formula (I), it is possible to have a 5 membered ring joined to, e.g., a 6 membered ring—thus forming a bicyclic piperazine derivative. By way of further example, if one or more of B and L comprises an alkyl substituent then that substituent with D may constitute a cyclic structure.

In the definition of F of formula (I), the heterocyclic group may comprise from 5–10 atoms in the ring structure, where those atoms are each independently selected from C, S, N and O. The heterocyclic group can also be a fused ring.

The heterocyclic group may be linked to the phenyl group in group F in formula (I)—such as by means of a direct link or via a spacer group. For some preferred embodiments, the heterocyclic group is linked directly to the phenyl group in group F.

The heterocyclic group may be fused to the phenyl group in group F in formula (I). If the heterocyclic group is fused to the phenyl group in group F then group F may be any one of an indole, an indazole and a benzimidazole, including substituted variants thereof. For some preferred embodiments, the heterocyclic group is fused to the phenyl group in group F.

Group F is directly attached to Group G in formula (I).

In one preferred embodiment, the group F is a phenyl ring substituted by any 5 or 6 membered heteroaromatic ring structure. Examples of such groups include thiazolyl, oxazolyl, oxadiazolyl, thiadiazolyl, pyridinyl, pyrimidinyl, pyrazolyl, triazolyl, pyridazinyl, pyrazinyl, imidazolyl, furyl, thienyl, pyrrollyl, triazinyl, oxazinyl, isooxazinyl, oxathiazinyl, furanyl, thiophenyl, isoxazolyl, isothiazolyl, etc.

In an alternative preferred embodiment, the group F is a bicyclic heteroaromatic group. Examples of such groups include quinazolinyl, quinolinyl, phthalazinyl, indolyl, indazolyl, benzimadazolyl, benzofuranyl, benzothiophenyl, benzothiazolyl, benzoxazolyl, benzoisoxazolyl, benzoisothiazolyl, quinoxalinyl, cinnolinyl, isoindolyl, indolizinyl, isoquinolinyl, isobenzofuranyl, etc.

In an alternative preferred embodiment the group F is a phenyl ring substituted by a 4,5, or 6 membered saturated or partially saturated heterocyclic ring, examples of which include azetidinyl, pyrollidinyl, piperazinyl, ad piperidinyl.

In an alternative preferred embodiment, the group F is a bicyclic heterocyclic group herein the heterocyclic ring is saturated or partially saturated. Examples of such groups include tetrahydroquinolinyl, tetrahydroisoquinolinyl, indolinyl, isoindolinyl etc.

The group F may be substituted with a group of the formula $R^6$—$(CH_2)_m$—Z—$(CH_2)_n$- where here m is 0, 1, 2 or 3; n is 0, 1, 2 or 3; Z is a direct link or O, $NR^a$ (where $R^a$ is H, $C_{1-6}$ alkyl, or other suitable group), $S(O)_p$ where p is 0, 1 or 2; and $R^6$ is —COOH or a biolabile ester derivative of a —COOH—such as —COO($C_{1-4}$ alkyl)—or a bioisostere thereof. In some preferred embodiments, when Z is O, m is 1, 2 or 3 and n is 2 or 3.

The term "halo" as used herein means means F, Cl, Br or I.

The term "polymorph" means compounds that differ by their crystal lattice (e.g. amorphous compounds and the crystalline form).

The term "prodrug" means a pharmacologically acceptable derivative—e.g. an amide or ester (such as a biolabile ester derivative of a —COOH group)—that is biotransformed to the compound of the present invention. A general reference on prodrugs is Goodman and Gilmans, The Pharmacological Basis of Therapeutics, 8th Edition, McGraw-Hill, Int. Ed. 1992, "Biotransformation of Drugs", p. 13–15.

The term "biolabile ester derivative of a —COOH group" is well understood in medicinal chemistry as meaning an ester which can be readily cleaved in vivo to liberate the corresponding acid of the formula (I)—i.e. so that at least one substituent group attached to the heterocyclic component of group F is —COOH. A number of such ester groups are well-known, for example, in the penicillin area or in the case of the angiotensin-converting enzyme (ACE) inhibitor antihypertensive agents.

Suitable biolabile ester derivatives of a —COOH group have the formula —$COOR^b$—wherein $R^b$ may be $C_1$–$C_6$ alkyl—and they are useful as pro-drugs to provide compounds of the formula (I) wherein the —COOH group is formed in vivo following oral administration. Such esters are also useful as intermediates for the preparation of compounds of the formula (I) wherein the group attached to the heterocyclic component of group F is —COOH.

The suitability of any particular biolabile ester derivative of a —COOH group for this purpose can be assessed by conventional in vitro or in vivo enzyme hydrolysis studies.

Examples of biolabile ester derivatives of a —COOH group are alkyl, alkanoyloxyalkyl (including alkyl, cycloalkyl or aryl substituted derivatives thereof), arylcarbonyl-oxyalkyl (including aryl substituted derivatives thereof), aryl, arylalkyl, indanyl and haloalkyl: wherein alkanoyl groups have from two to eight carbon atoms, alkyl groups have from one to eight carbon atoms and aryl means phenyl or naphthyl, both of which may be optionally substituted by $C_1$–$C_4$ alkyl, $C_1$–$C_4$ alkoxy or halo. Alkyl, alkanoyl and alkoxy groups can, where appropriate, be straight- or branched-chain.

Specific examples of biolabile ester derivatives of a —COOH group are $C_1$–$C_6$ alkyl (e.g. methyl, ethyl, n-propyl, isopropyl), benzyl, 1-(2,2-diethylbutyryloxy) ethyl, 2-ethyl-propionyloxymethyl, 1-(2-ethylpropionyloxy) ethyl, 1–2,4-dimethylbenzoyloxy)ethyl, (α-benzoyloxybenzyl, 1-(benzoyloxy)ethyl, 2-methyl-1-propionyloxy-1-propyl, 2,4,6-trimethylbenzoyloxymethyl, 1-(2,4,6-trimethyl-benzoyloxy)ethyl, pivaloyloxymethyl, phenethyl, phenpropyl, 2,2,2-trifluoroethyl, 1- or 2-naphthyl, 2,4-dimethylphenyl, 4-t-butylphenyl and 5-indanyl.

The term "bio-isostere" is used in its normal sense—namely a similar (but not the same) or a different chemical structure and having the same biological functional effect. An example of a bio-isostere of a carboxyl group is a tetrazolyl.

Preferably, the compounds of the present invention have the following general formula (FI):

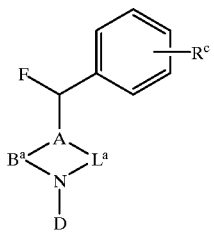

(FI)

wherein

A, F and D are as defined above for formula (I), $R^c$ is at least one or more of OH, $C_{1-4}$ alkoxy, or $NHSO_2$—($C_{1-4}$ alkyl), $B^a$ is $C_{0-6}$ alkylene (which may be branched or linear), $L^a$ is $C_{0-6}$ alkylene (which may be branched or linear), and wherein A, $L^a$, $B^a$ and N together constitute a five membered ring or six membered ring or a seven membered ring.

Preferably, the compounds of the present invention have the following general formula (FII):

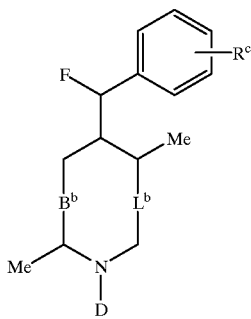

(FII)

wherein

A, F and D are as defined above for formula (I), $R^c$ is at least one or more of OH, $C_{1-4}$ alkoxy, or $NHSO_2$—($C_{1-4}$ alkyl), $B^b$ is $(CH_2)_m$ where here m=0 or 1, $L^b$ is $(CH_2)_m$ where here m=0 or 1, and wherein A, $B^b$, $L^b$ and N together with the carbon atoms in the ring constitute a six membered ring or a seven membered ring.

More preferably, the compounds of the present invention have the following general formula (FIII)

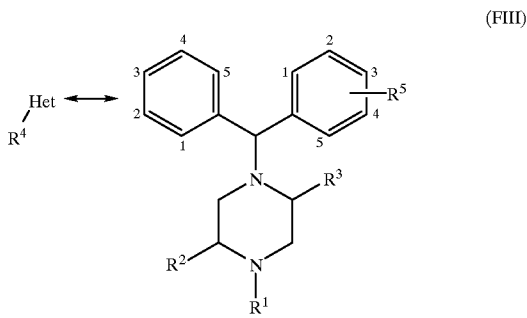

(FIII)

wherein

Het represents the heterocyclic group, the double arrow means that Het can be linked to or fused with the phenyl group, preferably wherein the Het is directly linked or fused to the phenyl group, $R^1$ is H, $C_2$–$C_6$ alkanoyl, $C_1$–$C_6$ alkyl, $C_2$–$C_6$ alkenyl, $C_2$–$C_6$ alkynyl, $C_3$–$C_7$ cycloalkyl, ($C_3$–$C_7$ cycloalkyl)-($C_1$–$C_4$ alkyl), ($C_1$$C_4$ alkoxy)-($C_1$$C_4$ alkyl), carboxy-($C_1$–$C_4$ alkyl), aryl-($C_1$–$C_4$ alkyl) or heteroaryl-($C_1$–$C_4$ alkyl), more preferably $C_1$–$C_6$ alkyl, $C_2$–$C_6$ alkenyl, or aryl-($C_1$–$C_4$ alkyl), more preferably $C_1$–$C_3$ alkyl, $C_2$–$C_4$ alkenyl, or phenyl-($C_1$–$C_3$ alkyl).

$R^2$ and $R^3$ are each independently H or $C_1$–$C_4$ alkyl, more preferably H or methyl;

wherein optionally $R^1$ and $R^2$ may be taken together (i.e. linked together) to represent $C_{1-6}$ alkylene;

$R^4$ is selected from (i) —COOH or a bio-isostere thereof or a bio-labile ester derivative of a —COOH group;

(ii) a hydrocarbyl group comprising —COOH or a bio-isostere thereof or a bio-labile ester derivative of a —COOH group, such as for example a group of the formula $R^6$—$(CH_2)_m$—Z—$(CH_2)_n$—, where here m is 0, 1, 2 or 3, where here n is 1, 2 or 3, where here Z is a direct link, NH, N($C_1$–$C_4$ alkyl) or O, and wherein any of the $CH_2$ groups may be optionally substituted, and wherein $R^6$ is —$CO_2H$ or a bio-labile ester derivative of a —COOH group such as —$CO_2(C_1–C_4$ alkyl), or a bio-isostere of a —COOH group, and (iii) a group of the formula

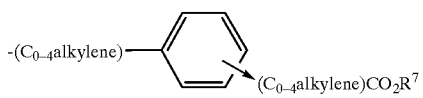

wherein the $C_{0-4}$ alkylene group may be optionally substituted or may be a carbonyl derivative thereof;
wherein $R^7$ is H or $C_1–C_4$ alkyl;
and $R^5$ is hydroxy, $C_1–C_4$ alkoxy or —$NHSO_2(C_1–C_4$ alkyl), wherein $R^5$ can be attached to any one of positions 1, 2, 3, 4 and 5, preferably to position 2 or position 4;

Het may be optionally further substituted with one or more $C_{1-4}$ alkyl groups (which may be the same or different);
with the proviso that when Z is O, m is 1, 2 or 3 and independently n is 1, 2 or 3.

Where appropriate in formula (FIII), the alkyl, alkanoyl, alkoxy, alkenyl and alkynyl groups can be linear or branched chain.

A preferred formula for compounds of the formula (FIII) is presented as formula (FIIIa)

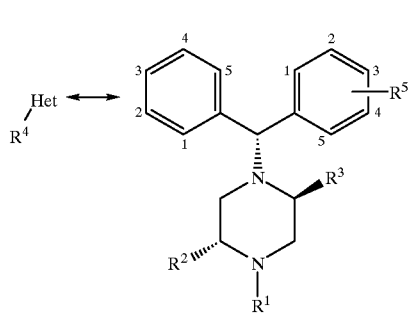

(FIIIa)

The preferred phenyl group nearest to the Het group (as shown diagramatically above) for formula (FIII) is optionally substituted by Up to three substituents each of which is independently selected from halo, trifluoromethyl, $C_1–C_4$ alkyl and $C_1–C_4$ alkoxy.

More preferably, the phenyl group of formula (FIII) is optionally substituted by one or two substituents as defined above.

For formula (FIII), the heterocyclic group is as defined hereinbefore, such as a 5- or 6-membered aromatic heterocyclic group, such as thiazolyl, oxazolyl, oxadiazolyl, thiadiazolyl, pyridinyl, pyrimidinyl, pyrazolyl, triazolyl, pyridazinyl, pyrazinyl, imidazolyl, furyl, thienyl, pyrrollyl, piperazinyl, triazinyl, oxazinyl, isooxazinyl, oxathiazinyl, furanyl, thiophenyl, isoxazolyl, isothiazolyl, etc.

For formula (FIII), the preferred alkyl groups are methyl and ethyl.

For formula (FIII), the preferred alkoxy groups are methoxy and ethoxy.

For formula (FIII), the preferred alkanoyl group is acetyl.

For formula (FIII), the preferred alkenyl group is allyl or vinyl.

For formula (FIII), the preferred cycloalkyl group is cyclopropyl.

For compounds of formula (FIII), the heterocyclic group is preferably attached to the 3-and/or 4- position of the adjacent phenyl ring.

Preferably for compounds of formula (FIII):

$R^1$ is H, alkyl, alkenyl, or phenyl(alkyl);

$R^2$ is methyl or H;

$R^3$ is methyl or H;

$R^5$ is hydroxy or methoxy;

$R^4$ is any one or more of
—COOH,
a biolabile ester derivative of a —COOH group, preferably —$COO(C_1–C_4$ alkyl),
a bio-isostere of a —COOH group,
—$(CH_2)_qCO_2H$ where q is 1, 2, 3 or 4,
—$(CH_2)_qCO_2(C_1–C_4$ alkyl) where q is 1, 2, 3 or 4,
—$(CH_2)_2$—O—$CH_2CO_2H$,
—$(CH_2)_2$—O—$CH_2CO_2(C_1–C_4$ alkyl),
—NH—$CH_2COOH$,
—NH—$CH_2COO(C_1–C_4$ alkyl),
—N(Me)—$CH_2COOH$,
—N(Me)—$CH_2COO(C_1–C_4$ alkyl),
—$CH_2NH$—$CH_2COOH$,
—$CH_2NH$—$CH_2COO(C_1–C_4$ alkyl),
—$CH_2N(Me)$—$CH_2COOH$,
—$CH_2N(Me)$—$CH_2COO(C_1–C_4$ alkyl),
—($C_{0-4}$ alkylene)-phenyl-($C_{0-4}$ alkylene)—COOH,
—($C_{0-4}$ alkylene)-phenyl-($C_{0-4}$ alkylene)—COO ($C_1–C_4$ alkyl);
—(CO)-phenyl-($C_{0-4}$ alkylene)—COOH; and
—(CO)-phenyl-($C_{0-4}$ alkylene)—COO($C_{1-4}$ alkyl).

wherein $R^1$ and $R^2$ may be optionally linked to each other so as to form a 1,3 propylene group; and wherein optionally the Het is further substituted with one or more $C_{1-4}$ alkyl groups (which may be the same or different).

A preferred compound of the present invention has the formula (FIV)

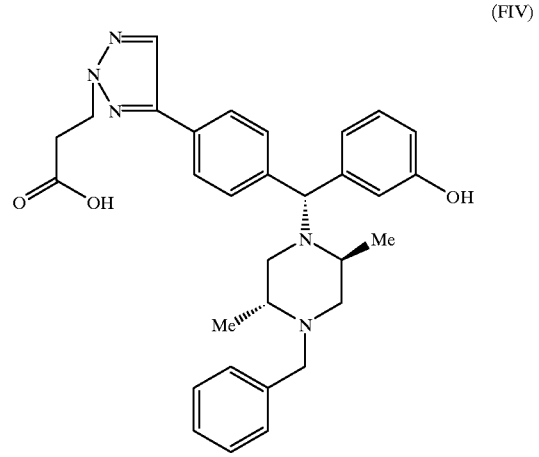

(FIV)

Additional preferred compounds are presented below as formulae (FVI), (FVII), (FVIII) and (FVIX). In these formulae, n is 0 or an integer from 1 to 5; and R is H or Me.

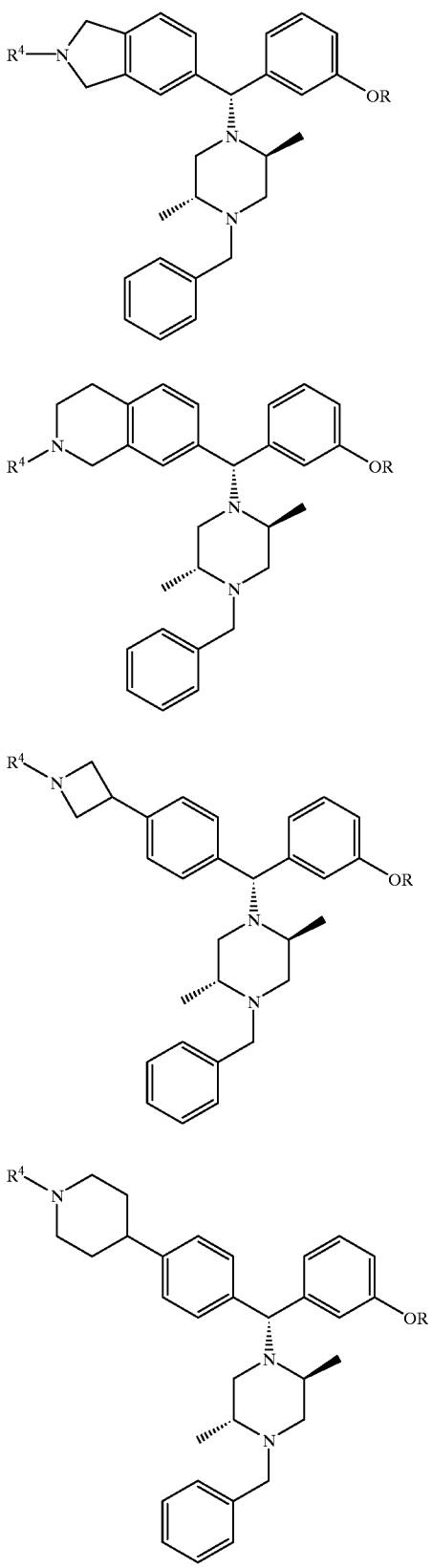

(FVI)

(FVII)

(FVIII)

(FIX)

wherein $R^4$ is as defined hereinbefore.

More preferably, $R^4$ is —COOH, —$(CH_2)_q$COOH, were q is 1,2,3 or 4, —(CO)-phenyl-($C_{0-4}$ alkylene)COOH or $C_{1-4}$ alkyl esters of any of these.

These compounds are examples of partially or fully saturated heterocyclic groups (fused with or linked/substituted to the phenyl group), and provide additional stability, because of the additional basic center on the heterocyclic group, over the heteroaromatic groups. We found that the preferred compounds of the present invention are selective for the δ-opioid receptor over the μ and κ opioid receptors and are potent agonists in the mouse was deferens functional assay in vitro. In particular, these compounds have the potential for peripherally selective treatment for gastrointestinal disorders such as irritable bowel syndrome and diarrhoea, urinary urge incontinence, and pain.

Thus the present invention provides compounds (and compositions comprising the same) which are δ opioid agonists which are useful for preventing or treating inflammatory diseases such as arthritis, psoriasis, asthma, or inflammatory bowel disease, disorders of respiratory function, gastrointestinal disorders such as functional bowel disease, functional GI disorders such as irritable bowel syndrome, functional diarrhoea, functional distension, functional pain, non-ulcerogenic dyspepsia or others associated with disorders of motility or secretion, urogenital tract disorders such as incontinence, as analgesics for treating pain including non-somatic pain, or as immunosuppressants to prevent rejection in organ transplant and skin graft.

In some instances, the compounds of the present invention (and the compositions comprising the same) are potent δ opioid agonists. In some instances, the compounds of the present invention (and the compositions comprising the same) which are selective δ opioid agonists. In other instances, the compounds of the present invention (and the compositions comprising the same) are potent and selective δ opioid agonists.

The compounds of the present invention (including compositions comprising the same) may also be used for preventing or treating conditions such as mental illnesses, drug additions, drug overdoses, lung oedema, depression, emphysema, apnoea and spinal injuries.

Further uses of the compounds and compositions of the present invention include their use in treatment of the sympathetic nervous system (e.g. hypertension). Also, they may be used in the field of diagnosis—such as PET scanning—whereby the compounds would be appropriately labelled.

The pharmaceutically acceptable salts of the compounds of the formula (I) include suitable acid addition or base salts thereof. For a review on suitable pharmaceutical salts see Berge et al, J Pharm Sci, 66, 1–19 (1977).

By way of example, suitable acid addition salts are formed from acids which form non-toxic salts. Suitable examples of such salts are the hydrochloride, hydrobromide, hydroiodide, sulphate, bisulphate, phosphate, hydrogen phosphate, acetate, maleate, fumarate, lactate, tartrate, citrate, gluconate, benzoate, methanesulphonate, benzenesulphonate and p-toluenesulphonate salts.

Also by way of example, suitable base salts are formed from bases which form non-toxic salts. Suitable examples thereof are the aluminum, calcium, lithium, magnesium, potassium, sodium, zinc, N-benzyl-N-(2-phenylethyl) amine, 1-adamantylamine and diethanolamine salts.

Preferred base salts are the sodium, potassium, N-benzyl-N-(2-phenylethyl)amine and 1-adamantylamine salts.

Compounds of the present invention may contain one or more asymmetric carbon atoms and/or one or more nonaromatic carbon-carbon double bonds and may therefore exist in two or more stereoisomeric forms. Thus, the present invention also provides both the individual stereoisomers of the compounds of the formula (I), as well as mixtures thereof, including compositions comprising the same. Separation or diastereoisomers or cis and trans isomers may be achieved by conventional techniques, e.g. by fractional crystallisation, chromatography or HPLC of a stereoisomeric mixture of a compound of the formula (I) or a suitable salt or derivative thereof. An individual enantiomer of a compound of the formula (I) may also be prepared from a corresponding optically pure intermediate or by resolution, such as by HPLC of a racemate using a suitable chiral support or by fractional crystallisation of the diastereoisomeric salts formed by reaction of a racemate with a suitable optically active acid or base.

As mentioned above, the present invention also covers pharmaceutical compositions comprising the compounds of the general formula (I). In this regard, and in particular for human therapy, even though the compounds of the present invention (including their pharmaceutically, acceptable salts and pharmaceutically acceptable solvates) can be administered alone, they will generally be administered in admixture with a pharmaceutical carrier, excipient or diluent selected with regard to the intended route of administration and standard pharmaceutical practice.

By way of example, in the pharmaceutical compositions of the present invention, the compounds of the present invention may be admixed with any suitable binder(s), lubricant(s), suspending agent(s), coating agent(s), solubilising agent(s).

In general, a therapeutically effective daily oral or intravenous dose of the compounds of formula (I) and their salts is likely to range from 0.01 to 50 mg/kg body weight of the subject to be treated, preferably 0.1 to 20 mg/kg. The compounds of the formula (I) and their salts may also be administered by intravenous infusion, at a dose which is likely to range from 0.001–10 mg/kg/hr.

Tablets or capsules of the compounds may be administered singly or two or more at a time, as appropriate. It is also possible to administer the compounds in sustained release formulations.

Typically, the physician will determine the actual dosage which will be most suitable for an individual patient and it will vary with the age, weight and response of the particular patient. The above dosages are exemplary of the average case. There can, of course, be individual instances where higher or lower dosage ranges are merited, and such are within the scope of this invention.

Alternatively, the compounds of the general formula (I) can be administered by inhalation or in the form of a suppository or pessary, or they may be applied topically in the form of a lotion, solution, cream, ointment or dusting powder. An alternative means of transdermal administration is by use of a skin patch. For example, they can be incorporated into a cream consisting of an aqueous emulsion of polyethylene glycols or liquid paraffin. They can also be incorporated, at a concentration of between 1 and 10% by weight, into an ointment consisting of a white wax or white soft paraffin base together with such stabilisers and preservatives as may be required.

For some applications, preferably the compositions are administered orally in the form of tablets containing excipients such as starch or lactose, or in capsules or ovules either alone or in admixture with excipients, or in the form of elixirs, solutions or suspensions containing flavouring or coloring agents.

The compositions (as well as the compounds alone) can also be injected parenterally, for example intracavernosally, intravenously, intramuscularly or subcutaneously. In this case, the compositions will comprise a suitable carrier or diluent.

For parenteral administration, the compositions are best used in the form of a sterile aqueous solution which may contain other substances, for example enough salts or monosaccharides to make the solution isotonic with blood.

For buccal or sublingual administration the compositions may be administered in the form of tablets or lozenges which can be formulated in a conventional manner.

For oral, parenteral, buccal and sublingual administration to subjects (such as patients), the daily dosage level of the compounds of the present invention and their pharmaceutically acceptable salts and solvates may typically be from 10 to 500 mg (in single or divided doses). Thus, and by way of example, tablets or capsules may contain from 5 to 100 mg of active compound for administration singly, or two or more at a time, as appropriate. As indicated above, the physician will determine the actual dosage which will be most suitable for an individual patient and it will vary with the age, weight and response of the particular patient. It is to be noted that whilst the above-mentioned dosages are exemplary of the average case there can, of course, be individual instances where higher or lower dosage ranges are merited and such dose ranges are within the scope of this invention.

Thus the invention provides a pharmaceutical composition comprising a compound of the present invention, or a pharmaceutically acceptable salt thereof, or a pharmaceutically acceptable solvate of either entity, together with a pharmaceutically acceptable diluent, excipient or carrier.

The invention further provides a compound of the present invention, or a pharmaceutically acceptable salt thereof, or a pharmaceutically acceptable solvate of either entity, or a pharmaceutical composition containing any of the foregoing, for use as a human medicament.

The present invention also provides a veterinary formulation comprising a compound of the present invention, or a veterinarily acceptable salt thereof, or a veterinarily acceptable solvate of either entity, together with a veterinarily acceptable diluent, excipient or carrier.

For veterinary use, a compound of the present invention or a veterinarily acceptable salt thereof, or a veterinarily acceptable solvate of either entity, is typically administered as a suitably acceptable formulation in accordance with normal veterinary practice and the veterinary surgeon will determine the dosing regimen and route of administration which will be most appropriate for a particular animal. However, as with human treatment, it may be possible to administer the compound alone for veterinary treatments.

In addition, the present invention provides a compound of the present invention, or a veterinarily acceptable salt thereof, or a veterinarily acceptable solvate of either entity, or a veterinary formulation containing any of the foregoing, for use as an animal medicament.

In summation, the present invention provides compounds of the formula (I) or salts or solvates thereof, as well as the uses thereof

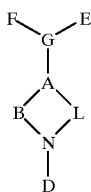

(I)

The compounds of the formula (I) can be prepared by conventional routes.

The compounds of the present invention may be prepared by any one of the general synthesis protocols presented in the in the Route Section (infra), or by any one of the more specific synthesis protocols presented in the Examples Section (infra)—which are presented as either Preparations or Examples. The present invention also encompasses any one or more of these processes, in addition to any novel intermediate(s) obtained therefrom.

In the following sections, the $^1$H nuclear magnetic resonance (NMR) spectra were recorded using either a Varian Unity 300 or a Varian Inova 400 spectrometer and were in all cases consistent with the proposed structures. Characteristic chemical shifts ($\delta$) are given in parts-per-million downfield from tetramethylsilane using conventional abbreviations for designation of major peaks: e.g. s, singlet; d, doublet; t, triplet; q, quartet; m, multiplet; br, broad. The mass spectra (m/z) were recorded using a Fisons Instruments Trio mass spectrometer in the thermospray ionisation mode. In the following sections, room temperature means 20 to 25° C.

In the following Examples and Preparations, ethyl acetate is sometimes referred to as "EtOAc" and methanol is sometimes referred to as "MeOH".

In the following Examples and Preparations, and with particular reference to the specific eluents used, occasionally ammonium hydroxide is referred to as "NH$_3$".

For ease of reference, it is to be noted that there is no Example 32; and Examples 35 and 36 disclose the preparation of compounds that are then used to make the therapeutic compounds according to the present invention.

ROUTE SECTION

Route 1

Compounds of the formula (I) in which A is N can be prepared by the reaction of a compound of the formula:

(II)

where E, F and G are as defined for formula (I) and Lg is defined as a leaving group e.g. Cl, Br, I, mesylate, and tosylate, with a compound of the formula:

(III)

where B, D, and L are as defined for formula (I), in the presence or in the absence of a suitable base, such as potassium carbonate, in a suitable organic solvent such as dry toluene at room temperature to the reflux temperature. If necessary substituents on E and F can be protected prior to reaction and the protecting group subsequently removed using standard techniques.

Route 2

Compounds of the formula (I) can also be prepared by reaction of a carbonyl compound of the formula:

(IV)

where F and Y are defined as for formula (I), with a compound of the formula

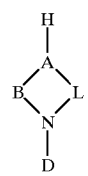

(V)

where A is defined as N and B, D and L are as defined for formula (I), in the presence of benzotriazole, typically under reflux in an organic solvent such as dry toluene with azeotropic removal of water, in the presence or absence of molecular sieves, followed by cooling, e.g. to −20° C. and reaction with a Grignard reagent of the formula:

E—MgBr  (VI)

If necessary substituents on E and F can be protected prior to reaction and the protecting group subsequently removed using standard techniques.

A preferred intermediate according to the invention is compound of Formula (IVA):

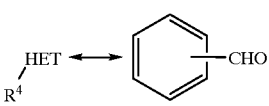

Wherein, the HET group and R$^4$ are as defined hereinbefore, and more particularly are the same as for Formula (FIII).

Route 3

Compounds of the formula (I) can also be prepared by reaction of compounds of the formula:

(VII)

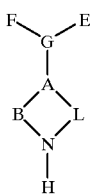

where A, B, E, F, G, and L are as defined for formula (I), with an alkylating agent of the formula:

D—Lg  (VIII)

where D is defined as for formula (I) and Lg is defined as for formula (II), in the presence or absence of a suitable base such as potassium carbonate in a suitable organic solvent such as dry toluene at room temperature to the reflux temperature. If necessary substituents on E and F can be protected prior to reaction and the protecting group subsequently removed using standard techniques.

Route 4

Compounds of the formula (I) can also be prepared by reductive alkylation of a compound of the formula:

(VIII)

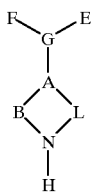

where A, B, E, F, G, and L are as defined for formula (I), with a carbonyl compound of the formula:

(IX)

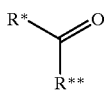

where R* CR** is defined as being equivalent to D in formula (I), in the presence of a suitable reducing agent such as sodium triacetoxyborohydride in a suitable organic solvent such as tetrahydrofuran at from 0° C. to the reflux temperature. If necessary substituents on E and F can be protected prior to reaction and the protecting group subsequently removed using standard techniques.

Route 5

Compounds of the formula (I), where A is defined as N, can also be prepared by reaction of an amine of the formula:

(X)

where E, F and G are defined as for formula (I), with a compound of the formula:

(XI)

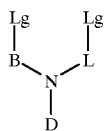

where B, D and L are as defined for formula (I) and Lg is as defined for formula (II), in the presence of a suitable base such as potassium carbonate in a suitable solvent such as toluene at a temperature of room temperature to the reflux temperature. If necessary substituents on E and F can be protected prior to reaction and the protecting group subsequently removed using standard techniques.

Route 6

Compounds of the formula (III) in which $R^5$ is hydroxy can be prepared by the reaction of the corresponding methoxy compounds of the formula (III) with a suitable reagent such as boron tribromide in a suitable solvent such as dichloromethane at a temperature from 0° C. to room temperature. Alternative methods of deprotection as described in T. W. Greene and P. G. M. Wuts in Protective Groups in Organic Synthesis, $2^{nd}$ Edition, Wiley-Interscience may also be used as appropriate.

Route 7

Compounds of the formula (III) in which $R^5$ is hydroxy can also be prepared by the deprotection of the corresponding ether derivatives of the formula (III) with a suitable reagent such as described in T. W. Greene and P. G. M. Wuts in Protective Groups in Organic Synthesis, $2^{nd}$ Edition, Wiley-Interscience.

Route 8

Compounds of the formula (III) wherein the heterocycle is directly linked with the phenyl group can be prepared by suitably catalysed cross coupling of a compound of the formula:

(XII)

where Het and $R^4$ are defined as for formula (III), and Q is halo or trifluoromethanesulphonyl, with a compound of the formula:

(XIII)

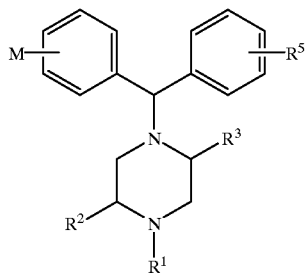

wherein $R^1$, $R^2$, $R^3$ and $R^5$ are as defined for the formula (III) and M is an optionally substituted metal substituent suitable for cross-coupling reactions, eg a trialkystanne such as tri-n-butylstanne; e.g. a dialkylborane such as diethylborane; lithium; halomagnesium; chlorozinc; copper; aryl or chloromercury; dihydroxyborane; dialkoxyborane. Such reactions should be carried out in the presence of a suitable palladium or nickel catalyst. The type of catalyst will vary with the character of M, the substrate and the structure of the compound of the formula (III).

In a typical procedure a compound of the formula (XIII) where M is tri-n-butylstannane, is reacted with a compound of the formula (XII) in the presence of a palladium catalyst, e.g. tetrakistriphenylphosphinepalladium (0), in a suitable solvent, e.g. toluene. The reaction can be carried out at from room temperature to, and preferably at, the reflux temperature of the solvent and is preferably carried out under an inert atmosphere, e.g. under argon or nitrogen. If necessary $R^4$ and $R^5$ can be protected prior to reaction and the protecting group subsequently removed using standard techniques.

Compounds of the formula (XIII) can be prepared by suitable metallation of a compound of the formula:

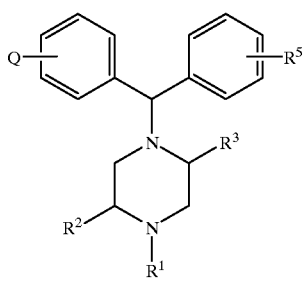

(XIV)

wherein $R^1$, $R^2$, $R^3$ and R4 are as defined for the formula (III) and Q is as defined for a compound of the formula (XII).

In a typical procedure for the preparation of a compound of the formula (XIII) wherein M is trialkylstannane, e.g. tri-n-butylstannane a compound of the formula (XIV) is reacted with a hexaalkyldistannane e.g. hexa-n-butyldistannane, in the presence of a suitable catalyst, e.g. palladium (II) acetate, a suitable base, e.g. triethylamine, a suitable triarylphosphine, e.g. tri-o-tolylphosphine, and in a suitable solvent, e.g. acetonitrile. If necessary $R^5$ can be protected prior to reaction and the protecting group subsequently removed using standard techniques.

In an alternative typical procedure for the preparation of a compound of the formula (XIII) wherein M is trialkylstannane, e.g. tri-n-butylstanne, a compound of the formula (XIV) is reacted with an alkyllithium, e.g. t-butyllithium in suitable solvent, e.g. tetrahydrofuran and the resultant solution is treated with the corresponding trialkylstannyl halide, e.g. tri-n-butylstannyl chloride, or the corresponding hexaalkyldistannane, e.g. hexa-n-butyldistannane. If necessary $R^5$ can be protected prior to reaction and the protecting group subsequently removed using standard techniques.

Route 9

Compounds of the formula (III) wherein the heterocycle is directly linked with the phenyl group can be prepared by suitably catalysed cross coupling of a compound of the formula:

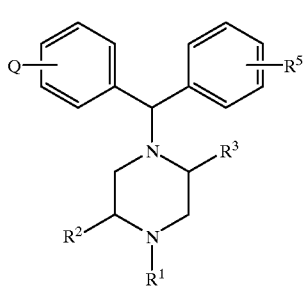

(XV)

where $R^1$, $R^2$ $R^3$ and $R^5$ are defined as for formula (III), and Q is defined as for formula (XII), with a compound of the formula:

(XVI)

wherein Het is defined as for formula (III) and M is an optionally substituted metal substituent suitable for cross-coupling reactions as defined for formula (XIII). Such reactions should be carried out in the presence of a suitable palladium or nickel catalyst. The type of catalyst will vary with the character of M, the substrate and the structure of the compound of the formula (III).

In a typical procedure a compound of the formula (XVI) where M is halozinc, preferably chlorozinc, is prepared by reaction with an alkyllithium, e.g. n-butyllithium at a temperature of $-78°$ C. to room temperature, in suitable solvent, e.g. tetrahydrofuran and the resultant solution is treated with zinc (II) chloride (solution in diethyl ether) and the resultant solution treated with a compound of the formula (XV) in the presence of a palladium catalyst, e.g. tetrakistriphenylphosphinepalladium (0), in a suitable solvent, e.g. tetrahydrofuran. The reaction can be carried out at from room temperature to, and preferably at, the reflux temperature of the solvent and is preferably carried out under an inert atmosphere, e.g. under argon or nitrogen. If necessary $R^4$ and $R^5$ can be protected prior to reaction and the protecting group subsequently removed using standard techniques.

Route 10

Compounds of the formula (III) wherein the heterocycle is a 1,2,3-triazole and is directly linked with the phenyl group can be prepared by reaction of a compound of formula:

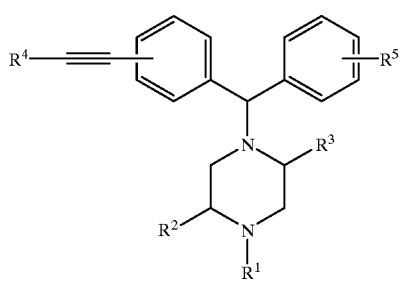
(XVII)

wherein $R^1$, $R^2$, $R^3$, $R^4$ and $R^5$ are as defined for formula (III), with a compound of the formula:

$$N_3\text{—}M_2 \quad \text{(XVIII)}$$

where $M_2$ is defined as a suitable metal substituent, e.g. sodium, tri-n-butylstannyl, trimethylsilyl, or hydrogen in a suitable solvent, e.g. toluene or dimethylformamide, at a temperature of room temperature to the reflux temperature of the solvent either at atmospheric pressure or at raised pressure. If necessary $R^5$ can be protected prior to reaction and the protecting group subsequently removed using standard techniques.

Route 11

Compounds of the formula (III) wherein the heterocycle is a 1,2,3-triazole and is directly linked with the phenyl group can be prepared by reaction of a compound of formula:

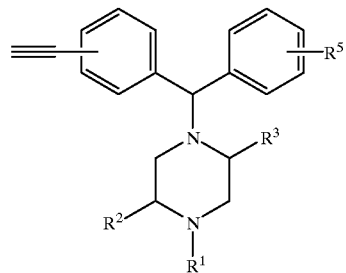
(XIX)

wherein $R^1$, $R^2$, $R^3$, and $R^5$ are as defined for formula (III), with a compound of the formula:

$$N_3\text{—}R^4 \quad \text{(XX)}$$

where $R^4$ is defined as for formula (III) in a suitable solvent, e.g. toluene or dimethylformamide, at a temperature of room temperature to the reflux temperature of the solvent either at atmospheric pressure or at raised pressure. If necessary $R^4$ and $R^5$ can be protected prior to reaction and the protecting group subsequently removed using standard techniques.

Route 12

Compounds of the formula (III) wherein the heterocycle is directly linked with the phenyl group can also be prepared by reaction of a compound of formula:

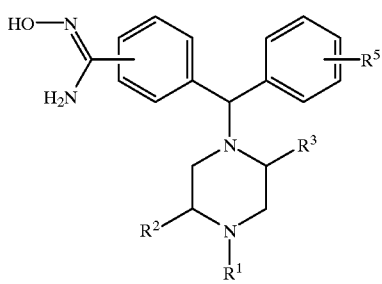
(XXI)

wherein $R^1$, $R^2$, $R^3$, and $R^5$ are as defined for formula (III), with a compound of the formula:

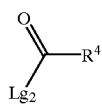
(XXII)

wherein $R^4$ is as defined for formula (III) and $Lg_2$ is defined as a leaving group such as halo, e.g. chloro, or alkoxy, e.g. methoxy, in a suitable solvent such as tetrahydrofuran at a temperature from room temperature to the reflux temperature. If necessary $R^4$ and $R^5$ can be protected prior to reaction and the protecting group subsequently removed using standard techniques.

Route 13

Compounds of the formula (III) wherein the heterocycle is directly linked with the phenyl group can also be prepared by reaction of a compound of formula:

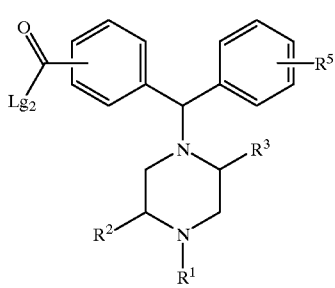
(XXIII)

wherein $R^1$, $R^2$, $R^3$, $R^5$ are as defined for formula (III) and $Lg_2$ is defined for formula (XXII) with a compound of the formula:

(XXIV)

$$\text{HO}\text{—}\underset{H_2N}{\overset{N}{\|}}\text{—}R^4$$

wherein $R^4$ is as defined for formula (III) in a suitable solvent such as tetrahydrofuran at a temperature from room temperature to the reflux temperature. If necessary $R^4$ and $R^5$ can be protected prior to reaction and the protecting group subsequently removed using standard techniques.

Route 14

Compounds of the formula (III) wherein the heterocycle is directly linked with the phenyl group can also be prepared by reaction of a compound of the formula:

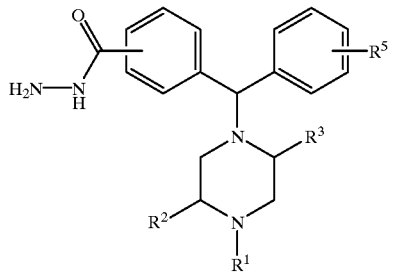

(XXV)

wherein $R^1$, $R^2$, $R^3$, $R^5$ are as defined for formula (III), with a compound of the formula:

(XXVI)

wherein $R^4$ is as defined for formula (III) and and $Lg_2$ is defined for formula (XXII) in a suitable solvent such as tetrahydrofuran at a temperature from room temperature to the reflux temperature. If necessary $R^4$ and $R^5$ can be protected prior to reaction and the protecting group subsequently removed using standard techniques.

EXAMPLES

Example 1

2-(3-{4-[(R)-1-[(2S,5R)-4-allyl-2,5-dimethylhexahydropyrazin-1-yl]-1-(3-methoxyphenyl)methyl]phenyl}-1H-1,2,4-triazol-1-yl)acetic acid

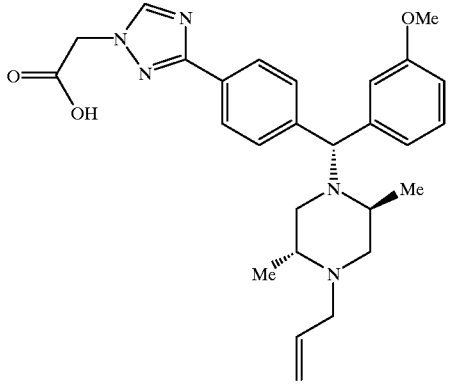

A suspension of the compound of Preparation 8 (210 mg), ethyl bromoacetate (80 μl), and potassium carbonate (200 mg) in acetonitrile (15 ml) was heated under reflux for 4 hours. On cooling, the reaction mixture was adsorbed onto silica gel, and purified by column chromatography over silica (90/10/0.75 hexane/isopropanol/ammonium hydroxide) to afford the ethyl ester of the title compound.

Aqueous sodium hydroxide solution (2 ml, 5N) was added to a solution of the intermediate ester in dioxan (6 ml) and water (6 ml), and the reaction stirred at room temperature for 2 hours. The mixture was acidified to pH 2 with 5N hydrochloric acid and immediately rebasified to pH 9 with ammonium hydroxide solution, and evaporated to dryness in vacuo. The residue was purified by column chromatography over silica gel using gradient elution (90/10/2 to 80/20/3 dichloromethane/methanol/ammonium hydroxide) to afford the title compound as a colorless solid, 120 mg.

m/z: 476 (MH⁺)

$R_f$: 0.21 (80/20/3 dichloromethane/methanol/ammonium hydroxide) $δ_H$ (300 MHz, DMSO-d₆): 8.48 (1H, s), 7.90 (2H, d), 7.46 (2H, d), 7.26 (1H, dd), 6.86 (3H, m), 5.80 (1H, m), 5.18 (2H, 2xd), 5.04 (3H, m), 3.73 (3H, s), 3.24 (1H, dd), 3.00 (1H, dd), 2.82 (1H, d), 2.64 (3H, m), 2.26 (1H, dd), 1.95 (1H, dd), 1.10 (3H, d), 1.00 (3H, d).

Examples 2 and 3

5-(3-{4-[(R)-1-[(2S,5R)-4-allyl-2,5-dimethylhexahydropyrazin-1-yl]-1-(3-methoxyphenyl)methyl]phenyl}-1H-1,2,4-triazol-1-yl)pentanoic acid and 5-(5-{4-[(R)-1-[(2S,5R)-4-allyl-2,5-dimethylhexahydropyrazin-1-yl]-1-(3-methoxyphenyl)methyl]phenyl}-1H-1,2,4-triazol-1-yl)pentanoic acid The following compounds of the general formula:

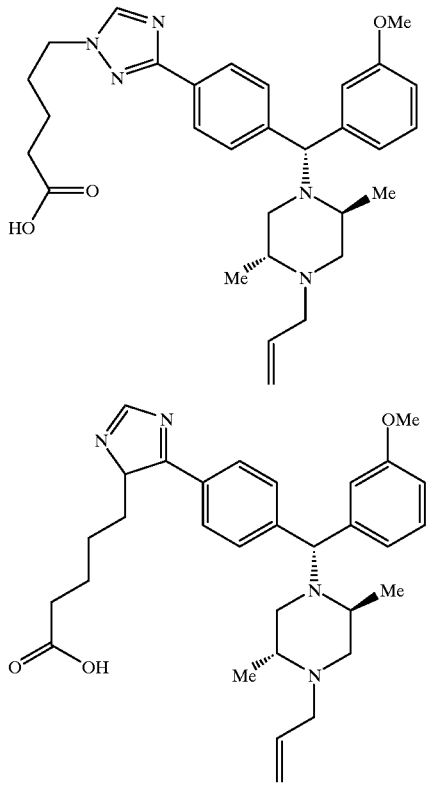

were prepared by a similar method to that described for Example 1 from the compound of Preparation 8 and ethyl 5-bromovalerate, followed by saponification.

Example 2 m/z: 518 (MH+)

$R_f$: 0.23 dichloromethane/methanol/ammonium hydroxide (80/20/3)

$\delta_H$ (300 MHz, CDCl$_3$): 8.12 (1H, s), 7.99 (2H, d), 7.48 (2H, d), 7.20 (1H, dd), 6.80 (3H, m), 5.90 (1H, m), 5.10 (3H, m), 4.19 (2H, t), 3.78 (3H, s), 3.39 (1H, dd), 3.03 (1H, m), 2.92 (1H, d), 2.65–2.83 (3H, m), 2.34 (3H, m), 2.10 (1H, m), 1.98 (2H, m), 1.68 (2H, m), 1.18 (3H, d), 1.06 (3H, d).

Example 3 m/z: 518 (MH+)

$R_f$: 0.29 dichloromethane/methanol/ammonium hydroxide (80/20/3) $\delta_H$ (300 MHz, CDCl$_3$): 7.94 (1H, s), 7.54 (4H, m), 7.24 (1H, m), 6.85 (3H, m), 5.91 (1H, m), 5.10–5.34 (3H, m), 4.28 (2H, t), 3.78 (3H, s), 3.50 (1H, m), 3.17 (1H, m), 2.73–3.02 (4H, m), 2.40 (1H, m), 2.26 (3H, m), 1.85 (2H, m), 1.58 (2H, m), 1.17 (6H, 2xd).

Example 4

2-(3-{4-[(R)-1-[(2S,5R)-4-allyl-2,5-dimethylhexahydropyrazin-1-yl]-1-(3-hydroxyphenyl)methyl]phenyl}-1H-1,2,4-triazol-1-yl)acetic acid

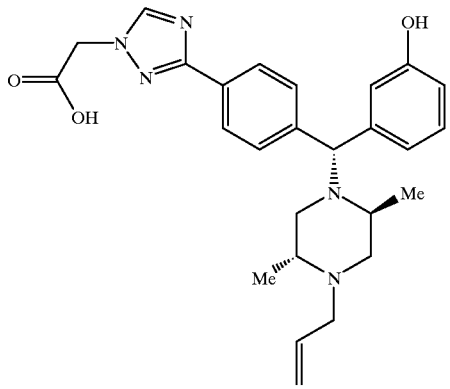

Boron tribromide (2 ml, 1N solution in dichloromethane) was added to a solution of the compound from Example 1 (95 mg) and the reaction stirred at room temperature under a nitrogen atmosphere for 3 hours. The reaction mixture was evaporated to dryness in vacuo and the residue azeotroped with dichloromethane. This material was neutralised with 80/20/3 dichloromethane/methanol/ammonium hydroxide solution and re-evaporated to dryness. The residue was purified by column chromatography over silica gel (80/20/3 dichloromethane/methanol/ammonium hydroxide) to afford the title compound, as a colorless solid, 63 mg.

$R_f$: 0.17 (80/20/3 dichloromethane/methanol/ammonium hydroxide)

m/z: 462 (MH+)

$\delta_H$ (300 MHz, CDCl$_3$): 8.15 (1H, s), 7.86 (2H, d), 7.12 (3H, m), 6.76 (2H, m), 6.54 (1H, d), 5.82 (1H, m), 5.37 (2H, 2xd), 5.06 (1H, s), 4.68 (2H, s), 3.60 (1H, dd), 3.30 (2H, m), 3.04 (1H, d), 2.76 (1H, m), 2.52 (1H, m), 2.40 (1H, dd), 2.20 (2H, m), 1.02 (3H, d), 0.85 (3H, d).

Examples 5 and 6

5-(5-{4-[(R)-1-[(2S,5R)-4-allyl-2,5-dimethylhexahydropyrazin-1-yl]-1-(3-hydroxyphenyl)methyl]phenyl}-1H-1,2,4-triazol-1-yl)pentanoic acid and 5-(5-{4-[(R)-1-[(2S,5R)-4-allyl-2,5-dimethylhexahydropyrazin-1-yl]-1-(3-hydroxyphenyl)methyl]phenyl}-2H-1,2,4-triazol-1-yl)pentanoic acid The following compounds of the general formula:

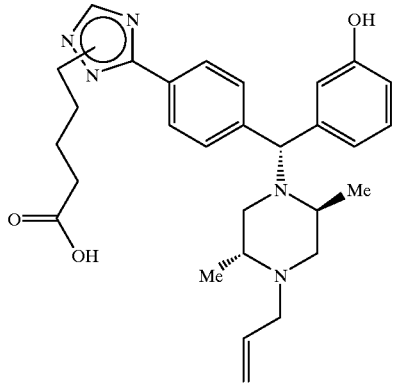

or salts thereof, were prepared from the corresponding methyl ethers (Example 2 and 3) by similar methods to that used in Example 4.

| Ex | Isomer | M/z | 1H-nmr/Analysis |
|---|---|---|---|
| 5 | 1 | 504 | $\delta_H$ (300 MHz, CDCl$_3$): 7.94 (1H, s), 7.50 (4H, m), 7.13 (1H, dd), 6.71 (3H, m), 5.90 (1H, m), 5.24 (2H, m), 5.18 (1H, s), 4.11 (2H, t), 3.48 (1H, dd), 3.11 (1H, dd), 2.95 (1H, d), 2.80 (2H, m), 2.64 (1H, d), 2.34 (1H, dd), 2.20 (1H, dd), 2.10 (2H, t), 1.84 (2H, m), 1.49 (2H, m), 1.10 (6H, 2xd). |
| 6 | 2 | 504 | $\delta_H$ (300 MHz, CDCl$_3$): 8.05 (1H, s), 7.84 (2H, d), 7.36 (2H, s), 7.03 (1H, dd), 6.65 (2H, m), 6.58 (1H, d), 5.67 (1H, m), 5.12 (3H, m), 4.10 (2H, t), 3.30 ( ), 2.94 (1H, d), 2.80 (1H, d), 2.65 (1H, m), 2.53 (2H, m), 2.19 (3H, m), 2.02 (1H, m), 1.88 (2H, m), 1.55 (2H, m), 1.06 (3H, d), 0.92 (3H, d). |

| Ex | Isomer | M/z | ¹H-nmr/Analysis |
|---|---|---|---|
| | | | Found: C, 66.06; H, 7.59; N, 13.58. $C_{29}H_{37}N_5O_3 \cdot 6/5H_2O$ requires C, 66.31; H, 7.56; N, 13.33% |

Example 5

(5-{4-[(R)-1-[(2S,5R)-4-allyl-2,5-dimethylhexahydropyrazin-1-yl]-1-(3-hydroxyphenyl)methyl]phenyl}-1H-1,2,4-triazol-1-yl)pentanoic acid

Example 6

(5-{4-[(R)-1-[(2S,5R)-4-allyl-2,5-dimethylhexahydropyrazin-1-yl]-1-(3-hydroxyphenyl)methyl]phenyl}-2H-1,2,4-triazol-1-yl)pentanoic acid

Examples 7 and 8

Ethyl 5-(5-{4-[(R)-1-[(2S,5R)-4-benzyl-2,5-dimethylhexahydropyrazin-1-yl]-1-(3-methoxyphenyl)methyl]phenyl}-2H-1,2,4-triazol-1-yl)pentanoate and Ethyl 5-(5-{4-[(R)-1-[(2S,5R)-4-benzyl-2,5-dimethylhexahydropyrazin-1-yl]-1-(3-methoxyphenyl)methyl]phenyl}-1H-1,2,4-triazol-1-yl)pentanoate

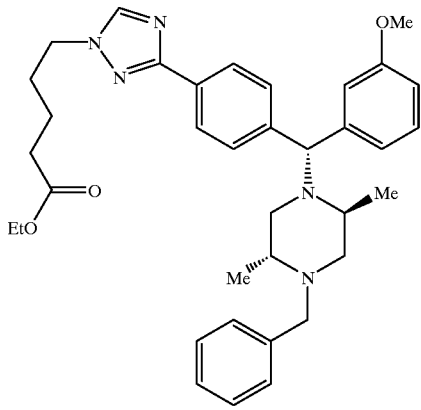

-continued

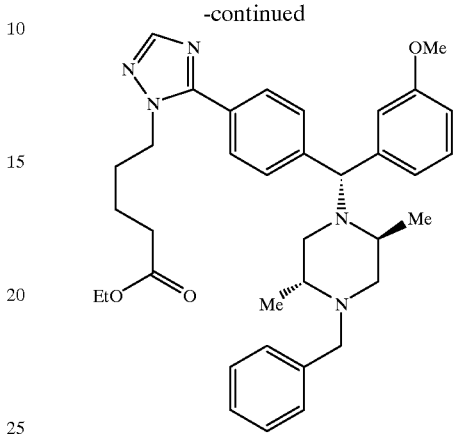

A suspension of the compound from Preparation 10 (490 mg), ethyl 5-bromovalerate (182 µl) and potassium carbonate (434 mg) in acetonitrile (20 ml) was stirred under reflux for 72 hours. On cooling, the mixture was partitioned between water (25 ml) and dichloromethane (150 ml) and the layers separated. The organic phase was dried ($MgSO_4$) and evaporated to dryness in vacuo. The residue was purified by column chromatography over silica gel using gradient elution (98/2–90/10 dichloromethane/methanol) and then again eluting with (95/5/0.25–80/20/1.5 hexane/isopropanol/ammonium hydroxide) to afford the N2 isomer, 490 mg.

$R_f$ : 0.50 (90/10/0.75 hexane/isopropanol/ammonium hydroxide)

m/z: 596 ($MH^+$)

$\delta_H$ (300 MHz, $CDCl_3$): 8.07 (1H, s), 8.00 (2H, d), 7.52 (2H, d), 7.20–7.32 (6H, m), 6.82 (3H, m), 5.12 (1H, s), 4.20 (2H, t), 4.14 (2H, q), 3.90 (1H, d), 3.22 (1H, d) 2.55–2.76 (4H, m), 2.36 (2H, t), 1.95–2.06 (4H, m), 1.57–1.74 (4H, m), 1.22 (3H, t), 1.10 (6H, 2xd).

and the N1 isomer, 35 mg.

$R_f$ : 0.40 (90/10/0.75 hexane/isopropanol/ammonium hydroxide)

m/z: 596 ($MH^+$)

$\delta_H$ (300MHz, $CDCl_3$): 7.95 (1H, s), 7.60 (2H, d), 7.52 (2H, d), 7.28 (6H, m), 6.81 (3H, m), 5.16 (1H, s), 4.21 (2H, t), 4.10 (2H, q), 3.92 (1H, d), 3.80 (3H, s), 3.20(1H, d), 2.56–2.77 (4H, m), 2.29 (2H, t), 1.89–2.06 (4H, m), 1.62 (2H, m), 1.24 (3H, t),1.12 (6H, 2xd).

Examples 9 and 10

5-(5-{4-[(R)-1-[(2S,5R)-4-benzyl-2,5-dimethylhexahydropyrazin-1-yl]-1-(3-methoxyphenyl)methyl]phenyl}-1H-1,2,4-triazol-1-yl)pentanoic acid

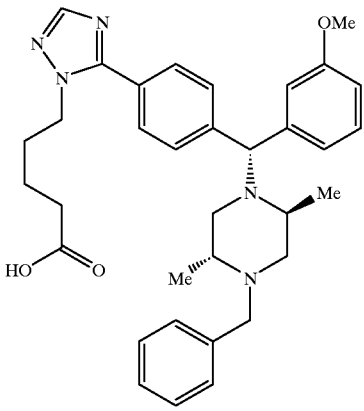

5-(5-{4-[(R)-1[(2S,5R)-4-benzyl-2,5-dimethylhexahydropyrazin-1-yl]-1-(3-methoxyphenyl)methyl]phenyl}-2H-1,2,4-triazol-1-yl)pentanoic acid

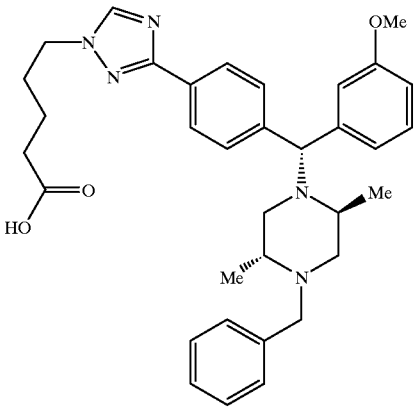

These compounds were prepared by a method similar to that described for Example 1 using the compound of Preparation 10 and ethyl-5-bromovalerate and subsequent saponification.

The results were as follows:

N1 isomer m/z: 568 (MH⁺)

$\delta_H$(300 MHz, CDCl₃): 7.93 (1H, s), 7.53 (2H, d), 7.46 (2H, d), 7.18–7.28 (5H, m), 7.12 (1H, dd), 6.68 (2H, m), 6.56 (1H, s), 5.07 (1H, s), 4.20 (2H, t), 3.93 (1H, d), 3.60 (3H, s), 3.17 (1H, d), 2.68 (1H, d), 2.57 (3H, m), 2.22 (2H, t), 1.84–2.02 (4H, m), 1.556 (2H, m), 1.08 (3H, d), 1.02 (3H, d).

N2 isomer, m/z: 568 (MH⁺)

$\delta_H$ (300 MHz, CDCl₃): 8.07 (1H, s), 7.97 (2H, d), 7.48 (2H, d), 7.27 (5H, m), 7.13 (1H, dd), 6.72 (3H, m), 5.04 (1H, s), 4.18 (2H, t), 3.92 (1H, d), 3.67 (3H, s), 3.25 (1H, d), 2.55–2.74 (4H, m), 2.36 (2H, t), 1.94–2.10 (4H, m), 1.66 (2H, m), 1.10 (3H, d), 1.02 (3H, d).

Example 11

5-(5-{4-[(R)-1-[(2S,5R)-4-benzyl-2,5-dimethylhexahydropyrazin-1-yl]-1-(3-hydroxyphenyl)methyl]phenyl}-1H-1,2,4-triazol-1-yl)pentanoic acid

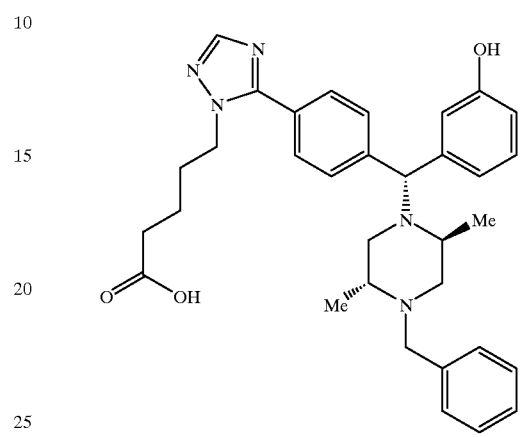

The title compound was prepared using the compound from Example 9 following a similar method to that used in Example 4.

m/z: 554 (MH⁺)

$\delta_H$ (400 MHz, CDCl₃): 7.90 (1H, s), 7.54 (2H, d), 7.45 (2H, d), 7.19–7.28 (5H, m), 7.12 (1H, dd), 6.72 (2H, m), 6.52 (1H, s), 5.12 (1H, s), 4.22 (2H, t), 3.93 (1H, d), 3.19 (1H, d), 2.55–2.72 (4H, m), 1.92–2.10 (4H, m), 1.82 (2H, m), 1.47 (2H, m), 1.06 (6H, 2xd).

Example 12

5-(5-{4-[(R)-1-[(2S, 5R)-4-benzyl-2,5-dimethylhexahydropyrazin-1-yl]-1-(3-hydroxyphenyl)methyl]phenyl}-2H-1,2,4-triazol-1-yl)pentanoic acid

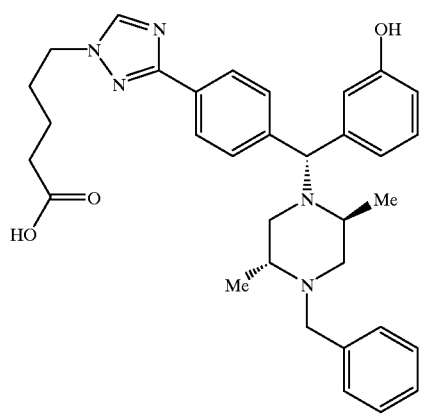

The title compound was prepared using the compound from Example 10 following the procedure described in Example 4.

$\delta_H$ (400 MHz, CD₃OD): 8.45 (1H, s), 7.90 (2H, d), 7.46 (2H, d), 7.30 (5H, m) 7.15 (1H, dd), 6.69 (3H, m), 5.16 (1H, s), 4.22 (2H, t), 4.12 (1H, d), 3.52 (1H, d), 2.80 (3H, m), 2.64 (1H, m), 2.26 (3H, m), 2.10 (1H, m), 1.92 (2H, m), 1.60 (2H, m), 1.21 (3H, d), 1.11 (3H, d).

Examples 13 and 14

Ethyl 5-(4-{4-[(R)-1-[(2S,5R)-4-benzyl-2,5-dimethylhexahydropyrazin-1-yl]-1-(3-hydroxyphenyl)methyl]phenyl}-1H-1,2,3-triazol-1-yl)pentanoate and Ethyl 5-(4-{4-[(R)-1-[(2S,5R)-4-benzyl-2,5-dimethylhexahydropyrazin-1-yl]-1-(3-hydroxyphenyl)methyl]phenyl}-2H-1,2,3-triazol-2-yl)pentanoate

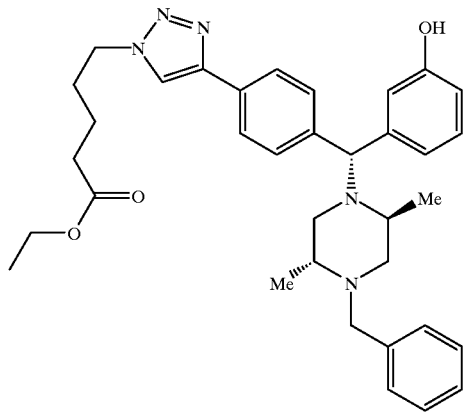

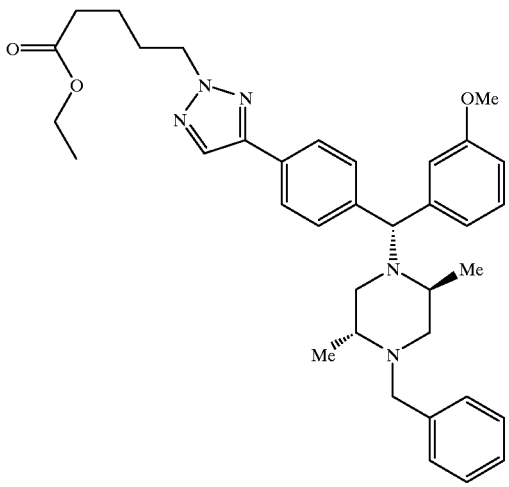

A suspension of the compound from Preparation 16 (573 mg), ethyl 5-bromovalerate (162 μl), and potassium carbonate (418 mg) in acetonitrile (15 ml) was stirred under reflux for 18 hours. On cooling, the mixture was partitioned between aqueous ammonium chloride solution and ethyl acetate. The phases were separated, and the aqueous layer extracted with ethyl acetate. The combined organic extracts were dried (MgSO$_4$) and evaporated in vacuo to give a brown oil. This material was purified by column chromatography over silica gel using gradient elution (90/10–50/50 pentane/ethyl acetate) to afford the N2 isomer, 172 mg.

m/z: 582 (MH$^+$)

$\delta_H$ (400 MHz, CDCl$_3$): 7.75 (1H, s), 7.64 (2H, d), 7.45 (2H, d), 7.08–7.28 (6H, m), 6.74 (1H, d), 6.62 (2H, m), 5.04 (1H, s), 4.41 (2H, t), 4.08 (2H, q), 3.89 (1H, d), 3.18 (1H, d), 2.52–2.70 (4H, m), 2.30 (2H, t), 1.99 (4H, m), 1.63 (2H, m), 1.20 (3H, t), 1.08 (3H, d), 1.02 (3H, d).

followed by the N1 isomer, 141 mg.

m/z: 582 (MH$^+$)

$\delta_H$ (400 MHz, CDCl$_3$): 7.70 (3H, m), 7.46 (2H, d), 7.10–7.30 (7H, m), 6.74 (1H, d), 6.66 (2H, m), 5.02 (1H, s), 4.38 (2H, t), 4.10 (2H, q), 3.88 (1H, d), 3.18 (1H, d) 2.50–2.70 (4H, m), 2.30 (2H, t), 2.00 (4H, m), 1.65 (2H, m), 1.21 (3H, t), 1.06 (6H, 2xd).

Examples 15 to 19

The compounds of the following general formula:

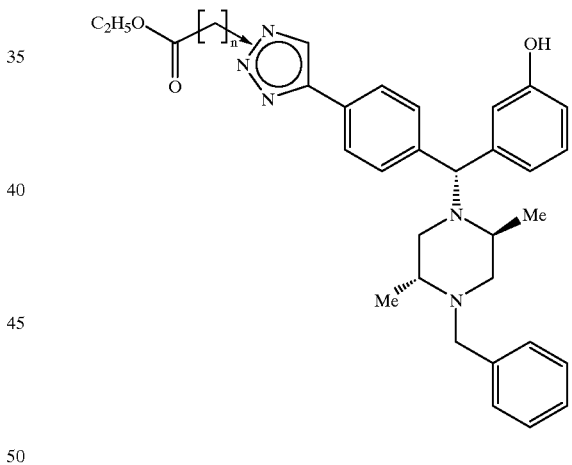

were prepared by a similar method to that described for Examples 13 and 14 using the compound of Preparation 16 and the corresponding omega-bromoesters.

| Ex | Isomer | M/z | n | $^1$H nmr/analysis |
|---|---|---|---|---|
| 15 | N-1 | | 1 | $\delta_H$ (400 MHz, DMSO-d$_6$): Found: C, 66.64; H, 6.70; N, 12.94. C$_{30}$H$_{33}$N$_5$O$_3$1.6 H$_2$O requires C, 66.61; H, 6.65; N, 12.92% |
| 16 | N-2 | | 1 | |
| 17 | N-2 | 554 | 2 | δ (CDCl$_3$): 7.80 (1H, s), 7.68 (2H, d), 7.50 (2H, d), 7.36–7.10 (6H, m), 6.80–6.60 (3H, m), 5.07 (1H, s), 4.74 (2H, t), 4.20 (2H, q), 3.96 (1H, d), 3.20 (1H, d), 3.02 (2H, m), 2.78–2.50 (4H, m), |

-continued

| Ex | Isomer | M/z | n | $^1$H nmr/analysis |
|---|---|---|---|---|
| | | | | 2.00 (3H, m), 1.25 (3H, t), 1.10 (3H, d), 1.05 (3H, m). |
| 18 | N-1 | 569 | 3 | δ (CDCl$_3$): 7.73 (3H, m), 7.49 (2H, d), 7.35–7.10 (6H, m), 6.85–6.65 (3H, m), 5.52 (1H, br s), 5.07 (1H, s), 4.47 (2H, t), 4.13 (2H, q), 3.92 (1H, d), 3.22 (1H, d), 2.80–2.55 (4H, m), 2.40–2.20 (4H, m), 2.10–1.95 (2H, m), 1.26 (3H, t), 1.15–1.05 (6H, m). [α]$_D$ 740 (c = 0.1) m/z 569 |
| 19 | N-2 | 569 | 3 | δ (CDCl$_3$): 7.79 (1H, s), 7.68 (2H, d), 7.49 (2H, d), 7.35–7.10 (6H, m), 6.85–6.65 (3H, m), 5.07 (1H, br s), 5.02 (1H, br s), 4.52 (2H, t), 4.13 (2H, q), 3.91 (1H, d), 3.22 (1H, d), 2.80–2.50 (4H, m), 2.40–2.25 (4H, m), 2.10–1.95 (2H, m), 1.25 (3H, t). 1.09 (6H, m). [α]$_D$ −10.4° (c = 0.1) m/z 569 |

Examples 20 and 21

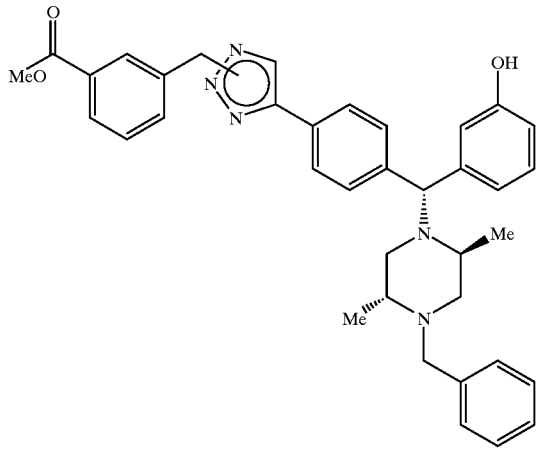

To a solution of the compound from Preparation 16 (2.4 g) in acetonitrile (60 ml) was added methyl 3-bromomethylbenzoate (0.969 g) and potassium carbonate (1.75 g). The reaction mixture was heated to reflux for 16 hrs, after which time the reaction mixture was cooled to room temperature and tetraethyl ammonium fluoride (2.2 g) was added, the reaction mixture was stirred for 25 mins and then evaporated under reduced pressure. The residue was treated with sodium bicarbonate solution (1% 80 ml), and the product extracted with EtOAc (×2). The combined organic layers were dried over MgSO$_4$, and evaporated under reduced pressure. The crude product was purified on silica gel eluting with EtOAc/hexane (1:3–1:1) to afford the title compounds as two isomers.

N2 isomer as a white foam (1.15 g):

R$_f$ 0.15 (EtOAc/hexane, 1/3, v/v).

δ$_H$ (CDCl$_3$) 8.05 (1H, s), 8.00 (1H, d), 7.80 (1H, s), 7.65 (2H, d), 7.55–7.40 (4H, m), 7.3–7.1 (6H, m), 6.80–6.60 (3H, m), 5.65 (2H, s), 5.05 (1H, s), 3.90 (4H, t), 3.20 (1H, d), 2.80–2.50 (4H, m) 2.10–1.95 (2H, m), 1.10 (6H, 2xd).

N1 isomer as a beige foam (1.0 g):

R$_f$ 0.25 (EtOAc/hexane, 1/3, v/v).

δ$_H$ (CDCl$_3$) 8.05 (1H, s), 8.00 (1H, d), 7.70 (2H, d), 7.65 (1H, s), 7.55–7.40 (4H, m), 7.3–7.1 (6H, m), 6.80–6.60 (3H, m), 5.65 (2H, s), 5.05 (1H, s), 3.95 (4H, d), 3.20 (1H, d), 2.80–2.50 (4H, m), 2.10–1.95 (2H, m), 1.10 (6H, 2xd).

Example 22

(−)-2-(4-{4-[(R)-1-[(2S,5R)-4-benzyl-2,5-dimethylhexahydropyrazin-1-yl]-1-(3-hydroxyphenyl)methyl]phenyl}-1H-1,2,3-triazol-1-yl)acetic acid

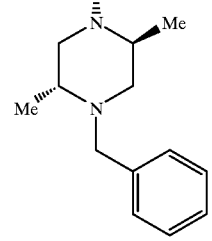

Aqueous sodium hydroxide solution (0.5 ml, 2N) was added to a solution of the compound of Example 15 (152 mg), in dioxan (6 ml) and methanol (3 ml) and the reaction stirred at room temperature for 1 hour. The reaction mixture was acidified to pH 5 using 2N hydrochloric acid then evaporated to dryness in vacuo. The residue was purified by column chromatography over silica get using gradient elution (85/15/3–80/20/4, dichloromethane/methanol/ammonium hydroxide). This material was further purified on a polystyrene reverse phase resin using gradient elution (100/0–60/40 water/acetonitrile). The acetonitrile was evaporated in vacuo and the remaining aqueous solution was frozen and lyophilised to afford the title compound, 55 mg.

m/z: 512 (MH$^+$)

δ$_H$ (400 MHz, DMSO-d$_6$): 9.25 (1H,s), 8.40 (1H, s), 7.73 (2H, d), 7.40 (2H, d), 7.25–7.05 (6H, m), 6.70 (2H m), 6.60 (1H, d), 5.10 ( 2H, s), 4.85 (1H, s), 3.75 (1H, d), 2.70–2.50 (4H, m), 2.28 (1H, s), 2.0 (2H, m), 1.0 (6H, 2xd).

Found: C, 65.28; H, 6.84; N, 13.04. C$_{30}$H$_{33}$N$_5$O$_3$. 2.1 H$_2$O requires C, 64.98; H, 6.86; N, 13.33%

[α]$_D$ –5.46 (methanol, c=0.33)

Examples 23 to 27

The following compounds of the general formula:

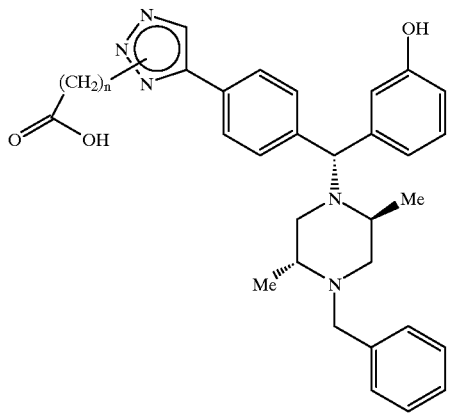

were prepared using the procedure described in Example 22 from the corresponding esters.

Example 23

(−)-2-(4-{4-[(R)-1-[(2S,5R)-4-benzyl-2,5-dimethylhexahydropyrazin-1yl]-1-(3-hydroxyphenyl)methyl]phenyl}-2H-1,2,3-triazol-2-yl)acetic acid Example 24

3-(4-{4-[(R)-1-[(2S,5R)-4-benzyl-2,5-dimethylhexahydropyrazin-1-yl]-1-(3-hydroxyphenyl)methyl]phenyl}-2H-1,2,3-triazol-2-yl)propanoic acid Example 25

4-(4-{4-[(R)-1-[(2S,5R)-4-benzyl-2,5-dimethylhexahydropyrazin-1-yl]-1-(3-hydroxyphenyl)methyl]phenyl}-1H-1,2,3-triazol-2-yl)butanoic acid Example 26

(−)-5-(4-{4-[(R)-1-[(2S,5R)-4-benzyl-2,5-dimethylhexahydropyrazin-1-yl]-1-(3-hydroxyphenyl)methyl]phenyl}-1H-1,2,3-triazol-2-yl)pentanoic acid Example 27

(−)-5-(4-{4-[(R)-1-[(2S,5R)-4-benzyl-2,5-dimethylhexahydropyrazin-1-yl]-1-(3-hydroxyphenyl) methyl]phenyl}-2H-1,2,3-triazol-2-yl)pentanoic acid

| Ex | Isomer | M/z | n | [α]$_D$ MeOH (C = 0.1) | $^1$H nmr |
|---|---|---|---|---|---|
| 23 | 2 | 512 | 1 | −3.20° | δ$_H$ (400 MHz, DMSO-d$_6$): 9.25 (1H, s), 8.20 (1H, s), 7.72 (2H, d). 7.40 (2H, d), 7.30–7.05 (6H, m), 6.70 (2H, m), 6.60 (1H, d), 5.20 (2H, s), 4.85 (1H, s0, 3.71 (1H, d), 2.70–2.50 (4H, m), 2.27 (1H, s), 2.05–1.95 (2H, m), 1.0 (6H, 2xd). Found: C, 66.64; H, 6.70; N, 12.94. C$_{30}$H$_{33}$N$_5$O$_3$.1.6 H$_2$O requires C, 66.61; H, 6.65; N, 12.92% |
| 24 | 2 | 526 | 2 | −5.20° | δ$_H$ (300 MHz, DMSO-d$_6$): 8.10 (1H, s), 7.75 (2H, d), 7.45 (2H, d), 7.30–7.05 (6H, m), 6.80–6.60 (3H, m), 4.90 (1H, s), 4.60 (2H, t), 3.85 (1H, d), 3.0 (1H, m), 2.95 (2H, t), 2.75–2.55 (4H, m), 2.0 (2H, m), 1.0 (6H, 2xd). Found: C, 65.41; H, 6.85; N, 12.80, C$_{31}$H$_{35}$N$_5$O$_3$.2.25 H$_2$O requires C, 65.76; H, 7.03; N, 12.37% |
| 25 | 1 | 540 | 3 | | δ$_H$ (400 MHz, DMSO-d$_6$): 8.48 (1H, s), 7.73 (2H, d), 7.43 (2H, d), 7.30–7.05 (6H, m), 6.80–6.60 (3H, m), 4.88 (1H, s), 4.40 (2H, t), 3.70 (1H, d), 3.25 (1H, d), 2.70–2.50 (4H, m), 2.20 (2H, t), 2.10–1.90 (4H, m), 1.03 (6H, m). Found C, 67.82; H, 7.09; N, 13.12. C$_{32}$H$_{37}$N$_5$O$_3$.1.5 H$_2$O requires C, 67.82; H, 7.11; N 12.36% |
| 26 | 1 | 554 | 4 | −5.40° | δ$_H$ (300 MHz, DMSO-d$_6$): 8.48 (1H, s), 7.74 (2H, d), 7.42 (2H, d), 7.26 (4H, m), 7.19 (1H, m), 7.10 (1H, dd), 6.72 (2H, d), 6.62 (1H, d), 4.88 (1H, s), 4.37 (2H, t), 3.73 (1H, d), 2.57–2.72 (4H, m), 2.44 (5H, m), 2.22 (2H, t), 2.00 (2H, m), 1.86 (2H, m), 1.46 (2H, m), 1.04 (6H, 2xd). Found: C, 67.64; H, 7.12; N, 11.84. C$_{33}$H$_{39}$N$_5$O$_3$.7/4 H$_2$O requires C, 67.73; H, 7.32; N, 11.97% |
| 27 | 2 | 554 | 4 | −6.20° | δ$_H$ (300 MHz, DMSO-d$_6$): 8.14 (1H, s), 7.74 (2H, d), 7.45 (2H, d), 7.27 (4H, m), 7.19 (1H, m), 7.10 (1H, dd), 6.60–6.74 (3H, m), 4.90 (1H, s), 4.41 (2H, t), 3.72 (1H, d), 2.63 (4H, m). 2.42 (4H, m), 2.18 (2H, t), 1.82–2.05 (5H, m), 1.45 (2H, m), 1.04 (6H, 2xd). |

| Ex | Isomer | M/z | n | [α]$_D$ MeOH (C = 0.1) | $^1$H nmr |
|---|---|---|---|---|---|

Found: C, 68.92; H, 7.17; N, 12.27. $C_{33}H_{39}N_5O_3 \cdot H_2O$ requires C, 69.33; H, 7.23; N, 12.25%

Example 28 and 29

3-[(4-{4-[(R)-1-[(2S,5R)-4-benzyl-2,5-(dimethylhexahydropyrazin-1-yl]-1-(3-hydroxyphenyl)methyl]phenyl}-2H-1,2,3-triazol-2-yl)methyl]benzoic acid and 3-[(4-{4-[(R)-1-[(2S,5R)-4-benzyl-2,5-dimethylhexahydropyrazin-1-yl]-1-(3-hydroxyphenyl)methyl]phenyl}-1H-1,2,3-triazol-2-yl)methyl]benzoic acid The following compounds of the formula:

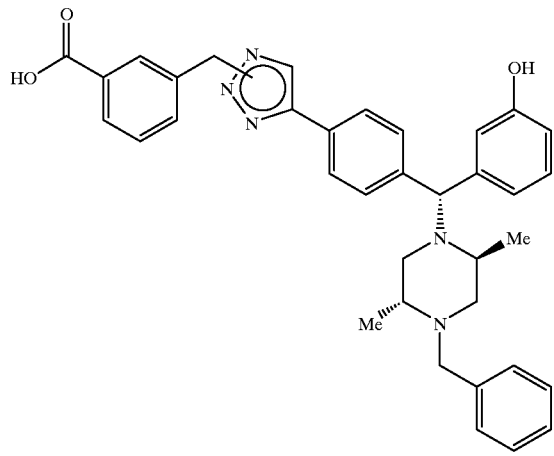

were prepared from Examples 20 and 21 following the procedure described in Example 22.

Example 30

2-[2-(4-{4-[(R)-1-[(2S,5R)-4-benzyl-2,5-dimethylhexahydropyrazin-1-yl]1(3-hydroxyphenyl)methyl]phenyl}-2H-1,2,3-triazol-2-yl)ethoxy]acetic acid

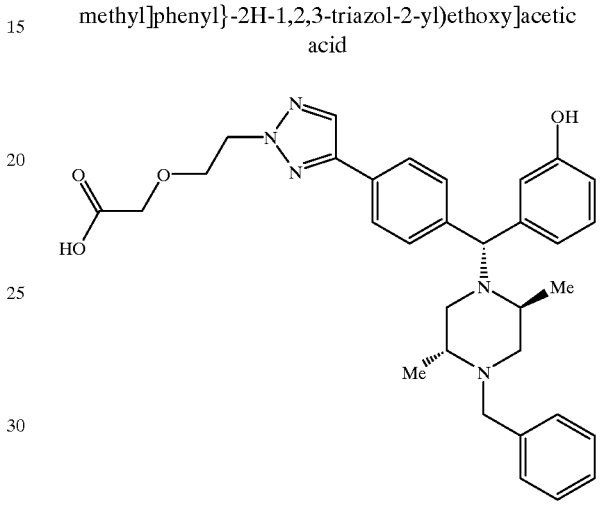

Hydrogen chloride gas was bubbled through a solution of the first compound of Preparation 17 (2.50 g) in ethanol (150 ml) at 0° C. for 30 mins. The reaction mixture was then stirred at 0° C. for 45 mins after which time the ethanol was evaporated under reduced pressure, the residue was redissolved in ethanol (60 ml) and $H_2O$ (60 ml), warmed to room temperature and stirred for 18 hrs. 2M NaOH (11.5 ml) was added to the reaction mixture and stirred for 3 hrs, the

| Ex | Isomer | M/z | $^1$H-nmr |
|---|---|---|---|
| 28 | 2 | 588 | δ$_H$ (400 MHz, DMSO-d$_6$): 8.55 (1H, s), 7.85 (2H, d), 7.75 (2H, m), 7.45 (4H, m), 7.25 (4H. m), 7.20 (1H, m), 7.10 (1H, t), 6.80–6.60 (3H, m), 5.80–5.60 (2H, 2xs), 4.95 (1H, s), 3.75 (1H, d), 2.70–2.50 (4H, m), 2.0 (2H, m), 1.05 (6H, m). Found: C, 52.00; H, 7.34: N, 8.37. $C_{36}H_{37}N_{51\ O3}\cdot 3.5$ H$_2$O requires C, 52.03; H, 7.76; N, 8.43% |
| 29 | 1 | 588 | δ$_H$ (400 MHz, DMSO-d$_6$): 8.25 (1H, s), 7.85 (2H, m), 7.75 (2H, m), 7.45 (4H, m), 7.25 (4H, m), 7.20 (1H, m), 7.10 (1H, t), 6.80–6.60 (3H, m), 5.75 (2H, s), 4.95 (1H, s), 3.75 (1H, d), 2.70–2.50 (4H, m), 2.0 (2H, m), 1.05 (6H, 2xd). Found: C, 69.77; H, 6.31, N, 11.14. $C_{36}H_{37}N_5O_3 \cdot 1.8$ H$_2$O requires C, 69.72 H, 6.60; N, 1.29%. | mixture was acidified to pH 5 using 2M HCl and the solvent evaporated under reduced pressure. The product was purified on silica gel eluting with ($CH_2Cl_2$/MeOH/0.88NH$_3$, 80/20/4, v/v) to afford the N2 isomer (1.60 g) as a white powder.

m/z: 556 (MH$^+$)

δ$_H$ (300 MHz, DMSO-d$_6$): 8.20 (1H, s), 7.80 (2H, d), 7.45 (2H, d), 7.30 (4H, m), 7.25 (1H, m), 7.10 (1H, t), 6.80–6.60 (3H, m), 4.95 (1H, s), 4.55 (2H, t), 3.95 (2H, d), 3.85 (2H, m), 3.70 (1H, d), 2.70–2.50 (4H, m), 2.0 (2H, m), 1.05 (6H, m).

Found: c, 66.63; H, 6.84; N, 12.64. C$_{32}$H$_{37}$N$_5$O$_4$.$_{H2}$O requires C, 66.99; H, 6.85; N, 12.21%

[α]$_D$ −2.0 (Methanol, c=0.1)

Example 31

2-[2-(4-{4-[(R)-1-[(2S,5R)-4-benzyl-2,5-dimethylhexahydropyrazin-1-yl]-1-(3-hydroxyphenyl)methyl]phenyl}-1H-1,2,3-triazol-2-yl) ethoxy]acetic acid The compound of the formula:

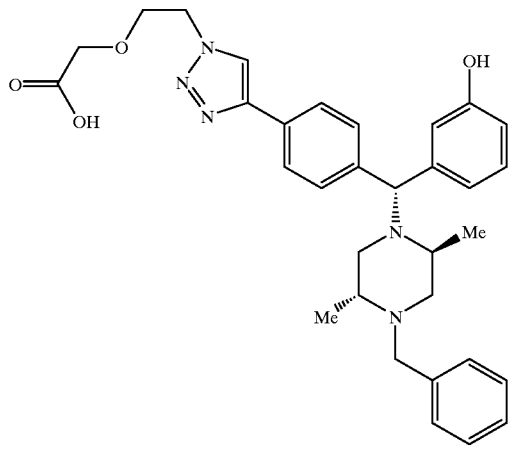

was prepared using a similar method to Example 30 and using the second compound of Preparation 17, to afford the title compound as a white solid (490 mg).

m/z: 556 (MH$^+$)

δ$_H$ (300 MHz, DMSO-d$_6$): 8.70 (1H, s), 7.75 (2H, d), 7.45 (2H, d), 7.30 (4H, m), 7.20 (1H, m), 7.10 (1H, t), 6.80–6.60 (3H, m), 4.95 (1H, s), 4.50 (2H, m), 3.95–3.70 (6H, m), 2.70–2.50 (4H, m), 2.0 (2H, m), 1.05 (6H, 2xd).

Found: c, 64.33; H, 7.02; N, 13.08. C$_{32}$H$_{37}$N$_5$O$_4$. 2.25 H$_2$O requires C, 64.46; H, 7.02; N, 11.75%.

[α]$_D$ −2.60 (methanol, c=0.1)

Example 32

Example 33

Ethyl 2-(3-{4-[(R)-1-[(2S,5R)-4-allyl-2,5-dimethylhexahydropyrazin-1-yl]-1-(3-hydroxyphenyl)methyl]phenyl}-1,2,4-oxadiazol-5-yl)acetate

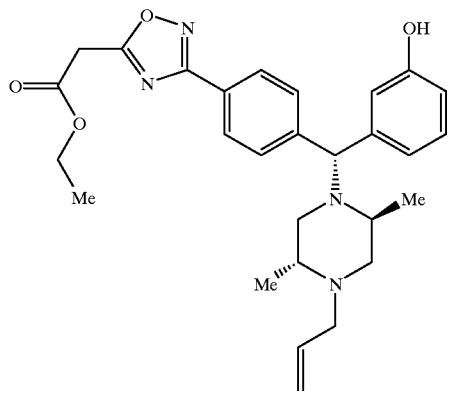

Tetrabutylammonium hydrogen sulphate (50 mg) and powdered sodium hydroxide (508 mg) were added to a solution of the compound from Preparation 19 (1 g). A solution of freshly distilled ethyl malonyl chloride (704 ml) in dioxan (5 ml ) was then added dropwise to this solution and the reaction stirred at 70° C. for 20 hours. On cooling, the reaction mixture was filtered and the filtrate evaporated to dryness in vacuo, to give a brown oil. The residue was purified by column chromatography over silica gel using gradient elution (93/7/0.5–80/20/3 hexane/isopropyl alcohol/ammonium hydroxide) to afford the title compound, 485 mg.

R$_f$: 0.37 (80/20/1.5 hexane/isopropanol/ammonium hydroxide).

m/z: 491 (MH$^+$)

δ$_H$ (300 MHz, CDCl$_3$): 7.99 (2H, d), 7.55 (2H, d), 7.18 (1H, dd), 6.72 (2H, m), 6.62 (1H, s), 5.88 (1H, m), 5.19 (3H, m), 4.26 (2H, q), 4.02 (2H, s), 3.38 (1H, dd) (2H, m), 2.48–2.68 (3H, m), 2.16 (1H, dd), 1.95 (1H, dd), 1.30 (3H, t), 1.20 (3H, d), 2.88 1.01 (3H, d).

Example 34

2-(3-{4-[(R)-1-[(2S,5R)-4-allyl-2,5-dimethylhexahydropyrazin-1-yl]-1-(3-hydroxyphenyl)methyl]phenyl}-1,2,4-oxadiazol-5-yl)acetic acid

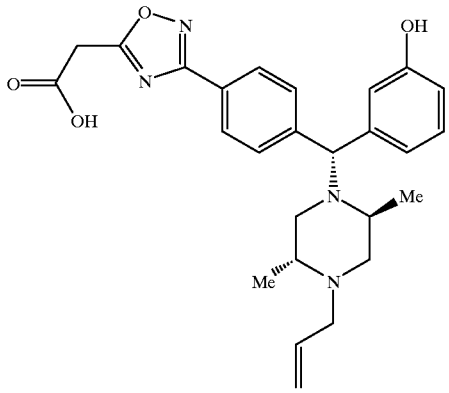

A solution of the compound from Example 33 (490 mg) in acetone (45 ml) was added to a suspension of lipase enzyme (Pseudomonas cepacia), (150 mg) in phosphate buffer (pH 7.2, 0.2M, 80 ml), and the reaction stirred at room temperature for 18 hours. Lipase P (Amano) enzyme (200 mg) was then added and the reaction stirred at 30° C. for a further 3 weeks. The reaction mixture was preadsorbed onto coarse grade silica gel and evaporated to dryness in vacuo. The residue was purified by column chromatography over silica gel (80/20/3 dichloromethane/methanol/ammonium hydroxide). This material was further purified over a polystyrene reverse phase resin using gradient elution (90/10–50/50 water/acetonitrile). The acetonitrile was evaporated in vacuo and the remaining aqueous solution was frozen and lyophilised to afford the title compound as a white solid, 63 mg.

$R_f$: 0.31 (80/20/3 dichloromethane/methanol/ammonium hydroxide)

$\delta_H$ (400 MHz, DMSO-$d_6$): 9.38 (1H, br s), 7.94 (2H, d), 7.58 (2H, d), 7.16 (1H, m), 6.68 (2H, m), 5.82 (1H, m), 5.20 (2H, 2xd), 5.08 (1H, s), 4.19 (2H, s), 3.02 (1H, dd), 2.87 (1H, d), 2.60–2.74 (3H, m), 2.28 (1H, m), 1.92 (1H, m), 1.12 (3H, d), 1.02 (3H, d).

Found: C, 61.80; H, 6.19; N, 11.19. $C_{26}H_{30}N_4O_2 \cdot 1/2H_2O$ requires C, 61.52; H, 6.95; N, 11.04

Example 35

3-((R)-1-[(2S,5R)-4-allyl-2,5-dimethylhexahydropyrazin-1-yl]-1-4-[4-(hydroxymethyl)-1,3-thiazol-2-yl]phenylmethyl)phenol

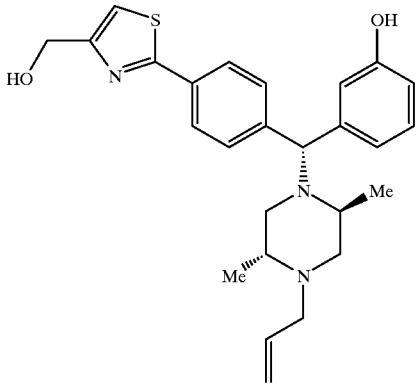

Tetraethylammonium fluoride (56 mg) was added to a solution of the compound from Preparation 26 (140 mg) in acetonitrile (10 ml) and the reaction stirred at room temperature for 30 minutes. The mixture was partitioned between ethyl acetate (20 ml) and water (10 ml) and the phases separated. The aqueous phase was extracted with ethyl acetate, the combined organic extracts dried ($Na_2SO_4$), and evaporated to dryness in vacuo. The residue was purified by column chromatography over silica gel (93/7/1 dichloromethane/methanol/ammonium hydroxide). This material was then slurried in water and this suspension frozen and lyophilised to afford the title compound as a solid, 73 mg.

$R_f$: 0.21 ((93/7/1 dichloromethane/methanol/ammonium hydroxide)

m/z: 450 (MH⁺)

$[\alpha]_D$ +29.21 (c=0.10 methanol)

$\delta_H$ (400 MHz, CDCl₃): 7.83 (2H, d), 7.49 (2H, d), 7.18 (1H, dd), 6.73 (2H, m), 6.65 (1H, s), 5.90 (1H, m), 5.20 (3H, m), 4.82 (2H, s), 3.40 (1H, dd), 2.94 (1H, m), 2.83 (1H, d), 2.60 (3H, m), 2.19 (1H, m), 2.00 (1H, m), 1.72 (1H, br s), 1.15 (3H, d), 1.02 (3H, d).

Found: C, 68.14; H, 7.06; N, 8.84. $C_{26}H_{31}N_3O_2S \cdot 2/5$ EtOAc requires C, 68.37; H, 7.11; N, 8.67

Example 36

3-((R)-1-[(2S,5R)-4-allyl-2,5-dimethylhexahydropyrazin-1-yl]-1-4-[4-(hydroxyethyl)-1,3-thiazol-2-yl]phenylmethyl)phenol

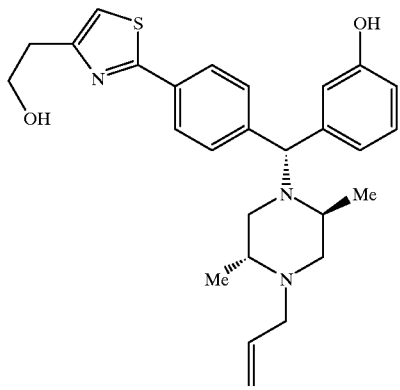

The title compound was prepared using the compound from Preparation 27 following a similar procedure to that described for Example 35, and was obtained in 95% yield.

$R_f$: 0.38 (90/10/2 dichloromethane/methanol/ammonium hydroxide)

m/z: 464 (MH$^+$)

$\delta_H$ (300 MHz, CDCl$_3$): 7.83 (2H, d), 7.49 (2H, d), 7.19 (1H, dd), 6.97 (1H, s), 6.72 (2H, m), 6.66 (1H, s), 5.88 (1H, m), 5.18 (3H, m), 3.99 (2H, t), 3.60 (1H, br s), 3.37 (1H, dd), 3.04 (2H, t), 2.86 (2H, m), 2.60 (2H, m), 2.48 (1H, m), 2.15 (1H, m), 1.94 (1H, m), 1.18 (3H, d), 0.99 (3H, d).

Example 37

Ethyl 2-{4-[(R)-1-[(2S,5R)-4-allyl-2,5-dimethylhexahydropyrazin-1-yl]-1-(3-hydroxyphenyl)methyl]phenyl}-1,3-thiazole-4-carboxylate

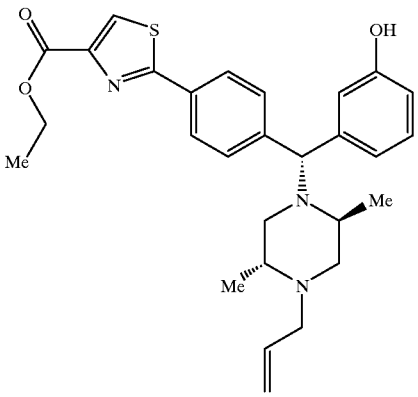

Tetraethylammonium fluoride (296 mg) was added to a solution of the compound from Preparation 24 (800 mg), in acetonitrile (10 ml), and the reaction stirred at room acetate, and the phases separated. The aqueous layer was extracted with ethyl acetate, the combined organic extracts dried (Na$_2$SO$_4$) and evaporated to dryness in vacuo. The residue was purified by column chromatography over silica gel (96/4 dichloromethane/methanol) to afford the title compound, 580 mg.

m/z: 492 (MH$^+$)

$\delta_H$ (400 MHz, CDCl$_3$): 8.14 (1H, s), 7.93 (2H, s), 7.54 (2H, d), 7.20 (1H, dd), 6.74 (2H, m), 6.66 (1H, s), 5.88 (1H, m), 5.20 (3H, m), 4.46 (2H, q), 3.38 (1H, m), 2.87 (2H, m), 2.68 (1H, m), 2.60 (1H, d), 2.52 (1H, m), 2.17 (1H, m), 1.96 (1H, m), 1.43 (3H, t), 1.18 (3H, d), 1.01 (3H, d).

Examples 38 to 43

The following compounds of the general formula:

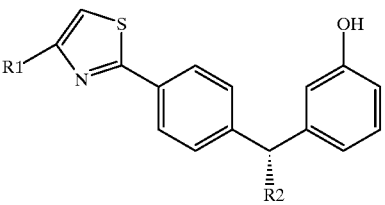

were prepared by desilylation of the corresponding silyl ethers, by similar methods to that described in Example 37.

Example 38 ethyl 2-(2-{4-[(R)-1-[(2S,5R)-4-allyl-2,5-dimethylhexahydropyrazin-1-yl]-1-(3-hydroxyphenyl)methyl]phenyl}-1,3-thiazole-4-yl)acetate

Example 39 ethyl 2-[2-(2-4-[(R)-1-[(2S,5R)-4-allyl-2,5-dimethylhexahydropyrazin-1-yl]-1-(3-hydroxyphenyl)methyl]phenyl-1,3-thiazol-4-yl)ethyl]aminoacetate

Example 40 ethyl 2-[[2-(2-4-[(R)-1-[(2S,5R)-4-allyl-2,5-dimethylhexahydropyrazin-1-yl]-1-(3-hydroxyphenyl)methyl]phenyl-1,3-thiazol-4-yl)ethyl](methyl)amino]acetate

Example 41 ethyl 2-(2-{4-[(R)-1-[(2S,5R)-4-propyl-2,5-dimethylhexahydropyrazin-1-yl]-1-(3-hydroxyphenyl)methyl]phenyl}-1,3-thiazole-4-yl)acetate

Example 42 ethyl 2-(2-4-[(4-allylpiperazino)(3-hydroxyphenyl)methyl]phenyl-1,3-thiazol-4-yl)acetate

Example 43 ethyl 2-(2-{4-[(R)-1-[(2S,5R)-4-benzyl-2,5-dimethylhexahydropyrazin-1-yl]-1-(3-hydroxyphenyl)methyl]phenyl}-1,3-thiazole-4-yl)acetate

| Ex | R1 | R2 | m/z | ¹H nmr |
|---|---|---|---|---|
| 38 | 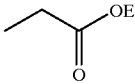 | 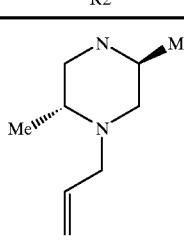 | 506 | δ_H(400MHz, CDCl₃): 7.84(2H, d), 7.50(2H, d), 7.18 (2H, m), 6.73(2H, m), 6.63(1H, s), 5.88(1H, m), 5.52(1H, brs), 5.18(3H, m), 4.21(2H, q), 3.90(2H, s), 3.37(1H, dd), 2.85(2H, m), 2.62(2H, m), 2.50 (1H, m), 2.16(1H, m), 1.95(1H, m), 1.28(3H, t), 1.16(3H, d), 1.01(3H, d). |
| 39 | 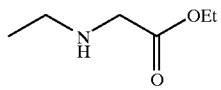 | 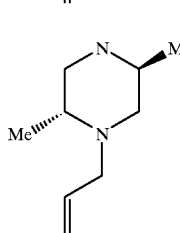 | 535 | δ_H(400MHz, CDCl₃): 7.83(2H, d), 7.47(2H, d), 7.14 (2H, m), 6.67(2H, m), 6.58(1H, s), 5.89(1H, m), 5.19(3H, m), 4.18(2H, q), 4.00(2H, s), 3.50(2H, s), 3.39(1H, dd), 2.94(1H, dd), 2.81(1H, d), 2.48–2.66 (4H, m), 2.18(1H, m), 1.97(1H, m), 1.28(3H, t), 1.11(3H, d), 1.02(3H, d). |
| 41 | 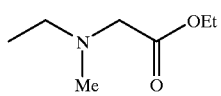 | 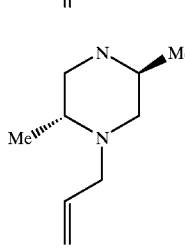 | 549 | δ_H(400MHz, CDCl₃): 7.84(2H, d), 7.47(2H, d), 7.16 (2H, m), 6.73(2H, m), 6.60(1H, s), 6.44(1H, brs), 5.88(1H, m), 5.18(3H, m), 4.20(2H, q), 3.95(2H, s), 3.38(2H, s), 2.91(1H, m), 2.82(1H, m), 2.60(2H, m), 2.48(4H, m), 2.18(1H, m), 1.97(1H, m), 1.28 (3H, t), 1.15(3H, d), 1.02(3H, d). [α]_D+13.34, c=0.013 |
| 41 | 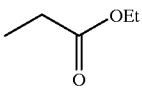 | 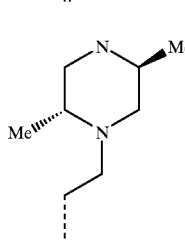 | 508 | δ_H(400MHz, CDCl₃): 7.84(2H, d), 7.50(2H, d), 7.17 (2H, m), 6.72(2H, m), 6.60(1H, s), 5.18(1H, s), 4.20 (2H, q), 3.89(2H, s), 2.84(1H, dd), 2.60(3H, m), 2.48(1H, m), 2.20(2H, m), 1.92(1H, m), 1.41–1.61 (3H, m), 1.27(3H, t), 1.16(3H, d), 0.99(3H, d), 0.87 (3H, t). |
| 42 | 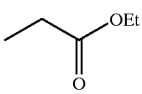 | 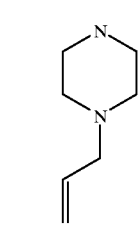 | 478 | δ_H(300MHz, DMSO-d₆): 9.30(1H, s), 7.82(2H, d), 7.50(2H, d), 7.06(1H, dd), 5.77(2H, m), 5.12(2H, m), 4.22(1H, s), 4.10(2H, q), 3.85(2H, s), 2.94(2H, d), 2.27–2.44(8H, m), 1.19(3H, t). |
| 43 | 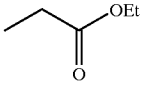 | 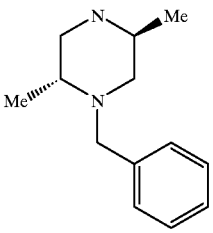 | 556 | δ_H(400MHz, DMSO-d₆): 9.30(1H, s), 7.82(2H, d), 7.50(3H, m), 7.28(4H, m), 7.20(1H, m), 7.13(1H, dd), 6.72(2H, m), 6.63(1H, d), 4.94(1H, s), 4.10 (2H, q), 3.85(2H, s), 3.74(1H, d), 3.26(1H, m), 2.63 (4H, m), 1.98(2H, m), 1.18 93H, t), 1.04(6H, 2xd). |

Example 44

Ethyl 2-{4-[(R)-1-[(2S,5R)-4-propyl-2,5-dimethylhexahydropyrazin-1-yl]-1-(3-hydroxyphenyl)methyl]phenyl}-1,3-thiazole-4-carboxylate

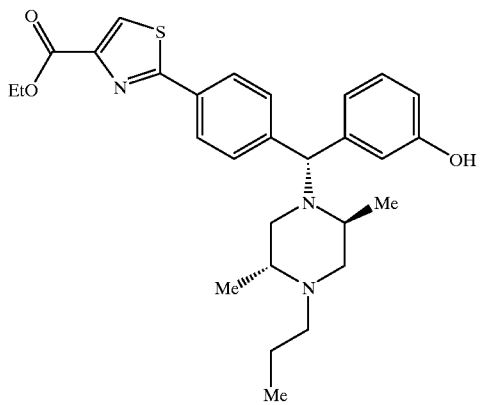

A solution of the compound from Preparation 31 (400 mg), propionaldehyde (86 μl), acetic acid (56 ml) and sodium triacetoxyborohydride (375 mg) in tetrahydrofuran (5 ml) was stirred at room temperature for 3 hours. The reaction mixture was then partitioned between ethyl acetate (25 ml) and saturated aqueous sodium bicarbonate solution (25 ml), and the phases separated. The aqueous phase was extracted with ethyl acetate (2×25 ml), the combined organic extracts dried ($Na_2SO_4$), and evaporated to dryness in vacuo. The residue was purified by column chromatography over silica gel using gradient elution (98/2–95/5 dichloromethane/methanol) to afford the title compound as a brown oil, 395 mg.

$R_f$: 0.62 (85/15 dichloromethane/methanol)

m/z: 494 (MH⁻)

$\delta_H$ (400 MHz, $CDCl_3$): 8.14 (1H, s), 7.92 (2H, d), 7.50 (2H, d), 7.16 (1H, dd), 6.72 (2H, m), 6.65 (1H, s), 5.18 (1H, s), 4.45 (2H, q), 2.92 (1H, m), 2.68 (2H, m), 2.58 (2H, m) 2.26 (2H, m), 2.06 (1H, m), 1.52 (2H, m), 1.42 (3H, t), 1.16 (3H, d), 1.04 (3H, d), 0.90 (3H, t).

Example 45

Ethyl 2-{4-[(R)-1-[(2S,5R)-4-benzyl-2,5-dimethylhexahydropyrazin-1-yl]-1-(3-hydroxyphenyl)methyl]phenyl}-1,3-thiazole-4-carboxylate

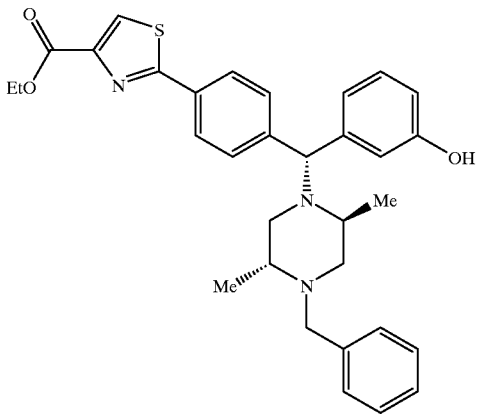

The title compound was prepared following a similar procedure to that described in Example 44 and using the compound of Preparation 31 and benzaldehyde, and was obtained as a light brown oil, 88%.

$R_f$: 0.31 (dichloromethane/methanol)

m/z: 542 (MH⁺)

$\delta_H$ (400 MHz, $CDCl_3$): 8.14 (1H, s), 7.92 (2H, d), 7.54 (2H, d), 7.15–7.32 (6H, m), 6.79 (1H, d), 6.73 (1H, d), 6.68 (1H, s), 5.08 (1H, s), 4.45 (2H, q), 3.92 (1H, d), 3.23 (1H, d), 2.74 (1H, d), 2.63 (3H, m), 2.04 (2H, m), 1.42 (3H, t), 1.10 (6H, 2xd).

Examples 46 and 47

Ethyl 2-{4-[(8aR)perhydropyrrolo[1,2-a]pyrazin-2-yl(3-hydroxyphenyl)methyl]phenyl}-1,3-thiazole-4-carboxylate

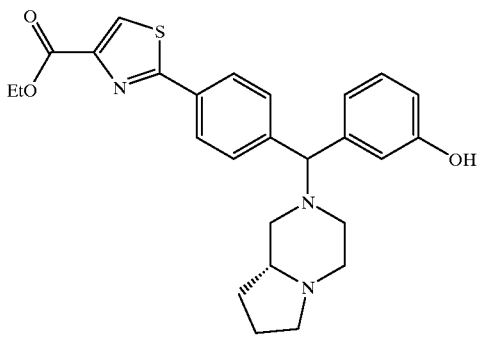

A suspension of the compounds from Preparation 38 (800 mg) and 40 (317 mg), and potassium carbonate (1.1 g) in acetonitrile (6 ml) was stirred under reflux for 18 hours. On cooling, the reaction mixture was partitioned between water and ethyl acetate. The phases were separated, and the aqueous layer extracted with ethyl acetate. The combined organic layers were dried (Na$_2$SO$_4$) and evaporated to dryness in vacuo, to give a brown oil. This material was purified by HPLC using a chiralpak AD column (2×25 cm), eluting at 9 ml/min with 70/30 hexane/isopropanol containing 0.6% trifluoroacetic acid and 0.4% diethylamine. The two separated products were each further purified by column chromatography over silica gel (90/10 dichloromethane/methanol) to afford the diastereoisomers of the title compound, isomer 1, 300 mg.

m/z: 464 (MH$^+$)

δH(400 MHz, CDCl$_3$): 8.12 (1H, s), 7.93 (2H, d), 7.50 (2H, d), 7.16 (1H, dd), 6.96 (1H, d), 6.91 (1H, s), 6.68 (1H, d), 4.98 (1H, br s), 4.44 (2H, q), 4.30 (1H, s), 2.94–3.12 (3H, m), 2.80 (1H, m), 2.34 (1H, m), 2.16 (2H, m), 1.77 (2H, m), 1.42 (3H, t), 0.91 (4H, m).

200 mg, of the second isomer was also isolated.

Example 48

Ethyl 2-{4-[[(3R,8aS)-3-methylperhydropyrrolo[1,2-a]pyrazin-2-yl](3-hydroxyphenyl)methyl]phenyl}-1,3-thiazole-4-carboxylate

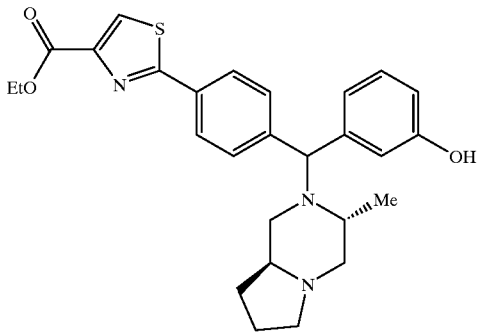

A suspension of the compounds from Preparations 38 (1.2 g) and 41 (533 mg) and potassium carbonate (1.7 g) in acetonitrile (20 ml) was stirred under reflux for 18 hours. On cooling, the mixture was partitioned between water and ethyl acetate and the phases separated. The aqueous layer was further extracted with ethyl acetate, the combined organic extracts dried (Na$_2$SO$_4$) and evaporated to dryness in vacuo. The residue was purified by column chromatography over silica gel, (hexane/isopropanol/ammonium hydroxide), and again (95/5 ethyl acetate/triethylamine) to afford the title compound as a mixture of diastereoisomers, 125 mg.

R$_f$: 0.39 (95/5 ethyl acetate/triethylamine)

m/z: 478 (MH$^+$)

δ$_H$ (400 MHz, CDCl$_3$): 8.14 (1H, s), 7.93 (2H, d), 7.21 (2H, m), 7.12 (1H, m), 6.97 (1H, s), 6.87 (1H, s), 6.70 (1H, s), 5.50 (1H, br s), 5.38 (1H, s), 4.42 (2H, m), 2.94 (2H, m), 2.85 (1H, d), 2.57 (1H, m), 2.14 (3H, m), 1.70 (3H, m), 1.40 (3H, s), 1.22 )4H, m).

Example 49

(+)-2-{4-[(R)-1-[(2S,5R)-4-allyl-2,5-dimethylhexahydropyrazin-1-yl]-1-(3-hydroxyphenyl)methyl]phenyl}-1,3-thiazole-4-carboxylic acid

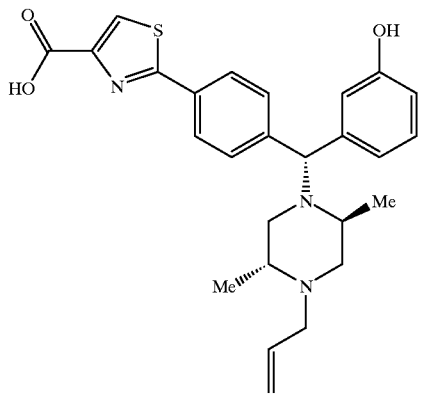

Aqueous sodium hydroxide solution (3 ml, 2N) was added to a solution of the compound from Example 37 (580 mg), in dioxan (6 ml) and methanol (3 ml) and the reaction stirred at room temperature for 3 hours. The reaction mixture was acidified to pH 5 using 2N hydrochloric acid then evaporated to dryness in vacuo. The residue was purified by column chromatography over silica gel using gradient elution (85/15/2.5–80/20/3 dichloromethane/methanol/ammonium hydroxide). This material was further purified on a polystyrene reverse phase resin using gradient elution (100/0–50/50 water/acetonitrile). The acetonitrile was evaporated in vacuo and the remaining aqueous solution was frozen and lyophilised to afford the title compound, 410 mg.

R$_f$: 0.22 (80/20/3 dichloromethane/methanol/ammonium hydroxide)

m/z: 464 (MH$^+$)

[α]$_D$+15.0 (c=0.08, methanol)

δ$_H$ (400 MHz, DMSO-d$_6$): 9.34 (1H, br s), 8.40 (1H, s), 7.90 (2H, d), 7.51 (2H, d), 7.14 (1H, dd), 6.70 (3H, m), 5.79 (1H, m), 5.18 (1H, d), 5.10 (1H, d), 5.00 (1H, s), 3.17 (1H, dd), 2.88 (1H, m), 2.75 (1H, dd), 2.56 (3H, m), 2.12 (1H, m), 1.88 (1H, m), 1.08 (3H, d), 0.96 (3H, d).

Found: C, 63.72; H, 6.13; N, 8.65. C$_{26}$H$_{29}$N$_3$O$_3$S.2/5CH$_2$Cl$_2$ requires C, 63.73; H,6.04;N, 8.44%.

Examples 50 to 59

The following compounds of the general formula:

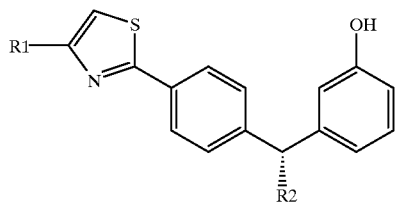

were prepared from the corresponding esters using a similar method to that described for Example 49.

Example 50

2-(2-{4-[(R)-1-[(2S,5R)-4-allyl-2,5-dimethylhexahydropyrazin-1-yl]-1-(3-hydroxyphenyl)methyl]phenyl}-1,3-thiazol-4-yl) acetic acid

Example 51

2-[2-(2-{4-[(R)-1-[(2S,5R)-4-allyl-2,5-dimethylhexahydropyrazin-1-yl]-1-(3-hydroxyphenyl)methyl]phenyl}-1,3-thiazol-4-yl) ethyl]aminoacetic acid

Example 52

2-[[2-(2-{4-[(R)-1-[(2S,5R)-4-allyl-2,5-dimethylhexahydropyrazin-1-yl]-1-(3-hydroxyphenyl)methyl]phenyl}-1,3-thiazol-4-yl) ethyl](methyl)amino]acetic acid

Example 53

2-{4-[(R)-1-[(2S,5R)-4-propyl-2,5-dimethylhexahydropyrazin-1-yl]-1-(3-hydroxyphenyl)methyl]phenyl}-1,3-thiazole-4-carboxylic acid

Example 54

2-(2-{4-[(R)-1-[(2S,5R)-4-propyl-2,5-dimethylhexahydropyrazin-1-yl]-1-(3-hydroxyphenyl)methyl]phenyl}-1,3-thiazol-4-yl) acetic acid

Example 55

2-(2-{4-[(4-allylpiperazino)(3-hydroxyphenyl) methyl]phenyl}-1,3-thiazol-4-yl)acetic acid

Example 56

2-{4-[(R)-1-[(2S,5R)-4-benzyl-2,5-dimethylhexahydropyrazin-1-yl]-1-(3-hydroxyphenyl)methyl]phenyl}-1,3-thiazole-4-carboxylic acid

Example 57

2-(2-{4-[(R)-1-[(2S,5R)-4-benzyl-2,5-dimethylhexahydropyrazin-1-yl]-1-(3-hydroxyphenyl)methyl]phenyl}-1,3-thiazol-4-yl) acetic acid

Example 58

2-(2-{4-[(8aR) perhydropyrrolo[1,2-a]pyrazin-2-yl (3-hydroxyphenyl)methyl]phenyl}-1,3-thiazol-4-yl) acetic acid

Example 59

2-{4-[[(3R,8aS)-3-methylperhydropyrrolo[1,2-a] pyrazin-2-yl](3hydroxyphenyl)methyl]phenyl}-1,3-thiazole-4-carboxylic acid

| Ex | R1 | R2 | m/z | [α]_D | ¹Hnmr/Analysis |
|---|---|---|---|---|---|
| 50 |  | 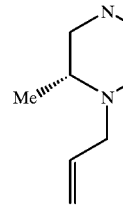 | 478 | +20.67 c = 0.12 | δ_H(400MHz, DMSO-d_6): 7.82(2H, d), 7.48(2H, d), 7.12(1H, dd), 6.68(3H, m), 5.77(1H, m), 5.16(1H, d), 5.08(1H, d), 4.98(1H, s), 3.74(2H, s), 3.16(1H, dd), 2.84(1H, m), 2.62(1H, dd), 2.54(3H, m), 2.08(1H, m), 1.85(1H, m), 1.06(3H, d), 0.94(3H, d). Found: C, 64.83; H, 6.36; N, 8.42. $C_{27}H_{31}N_3O_3S.6/5H_2O$ requires C, 64.96; H, 6.74; N, 8.42% |
| 51 | 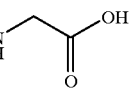 | 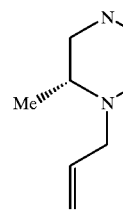 | 507 | +22.37 | δ_H(400MHz, DMSO-d_6): 7.83(2H, d), 7.55(1H, s), 7.49(2H, d), 7.12(1H, dd), 6.67(3H, m), 5.78(1H, m), 5.16(1H, d), 5.08(1H, d), 4.98(1H, s), 3.97(2H, s), 3.40(1H, brs), 3.24(2H, s), 3.15(1H, m), 2.85(1H, m), 2.72(1H, d), 2.51(3H, m), 2.10(1H, m), 1.87(1H, m), 1.07(3H, d), 0.93(3H, d). Found: C, 63.00; H, 6.84; N, 10.37. $C_{28}H_{34}N_4O_3S.3/2H_2O$ requires C, 63.02; H, 6.99; N, 10.50% |
| 52 | 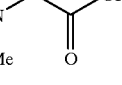 | 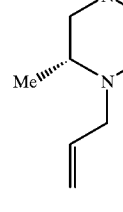 | 521 | +17.60 c = 0.10 | δ_H(400MHz, DMSO-d_6): 7.84(2H, d), 7.46(2H, d), 7.13(1H, dd), 6.68(3H, m), 5.78(1H, m), 5.16(1H, d), 5.08(1H, d), 4.98(1H, s), 3.85(2H, s), 3.17(3H, m), 2.86(1H, m), 2.72(1H, d), 2.54(3H, m), 2.34(3H, s), 2.09(1H, m), 1.88(1H, m), 1.05(3H, d), 0.92(3H, d). Found: C, 63.43; H, 7.04; N, 10.18. $C_{29}H_{36}N_4O_3S.3/2H_2O$ requires C, 63.59; H, 7.18; N, 10.23% |
| 53 | 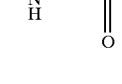 | 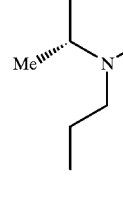 | 466 | +17.20 c = 0.10 | δ_H(400MHz, DMSO-d_6): 9.34(1H, brs), 8.38(1H, s), 7.88(2H, d), 7.52(2H, d), 7.14(1H, dd), 6.72(2H, m), 6.66(1H, d), 4.95(1H, s), 2.80(1H, d), 2.65(1H, m), 2.56(1H, d), 2.44(1H, m), 2.15(2H, m), 1.90(1H, m), 1.38(2H, m), 1.08(3H, d), 0.96(3H, d), 0.80(3H, t). Found: C, 57.60; H, 7.34; N, 7.75. $C_{26}H_{31}N_3O_3S.9/4H_2O$ requires C, 57.50; H, 7.34; N, 7.75% |
| 54 |  | 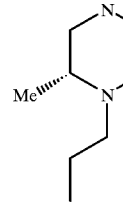 | 480 | +23.0 c = 0.10 | δ_H(400MHz, DMSO-d_6): 9.29(1H, s), 7.82(2H, d), 7.48(3H, m), 7.12(1H, dd), 6.70(2H, m), 6.05(1H, d), 4.94(1H, s), 3.76(2H, s), 3.17(2H, t), 2.78(1H, d), 2.64(1H, m), 2.42(1H, m), 2.15(2H, m), 1.89(1H, m), 1.36(2H, m), 1.08(3H, d), 0.94(3H, d), 0.81(3H, t). Found: C, 64.82; H, 6.78; N, 8.41. $C_{27}H_{33}N_3O_3S.H_2O$ requires C, 65.16; N, 7.09; N, 8.44% |
| 55 |  | 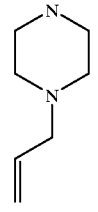 | 450 | | δ_H(400MHz, DMSO-d_6): 7.81(2H, d), 7.48(2H, d), 7.40(1H, s), 7.06(1H, dd), 6.82(2H, m), 6.56(1H, d), 5.78(1H, m), 5.15(1H, d), 5.08(1H, d), 4.20(1H, s), 3.69(2H, s), 2.92(2H, d), 2.27–2.42(8H, m). |

-continued

| Ex | R1 | R2 | m/z | [α]_D | ¹Hnmr/Analysis |
|---|---|---|---|---|---|
| 56 | EtNH-CH₂-C(O)-OEt | (2S,5R)-2,5-dimethyl-4-benzylpiperazinyl | 514 | −8.80 c = 0.10 | $\delta_H$(400MHz, DMSO-$d_6$): 9.38(1H, brs), 8.20(1H, s), 7.88(2H, d), 7.50(2H, d), 7.28(4H, m), 7.19(1H, m), 7.12(1H, dd), 6.72(2H, m), 6.64(1H, d), 4.4.94 (1H, s), 3.74(1H, d), 3.56(2H, s), 2.64 (4H, m), 1.98(2H, m), 1.05(6H, m). Found: C, 66.06; H, 6.43; N, 8.08. $C_{30}H_{31}N_3O_3S \cdot 17/10H_2O$ requires C, 66.20; H, 6.37; N, 7.72% |
| 57 | CH₃-C(O)-OH | (2S,5R)-2,5-dimethyl-4-benzylpiperazinyl | 528 | −0.6 | $\delta_H$(300MHz, DMSO-$d_6$): 7.81(2H, d), 7.50(2H, d), 7.41(1H, s), 7.26(4H, m), 7.20(1H, m), 7.11(1H, dd), 6.72 92H, m), 6.63(1H, d), 4.92(1H, s), 3.70(2H, s), 3.17(2H, s), 2.64(4H, m), 2.00(2H, m), 1.02(6H, m). |
| 58 | CH₃-C(O)-OH | octahydropyrrolo[1,2-a]pyrazinyl | 436 | +36.7 c = 0.12 | $\delta_H$(300MHz, DMSO-$d_6$): 9.40(1H, brs), 8.32(1H, s), 7.89(2H, d), 7.53(2H, d), 7.08(1H, dd), 6.82(2H, m), 6.57(1H, d), 4.30(1H, s), 2.90(3H, m), 2.69(1H, d), 2.24(1H, m), 2.06(3H, m), 1.65(4H, m), 1.21(1H, m). Found: C, 61.76; H, 5.60; N, 9.27. $C_{24}H_{25}N_3O_3S \cdot 3/2H_2O$ requires C, 62.32; H, 6.10; N, 9.08% |
| 59 | EtNH-CH₂-C(O)-OEt | methyl-octahydropyrrolo[1,2-a]pyrazinyl | 450 | | $\delta_H$(300MHz, DMSO-$d_6$): 9.20(1H, brs), 8.38(1H, s), 7.94(2H, d), 7.34(2H, d), 7.08(1H, dd), 6.80(1H, s), 6.74(1H, d), 6.60(1H, d), 5.30(1H, s), 2.79–2.96(4H, m), 2.00-2.22(3H, m), 1.18(3H, d). Found: C, 58.80; H, 6.27; N, 8.39. $C_{25}H_{27}N_3O_3S \cdot 33/10H_2O$ requires C, 58.99; 1H, 6.65; N, 8.25% |

Example 60

2-{4-[(R)-1-[(2S,5R)-4-benzyl-2,5-dimethylhexahyropyrazin-1-yl]-1-(3-hydroxyphenyl)methyl]phenyl}isonicotinic acid

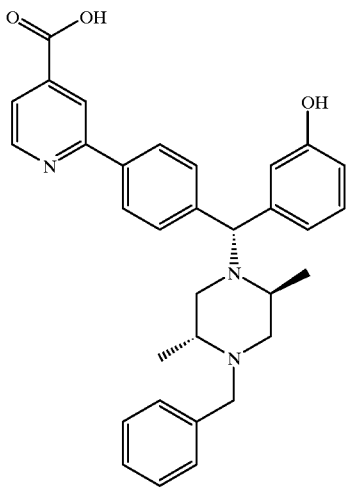

Potassium Hydroxide (0.29 g) was added to a solution of the compound of Preparation 73 (0.47 g) in n-butanol (30 ml). The reaction mixture was heated under reflux for 16 hrs, after which time the cooled mixture was neutralised to pH 6.5 with 2N HCl and evaporated under reduced pressure. The residue was diluted with H₂O/MeOH (1/1, v/v) (6 ml) and loaded onto a polystyrene gel reverse phase column and the product was eluted with H₂O followed by an elution gradient of H₂O/MeOH (55/45–15/85, v/v). The MeOH was evaporated under reduced pressure and the remaining aqueous solution was frozen and lyophilised to afford the title compound as a white solid (343 mg).

$R_f$ 0.2 ( CH₂Cl₂/MeOH/0.88NH₃, 80/20/4, v/v).

$\delta_H$ (300 MHz, DMSO): 8.60 (1H, d), 8.20 (1H, s), 8.00 (2H, d), 7.62 (1H, m), 7.50 (2H, d), 7.39–7.10 (6H, m), 6.80–6.60 (3H, m), 5.00 (1H, s), 3.90 (1H, d), 3.20 (1H, d), 2.80–2.60 (4H, m), 2.00 (2H, m), 1.10 (6H, 2xd).

Analysis: Found C, 68.71; H, 6.05; N, 7.35; $C_{32}H_{33}N_3O_3 \cdot 3$ H₂O requires C, 68.43; H, 7.00; N, 7.48%.

Example 61

2-(4-{4-[(R)-1-[(2S,5R)-4-benzyl-2,5-dimethylhexahydropyrazin-1-yl]-1-(3-hydroxyphenyl)methyl]phenyl}-1H-pyrazol-1-yl)acetic acid

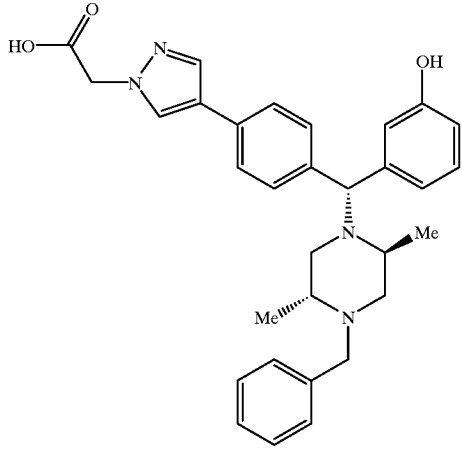

The title compound was prepared using a sequence of reactions as described for Example 37 followed by a similar method to that described for Example 22 and using the compound of Preparation 49.

$R_f$ 0.2 (CH$_2$C$_2$/MeOH/0.88NH$_3$, 16/20/4, v/v).

$\delta_H$ (300 MHz, DMSO-d$_6$): 8.00 (1H, s), 7.80 (1H, s), 7.45 (2H, d), 7.35–7.05 (8H, m), 6.75 (2H, d), 6.60 (1H, d), 4.90 (1H, s), 4.70 (2H, s), 3.85 (1H, d), 3.20 (1H,d), 2.80–2.50 (4H, m), 2.00 (2H, m), 1.05 (6H, m).

Analysis: Found C, 63.63; H, 6.75; N, 9.58; C$_{31}$H$_{34}$N$_4$O$_3$.4H$_2$O requires, C, 63.90; H, 7.27; N, 9.62%.

Example 62

Ethyl 5-(4-{4-[(R)-1-[(2S,5R)-4-benzyl-2,5-dimethylhexahydropyrazin-1-yl]-1-(3-[1-(tert-butyl)-1,1-dimethylsily]oxyphenyl)methyl]phenyl}-1H-pyrazol-1-yl)pentanoate

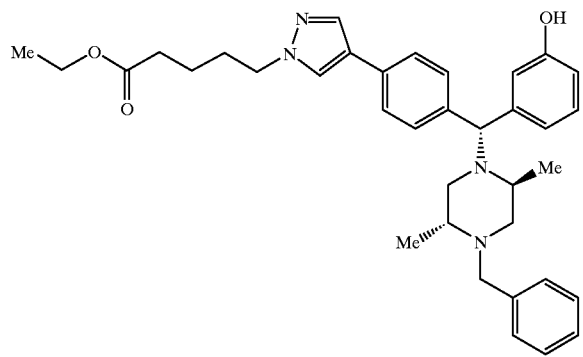

The title compound was prepared using a similar method to that described for Example 13 using the compound of Preparation 48 and ethyl-5-bromovalerate. The crude product was purified by column chromatography over silica gel eluting with (ethyl acetate/pentane, 1/2, v/v), followed by a second column eluting with (pentane/isopropanol/0.88 ammonium hydroxide, 90/10/0.75, v/v) to afford the title compound as a oil.

$R_f$ 0.1 (ethyl acetate/pentane, 1/2, v/v)

$\delta_H$ (400 MHz, CDCl$_3$ ): 7.76 (1H, s), 7.60 (1H, s), 7.45–7.10 (10H, m), 6.80–6.64 (3H, m), 6.22 (1H, s), 5.02 (1H, br s), 4.16 (4H, m), 3.91 (1H, d), 3.22 (1H, d), 2.18–2.50 (4H, m), 2.30 (4H, m), 2.10–1.90 (4H, m), 1.62 (2H, m), 1.22 (3H, t), 1.05 (6H, m).

Example 63

5-(4-{4-[(R)-1-[(2S,5R)-4-benzyl-2,5-dimethylhexahydropyrazin-1-yl]-1-(3-hydroxyphenyl)methyl]phenyl}-1H-pyrazol-1-yl)pentanoic acid

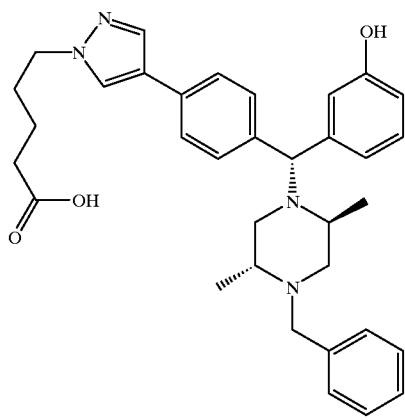

The title compound was prepared by the method of Example 22 using the compound of Example 62.

$R_f$ 0.2 ( CH$_2$Cl$_2$/MeOH/0.88NH$_3$, 80/20/4, v/v)

m/z 553 (MH$^+$)

$\delta_H$ (300 MHz, DMSO): 8.05 (1H, s), 7.80 (1H, s), 7.45 (2H, d), 7.40–7.15 (7H, m), 7.05 (1H, t), 6.80–6.60 (3H, m), 4.80 (1H, s), 4.05 (1H, t), 3.75 (1H, d), 3.20 (1H, d), 2.70–2.55 (4H, m), 2.00 (4H, t), 1.80 (2H, m), 1.40 (2H, m), 1.00 (6H, 2xd).

Examples 64 and 65

Methyl 3-(5-{4-[(R)-1-[(2S,5R)-4-benzyl-2,5-dimethylhexahydropyrazin-1-yl]-1-(3-hydroxyphenyl)methyl]phenyl}-1,3,4-oxadiazol-2-yl) propanoate and Methyl 3-(5-{4-[(R)-1-[(2S,5R)-4-benzyl-2,5-dimethylhexahydropyrazin-1-yl]-1-(3hydroxyphenyl)methyl]phenyl}-4H-1,2,4-triazol-3-yl)propanoate

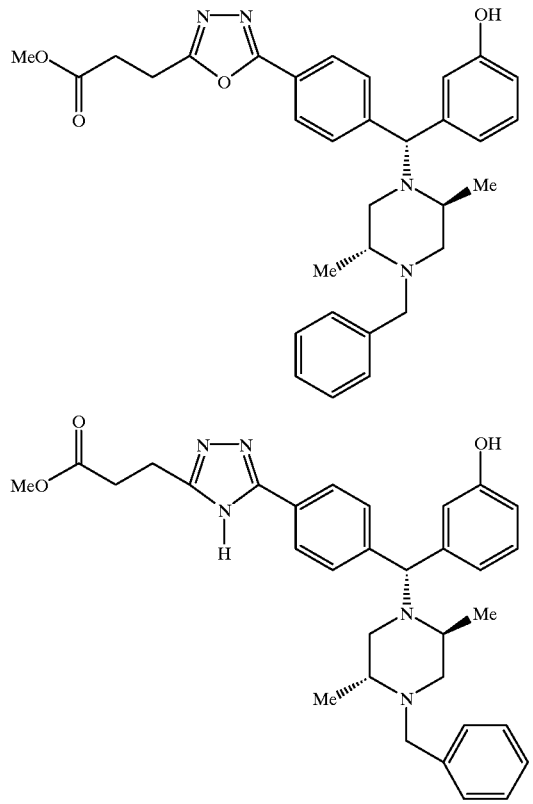

1,4-dimethoxy-4-oxo-1-butaniminium hydrochloride (J. Med. Chem., 1991, 34, 2468–73) (89 mg) was added to a solution of the copmound of Preparation 51 (213 mg) in MeOH (10 ml) the reaction mixture was refluxed for 48 hrs and then partitioned between ethyl acetate and saturated sodium bicarbonate solution. The organic phase was separated and washed with saturated brine, dried over $MgSO_4$ and evaporated under reduced pressure. The crude product was purified by column chromatography on silica gel eluting with EtOAc/Pentane (1/1, v/v) to afford Example 64 as a white foam (88 mg).

$R_f$ 0.45 (ether).

m/z: 541 (MH$^+$)

δ(CDCl$_3$): 7.88 (2H, d), 7.55 (2H, d), 7.30–7.10 (6H, m), 6.70–6.60 (3H, m), 5.07 (2H, m), 3.88 (1H, d), 3.70 (3H, s), 3.25–3.10 (3H, m), 2.89 (2H, m), 2.75–2.50 (4H, m), 2.03–1.94 (2H, m), 1.06 (6H, m).

Found M$^+$541.282 $C_{32}H_{36}N_4O_4$ requires M 541.2815 followed by Example 65 as a white foam (48 mg).

$R_f$ 0.19 (ether)

m/z: 540 (MH$^+$).

δ (CDCl$_3$): 7.83 (2H, d), 7.43 (2H, d), 7.30–7.05 (6H, m), 6.75–6.60 (3H, m), 5.02 (1H, br s), 3.86 (1H, d), 3.68 (3H, s), 3.17 (1H, d), 3.10 (2H, m), 2.79 (2H, m), 2.70–2.50 (4H, m), 2.05–1.95 (2H, m), 1.02 (6H, m).

Found M$^+$540.2965 $C_{32}H_{37}N_5O_3$ requires M 540.2975

Example 66

3-(5-{4-[(R)-1-[(2S,5R)-4-benzyl-2,5-dimethylhexahydropyrazin-1-yl]-1-(3-hydroxyphenyl)methyl]phenyl}-1,3,4-oxadiazol-2-yl)propanoic acid

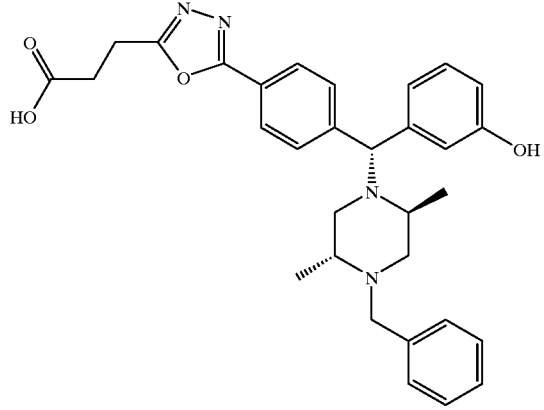

The title compound was prepared using a similar method to that described for Example 22 using the corresponding ester, Example 64.

$R_f$ 0.47 (CH$_2$Cl$_2$/MeOH/AcOH, 80/20/1, v/v).

m/z 527 (MH$^+$)

δ$_H$ (300 MHz, DMSO): 7.85 (2H, d), 7.54 (2H, d), 7.25–7.05 (6H, m), 6.70–6.55 (3H, m), 4.95 (1H, s), 3.71 (1H, d), 3.21 (1H, d), 3.01 (2H, t), 2.65–2.40 (6H, m), 2.00–1.85 (2H, m), 0.99 (6H, m).

Analysis: Found C, 64.70; H, 6.08; N, 9.58. $C_{31}H_{34}N_4O_4$.2.75 H$_2$O requires C, 64.62; H, 6.91; N, 9.72%.

[α]$_D$–3.0°, c=0.1/methanol.

Example 67

Ethyl 4-(5-{3-[(R)-1-[(2S,5R)-4-benzyl-2,5-dimethylhexahydropyrazin-1-yl]-1-(3-hydroxyphenyl)methyl]phenyl}-1,3,4-oxadiazol-2-yl)butanoate

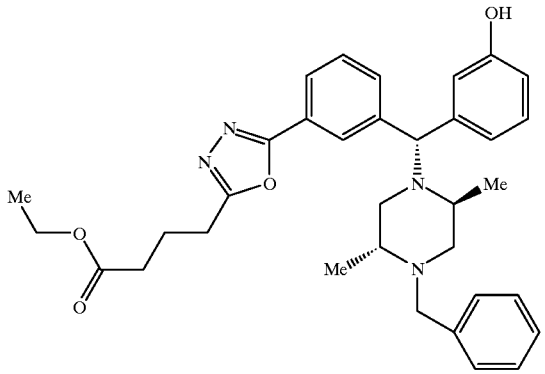

Iodine (827 mg) and triphenylphosphine (855 mg) were mixed in $CH_2Cl_2$ (10 ml) and stirred at room temperature for 15 mins. The compound of Preparation 55 (475 mg) was added to the mixture followed by triethylamine (675 mg). The reaction mixture was stirred for 18 hrs after which time the reaction mixture was evaporated under reduced pressure and pre-absorbed onto silica gel and purified by column chromatography on silica gel eluting with EtOAc/Hexane (10/90–100%EtOAc, v/v) to afford the title compound as a solid (1.16 g).

The title compound was isolated as a minor component from the reaction the major component of which was the corresponding phenolic ester.

$R_f$ 0.59 (EtOAc/Pentane, 1/1, v/v).

m/z: 711 (MH$^+$)

Example 68

4-(5-{3-[(R)-1-[(2S,5R)-4-benzyl-2,5-dimethylhexahydropyrazin-1-yl]-1-3-hydroxyphenyl)methyl]phenyl}-1,3,4-oxadiazol-2-yl)butanoic acid

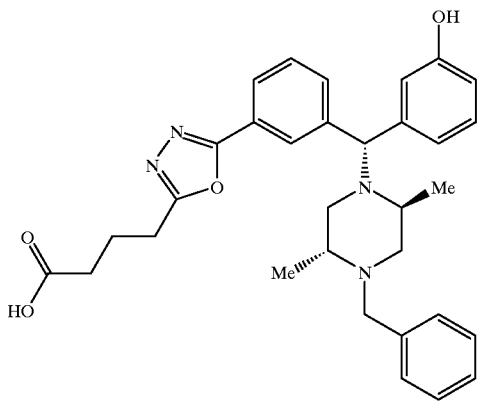

The title compound was prepared using a similar method to that described for Example 22 using the crude product of Example 67 containing the title compound as the major component The crude product was purified by column chromatography on silica gel eluting with $CH_2Cl_2$/MeOH (95/5, v/v) to afford the title compound as a white solid.

$R_f$ 0.35 ($CH_2Cl_2$/MeOH, 9/1, v/v).

m/z: 541 (MH$^+$)

$\delta_H$ (300 MHz, DMSO) 12.11 (1H, s), 9.32 (1H, s), 8.05 (1H, s), 7.78 (1H, d), 7.59 (1H, d), 7.49 (1H, m), 7.30–7.05 (6H, m), 6.75–6.60 (3H, m), 4.98 (1H, s), 3.72 (1H, d), 2.94 (2H, t), 2.80–2.50 (4H, m), 2.37 (2H, t), 2.10–1.90 (4H, m), 1.10 (6H, m).

$[\alpha]_D$ –2.60°, c=0.1/methanol.

Example 69

3-(5-{4-[(R)-1-[(2S,5R)-4-benzyl-2,5-dimethylhexahydropyrazin-1-yl]-1-(3-hydroxyphenyl)methyl]phenyl}-4H-1,2,4-triazol-3-yl)propanoic acid

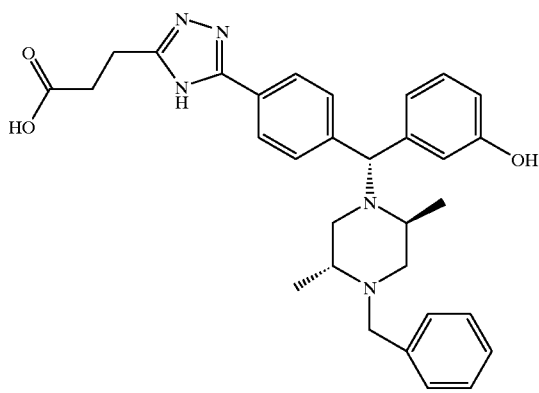

1M NaOH (1 ml) was added to a solution of the compound of Example 65 (29 mg) in dioxan (1 ml). The resulting solution was stirred at room temperature for 18 hrs after which time the reaction mixture was loaded directly on to an ion exchange column (AG-50 sulphonic acid resin). The product was eluted through the column with $H_2O$ (100 ml), and then with 1% 0.88NH$_3$ (200 ml) followed by 2% 0.88NH$_3$ (300 ml). The aqueous solution was then frozen and lyophilised to afford the title compound as a white solid (8 mg).

$R_f$ 0.52 ($CH_2Cl_2$/MeOH/AcOH, 80/20/1, v/v).

m/z: 526 (MH$^+$)

$\delta_H$ (300 MHz, DMSO): 9.25 (1H, s), 7.83 (2H, d), 7.43 (2H, d), 7.25–7.00 (6H, m), 6.70–6.55 (3H, m), 4.87 (1H, s), 3.70 (1H, d), 3.25 (1H, d), 2.87 (2H, m), 2.70–2.40 (6H, m), 2.10–1.90 (2H, m), 0.99 (6H, m).

Example 70

Methyl 3-(5-{4-[(R)-1-[(2S,5R)4-benzyl-2,5-dimethylhexahydropyrazin-1-yl]-1-(3-hydroxyphenyl)methyl]phenyl}-1,3,4-oxadiazol-2-yl)benzoate

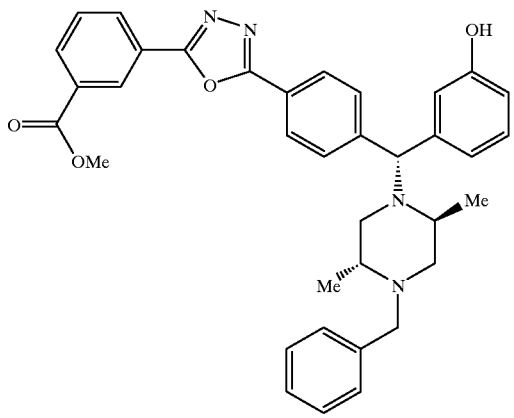

The title compound was prepared using a similar method to that described for Example 67 using the compound of Preparation 56.

$R_f$ 0.73 (Ether).

m/z: 589 (MH$^+$).

δ (CDCl$_3$): 8.76 (1H, s), 8.36 (1H, d), 8.23 (1H, d), 8.07 (2H, d), 7.70–7.60 (3H, m), 7.35–7.10 (6H, m), 6.85–6.70 (3H, m), 5.14 (1H, br s), 5.03 (1H, br s), 3.99 (3H, s), 3.92 (1H, d), 3.23 (1H, d), 2.80–2.60 (4H, m), 2.10–2.00 (2H, m), 1.11 (6H, m).

Example 71

3-[(5-{4-[(R)-1-[(2S,5R)-4-benzyl-2,5-dimethylhexahydropyrazin-1-yl]-1-(3hydroxyphenyl)methyl]phenyl}-1,3,4-oxadiazol-2-yl)methyl]benzoic acid

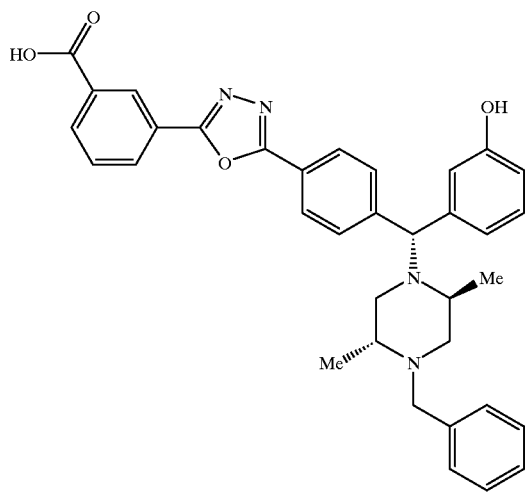

The title compound was prepared and purified by a similar method to that described for Example 22 using the corresponding ester, Example 70 to afford a cream solid.

$R_f$ 0.70 (CH$_2$Cl$_2$/MeOH/AcOH, 90/10/1, v/v).

m/z: 575 (MH$^+$).

δ$_H$ (300 MHz, DMSO): 9.35 (1H, bs), 8.58 (1H, s), 8.27 (1H, m), 8.14 (1H. m), 8.06 (2H, d), 7.69 (1H, t), 7.63 (2H, d), 7.30–7.10 (6H, m), 6.75–6.60 (3H, m), 5.01 (1H, s), 3.74 (1H, d), 3.28 (2H, m), 2.70–2,55 (4H, m), 2.10–1.90 (2H, m), 1.05 (6H, m).

Analysis: Found C, 66.01; H, 6.13; N, 9.01; C$_{35}$H$_{34}$N$_4$O$_4$.3.4H$_2$O requires C, 66.11; H, 6.47; N, 8.81%.

[α]$_D$ –4.60°, c=0.1/methanol.

Example 72

Methyl 4-(5-{4-[(R)-1-[(2S,5R)-4-benzyl-2,5-dimethylhexahydropyrazin-1-yl]-1-(3-hydroxyphenylmethyl]phenyl}-1,3,4-oxadiazol-2-yl)benzoate

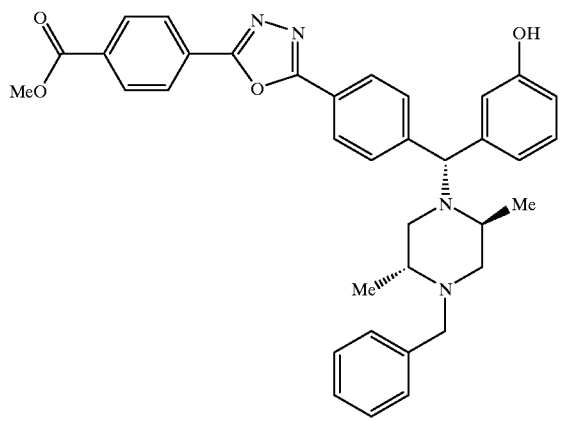

The title compound was prepared by a similar method to that described for Example 67 using the compound of Preparation 57 to afford the title compound as a white solid.

$R_f$ 0.75 (Ether).

m/z 589 (MH$^+$).

δ (CDCl$_3$): 8.21 (4H, m), 8.06 (2H, d), 7.64 (2H, d), 7.35–7.15 (6H, m), 6.85–6.70 (3H, m), 5.14 (1H, br s), 5.03 (1H, br s), 3.97 (3H, s), 3.92 (1H, d), 3.22 (1H, d), 2.80–2.55 (4H, m), 2.10–2.00 (2H, m), 1.11 (6H, m).

Example 73

4-[(5-{4-[(R)-1-[(2S,5R)-4-benzyl-2,5-dimethylhexahydropyrazin-1-yl]-1-(3-hydroxyphenyl)methyl]phenyl}-1,3,4-oxadiazol-2-yl)methyl]benzoic acid

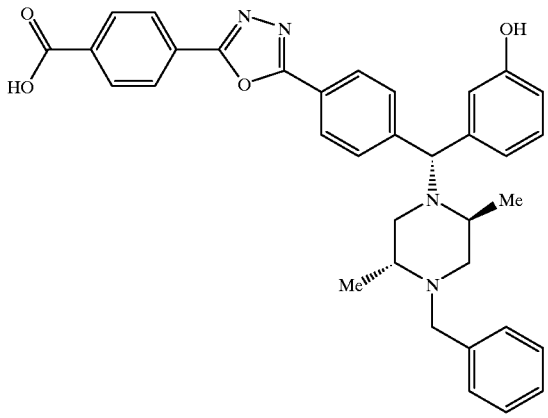

The title compound was prepared by a similar method to that described for Example 22 using the compound of Example 72, to afford the title compound as a white solid.

$R_f$ 0.68 (CH$_2$Cl$_2$/MeOH/AcOH, 90/10/1, v/v).

m/z: 575(MH$^+$).

$\delta_H$ (300 MHz, DMSO) 9.34 (1H, s), 8.30–8.00 (6H, m), 7.63 (2H, m), 7.40–7.10 (6H, m), 6.80–6.60 (3H, m), 5.02 (1H, bs), 3.77 (1H, bs), 3.28 (2H, m), 2.80–2.30 (4H, m), 2.20–1.95 (2H, m), 1.05 (6H, m).

Analysis: Found C, 68.74; H, 6.11; N, 8.89; C$_{35}$H$_{34}$N$_4$O$_4$·2H$_2$O requires C, 68.84; H, 6.27; N, 9.17%.

[α]$_D$ –7.80°, c=0.1/methanol.

Example 74

Ethyl 3-(3-{4-[(R)-1-[(2S,5R)-4-benzyl-2,5-dimethylhexahydropyrazin-1-yl]-1-(3-hydroxyphenyl)methyl]phenyl}-1,2,4-oxadiazol-5-yl)propanoate

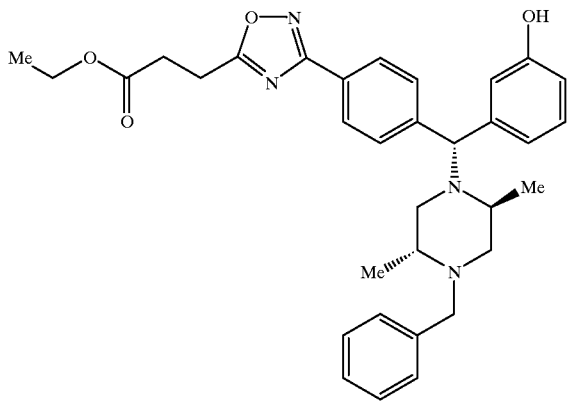

Sodium hydroxide (180 mg) was added to a solution of the product from Preparation 21 (400 mg) in dioxan (15 ml) followed by addition of tetrabutyl ammonium sulphate (25 mg) and ethyl succinyl chloride (222 mg) in dioxan (10 ml). The reaction mixture was stirred at room temperature for 30 mins and then heated to reflux for 18 hrs, after which time the reaction mixture was filtered and evaporated under reduced pressure. The crude product was purified by column chromatography on silica gel eluting with Pentane/Ether (60/40, v/v) to afford the title compound as an oil (74 mg).

m/z: 556 (MH$^+$).

$\delta_H$ (300 MHz, CDCl$_3$): 7.95 (2H, d), 7.55 (2H, d), 7.35–7.15 (6H, m), 6.82–6.65 (3H, m), 5.10 (1H, s), 4.18 (2H, q), 3.90 (1H, d), 3.25 (3H, m), 2.92 (2H, t), 2.75–2.50 (4H, m), 2.02 (2H, m), 1.25 (3H, t), 1.10 (6H, dd).

Example 75

3-(3-{4-[(R)-1-[(2S,5R)-4-benzyl-2,5-dimethylhexahydropyrazin-1-yl]-1-(3-hydroxyphenyl)methyl]phenyl}-1,2,4-oxadiazol-5-yl) propanoic acid

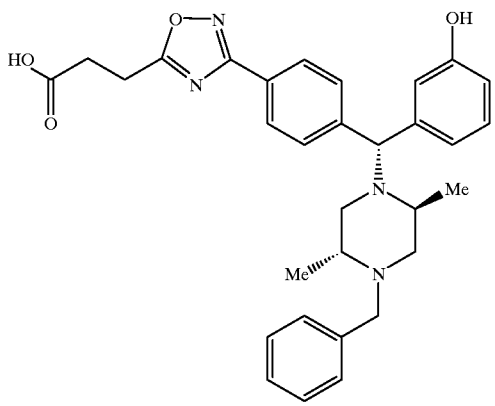

The title compound was prepared by a similar method to that described for Example 22 using the corresponding ester, Example 74, to afford the title compound as a white solid.

$R_f$ 0.16 (methyl isobutyl ketone/acetic acid/water; 2/1/1).

m/z: 527 (MH$^+$).

$\delta_H$ (400 MHz, DMSO): 7.85 (2H, d), 7.50 (2H, d), 7.22–7.08 (6H, m), 6.70–6.60 (3H, 2xd), 4.95 (1H, s), 3.70 (1H, d), 3.20 (1H, d), 2.95 (2H, t), 2.60 (4H, m), 2.25 (2H, m), 2.00–1.90 (2H, m), 1.00 (6H, m).

[α]$_D$ –1.60°, c=0.1 /methanol.

Example 76

Methyl 3-(3-{4-[(R)-1-[(2S,5R)-4-benzyl-2,5-dimethylhexahydropyrazin-1-yl]-1-(3-hydroxyphenylmethyl]phenyl}-1,2,4-oxadiazol-5-yl)benzoate

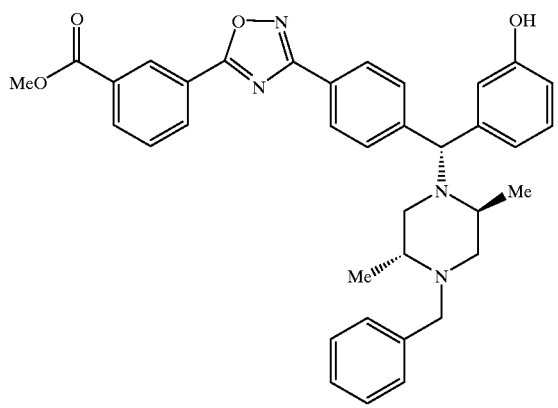

Monomethyl isophthaloyl chloride (446 mg) was added to a stirred solution of the product from Preparation 21 (500 mg) in pyridine (20 ml). The reaction mixture was stirred at room temperature for 1 hr and then heated to reflux for 18 hrs after which time the reaction mixture was evaporated under reduced pressure and the residue azeotroped with toluene and $CH_2Cl_2$.

The crude product was purified by column chromatography on silica gel eluting wuth $CH_2Cl_2$/Ether (95/5, v/v) to afford the title compound (228 mg).

$R_f$ 0.3 ($CH_2Cl_2$/Ether, 95/5, v/v).

m/z:589 (MH$^+$).

Analysis: Found C, 72.31; H, 6.21; N, 9.23; $C_{36}H_{36}N_4O_4$.0.5$H_2O$ requires C, 72.34; H, 6.24; N, 9.37%.

δ(CDCl$_3$): 8.90 (1H, s), 8.4 (1H, d), 8.30 (1H, d), 8.10 (2H, d), 7.60 (3H, m), 7.35–7.15 (6H, m), 6.85–6.70 (3H, m), 5.14 (1H, s), 4.00 (3H, s), 3.92 (1H, d), 3.22 (1H, d), 2.80–2,55 (4H, m), 2.05 (2H, m), 1.12 (6H, m).

Example 77

3-(3-{4-[(R)-1-[(2S,5R)-4-benzyl-2,5-dimethylhexahydropyrazin-1yl]-1-(3-hydroxyphenyl)methyl]phenyl}-1,2,4-oxadiazol-5-yl)benzoic acid

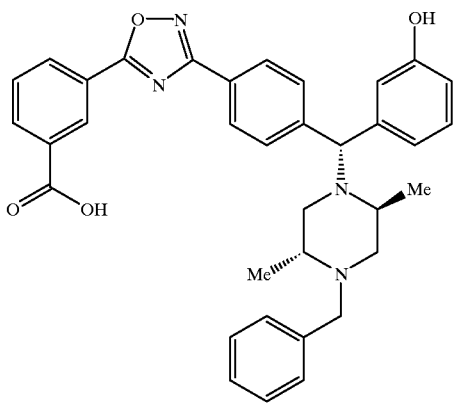

The title compound was prepared by a similar method to that described for Example 22 using the corresponding ester, Example 76 to afford the title compound as a white solid.

$R_f$ 0.21 ($CH_2Cl_2$/MeOH, 9/1, v/v).

m/z 575 (MH$^+$).

$δ_H$ (300 MHz, DMSO): 8.65 (1H, s), 8.35 (1H, d), 8.25 (1H, d), 8.05 (2H, d), 7.75 (1H, t), 7.60 (2H, d), 7.30–7.10 (6H, m), 6.70 (3H, m), 5.00 (1H, s), 3.75 (1H, d), 2.60 (4H, m), 2.00 (2H, m), 1.05 (6H, m).

Analysis: Found C, 69.07; H, 5.77; N, 9.00; $C_{35}H_{34}N_4O_4$.1.75$H_2O$ requires C, 69.35; H, 6.24; N, 9.24%.

$[α]_D$ –8.0°, c=0.1/methanol.

Example 78

Methyl 4-(3-4-[(R)-1-[(2S,5R)-4-benzyl-2,5-dimethylhexahydropyrazin-1-yl]-1-(3-hydroxyphenyl)methyl]phenyl-1,2,4-oxadiazol-5-yl)benzoate

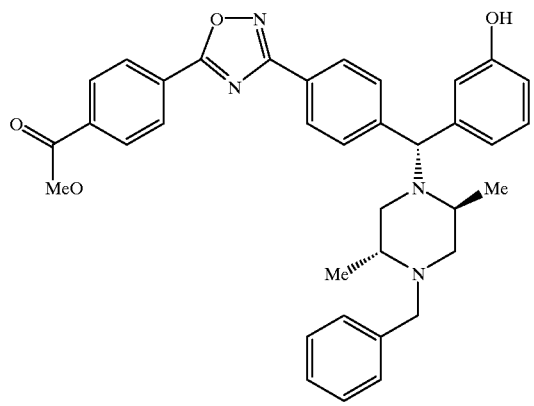

To a stirred solution of the compound of Preparation 21 (500 mg) in $CH_2Cl_2$ (6 ml) was added monomethyl terphthalate (223 mg), N-methyl morpholine (0.2 ml), dimethylaminopyridine (68 mg) and 1-(3-dimethylaminopropyl)-3-ethylcarbodiimide hydrochloride (260 mg) respectively. The reaction mixture was stirred at room temperature for 18 hrs, the solvent was then evaporated under reduced pressure and the residue partitioned between EtOAc/H$_2$O. The organic phase was separated and washed with saturated brine, dried over MgSO$_4$ and evaporated under reduced pressure to afford the title compound (629 mg) which was used immediately without further purification. The above intermediate (629 mg) was dissolved in pyridine (10 ml) and heated to reflux for 18 hrs after which time the solvent was evaporated under reduced pressure and azeotroped with toluene and CH$_2$Cl$_2$. The crude product was purified by column chromatography on silica gel eluting with CH$_2$Cl$_2$/Ether (95/5, v/v) to afford the title compound as a oil (221 mg).

m/z:589 (MH$^-$).

$\delta_H$ (300 MHz, CDCl$_3$): 8.31 (2H, d), 8.22 (2H, d), 8.10 (2H, d), 7.60 (2H, d), 7.35–7.15 (6H, m), 6.85–6.75 (2H, m), 6.70 (1H, m), 5.15 (1H, s), 4.00 (3H, s), 3.90 (1H,d), 3.20 (1H, d), 2.80–2.55 (4H, m), 2.05 (2H, m), 1.15 (6H, m).

Example 79

4-(3-{4-[(R)-1-[(2S,5R)-4-benzyl-2,5-dimethylhexahydropyrazin-1-yl]-1-(3-hydroxyphenyl)methyl]phenyl}-1,2,4-oxadiazol-5-yl)benzoic acid

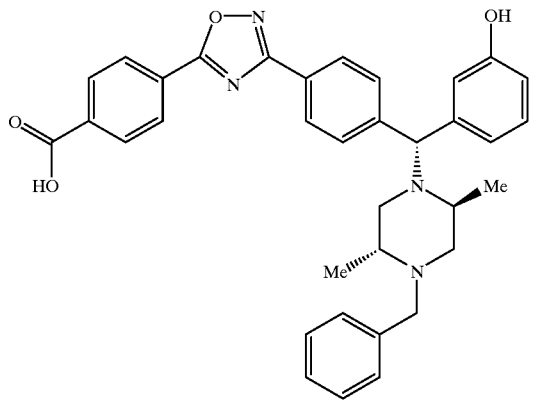

The title compound was prepared by a similar method to that described for Example 22 using the corresponding ester, Example 78 to afford the title compound as a white solid.

m/z 575 (MH$^+$).

$\delta_H$ (300 MHz, DMSO): 8.27 (2H, d), 8.18 (2H, d), 8.00 (2H, d), 7.60 (2H, d), 7.20 (5H, m), 7.10 (1H, m), 6.80–6.60 (3H, m), 5.00 (1H, s), 3.80 (1H, d), 3.20 (1H, d), 2.60 (4H, m), 2,00 (2H, m), 1.00 (6H, dd).

Analysis: Found C, 69.42; H, 6.02; N, 8.55; C$_{35}$H$_{34}$N$_4$O$_4$1.7H$_2$O requires C, 69.45 ;H, 6.23; N, 9.26%.

Example 80

Ethyl 3-(3-{3-[(R)-1-[(2S,5R-4-benzyl-2,5-dimethylhexahydropyrazin-1-yl]-1-(3-hydroxyphenyl)methyl]phenyl}-1,2,4-oxadiazol-5-yl)propanoate

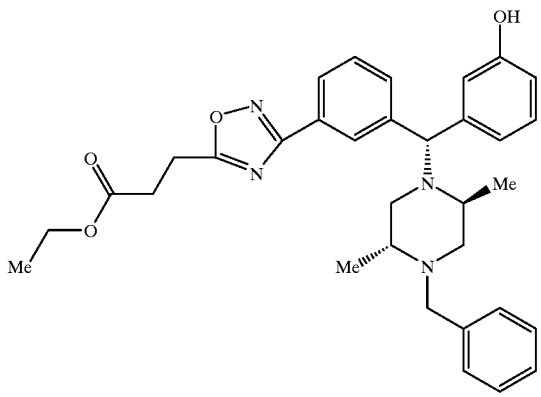

The title compound was prepared by a similar method to that described for Example 74 from the compound of Preparation 59 and ethyl succinylchloride.

R$_f$ 0.7 (CH$_2$Cl$_2$/MeOH, 9/1, v/v).

m/z 556 (MH$^+$).

Example 81

3-(3-{3-[(R)-1-[(2S,5R)-4-allyl-2,5-dimethylhexahydropyrazin-1-yl]-1-(3-hydroxyphenyl)methyl]phenyl}-1,2,4-oxadiazol-5-yl)propanoic acid

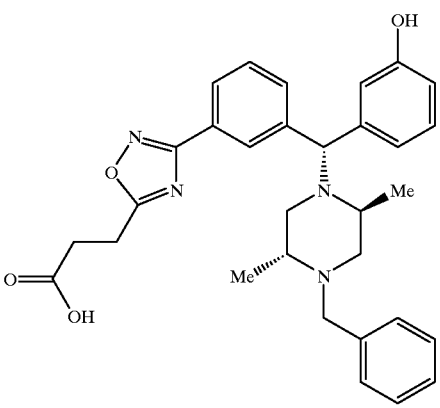

The title compound was prepared by a similar method to that described for Example 22 using the compound of Example 80 to afford the title compound as a white solid.

R$_f$ 0.13 (CH$_2$Cl$_2$/MeOH, 9/1, v/v).

m/z: 528 (MH$^+$).

$\delta_H$ (300 MHz, DMSO) 8.05 (1H, s), 7.80 (1H, d), 7.58 (1H, d), 7.45 (1H, t), 7.20 (5H, m), 7.10 (1H, t), 6.73 (1H, d), 6.70 (1H, s), 6.60 (1H, d), 4.96 (1H, s), 3.72 (1H, d), 3.50–3.10 (4H, m), 2.65 (4H, m), 2.30 (1H, d), 2.00 (2H, m), 1.02 (6H, m).

Analysis: Found C, 66.52; H, 6.62; N, 9.99; C$_{31}$H$_{34}$N$_4$O$_4$.1.8 H$_2$O requires C, 66.60; H, 6.78; N, 10.02%.

Example 82

Ethyl 4-(3-{3-[(R)-1-[(2S,5R)-4-benzyl-2,5-dimethylhexahydropyrazin-1-yl]-1-(3-hydroxyphenyl)methyl]phenyl}-1,2,4-oxadiazol-5-yl)butanoate

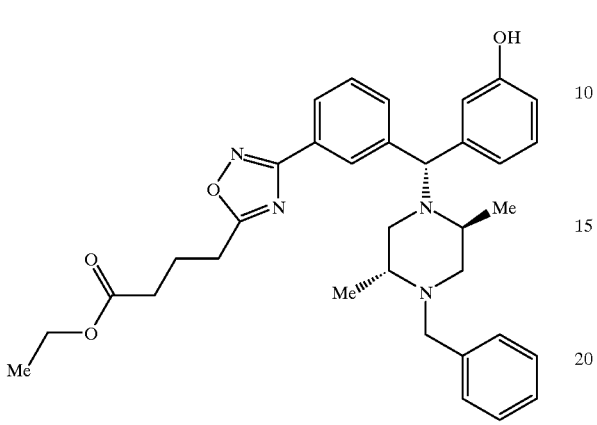

The title compound was prepared by a similar method to that described for Example 74 using the compound of Preparation 59 and ethyl glutarylchloride.

$R_f$ 0.24 ( $CH_2Cl_2$/MeOH, 95/5, v/v).

m/z: 568 (MH$^+$).

Example 83

4-(3-{3-[(R)-1-[(2S,5R)-4-benzyl-2,5-dimethylhexahydropyrazin-1-yl]-1-(3-hydroxyphenyl)methyl]phenyl}-1,2,4-oxadiazol-5-yl)butanoic acid

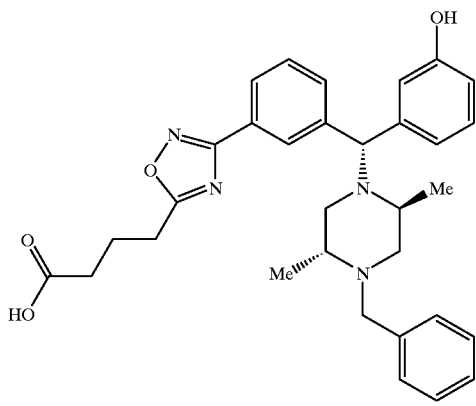

The title compound was prepared by a similar method to that described for Example 22 using the corresponding ester, Example 82 to afford the title compound as a white solid.

$R_f$ 0.1 ( $CH_2Cl_2$/MeOH, 9/1, v/v).

m/z: 541 (MH$^+$).

$\delta_H$ (400 MHz, DMSO) 8.05 (1H, s), 7.80 (1H, d), 7.60 (1H, d), 7.45 (1H, t0, 7.20 (5H, m), 7.10 (1H, t), 6.70 (2H, m), 6.60 (1H, d), 4.98 (1H, s), 3.72 (1H, d), 3.10 (1H, d), 3.00 (2H, t), 2.65 (4H, m), 2.35 (2H, t), 1.98 (4H, m), 1.02 (6H, m).

Analysis: Found C, 68.88; H, 6.83; N, 9.98; $C_{32}H_{36}N_4O_4 \cdot H_2O$ requires C, 68.80; H, 6.86; N, 10.03%.

Example 84

Ethyl 2-{5-[(R)-1-[(2S,5R)-4-allyl-2,5-dimethylhexahydropyrazin-1-yl]-1-(3-hydroxyphenyl)methyl]-1H-indol-1-yl} acetate

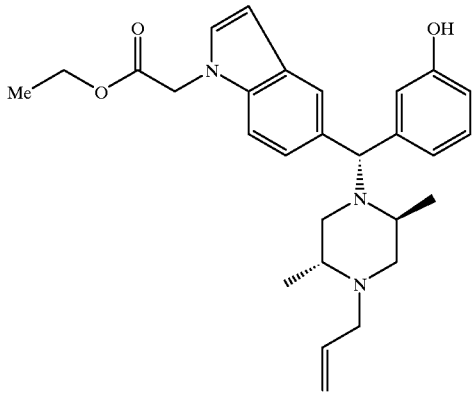

Tetraethylammonium fluoride (250 mg) was added to a solution of the compound of Preparation 62 (650 mg) in acetonitrile (10 ml). The reaction mixture was stirred for 5 mins and then poured into water and extracted with EtOAc (x3). The combined organic layers were washed with saturated brine, dried over MgSO$_4$ and evaporated under reduced pressure. The crude product was purified by column chromatography on silica gel eluting with $CH_2Cl_2$/MeOH/0.88NH$_3$ (97/3/1, v/v) to afford the title compound (330 mg).

$R_f$ 0.5 (solvent)

m/z: 462 (MH$^+$)

$\delta$ (CDCl$_3$): 7.68 (1H, s), 7.34 (1H, d), 7.16 (2H, m), 7.08 (1H, d), 6.80 (1H, d), 6.70 (1H, s), 6.65 (1H, d), 6.50 (1H, s), 5.92 (1H, m), 5.60 (1H, br s), 5.36–5.16 (3H, m), 4.82 (2H, s), 4.2 (2H, t), 3,40 (1H, dd), 2.98–2.80 (2H, m), 2.70 (2H, m), 2.54 (1H, m), 2.20 (1H, m), 2.00 (1H, m), 1.30 (3H, t), 1.20 (3H, d), 1.00 (3H, d).

Found: C, 72.48; H, 7.71; N, 8.85. $C_{28}H_{35}N_3O_3 \cdot 0.1H_2O$ requires C, 72.57; H, 7.66; N, 9.07

Example 85

2-{5-[(R)-1-[(2S,5R)-4-allyl-2,5-dimethylhexahydropyrazin-1-yl]-1-(3-hydroxyphenyl)methyl]-1H-indol-1-yl} acetic acid

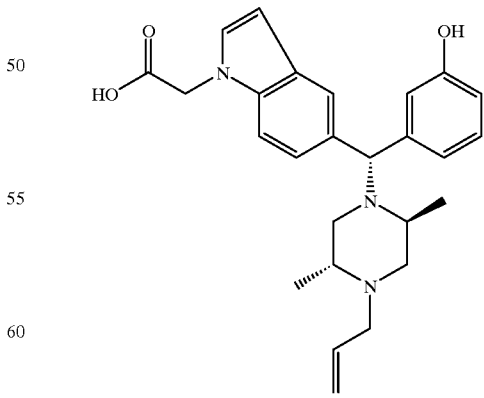

The title compound was prepared by a similar method to that described for Example 22 using the corresponding ester, Example 84 to afford the title compound as a white solid.

$R_f$ 0.3 (CH$_2$Cl$_2$/MeOH/0.88NH$_3$, 80/20/3, v/v).

m/z: 434 (MH$^+$)

δ(300 MHz, DMSO): 7.50 (1H, s), 7.25–7.00 (4H, m), 6.75 (2H, d), 6.60 (1H, d), 6.30 (1H, s), 5.85–5.70 (1H, m), 5.20–5.05 (2H, 2xd), 4.90 (3H, d), 3.10–3.20 (2H, m), 2.95 (1H, m), 2.70 (2H, m), 2,50 (1H, m), 2.30 (1H, s), 2.20 (1H, m), 1.95 (1H, m), 1.05 (3H, d), 0.95 (3H, d).

Example 86

5-{5-[(R)-1-[(2S,5R)-4-allyl-2,5-dimethylhexahydropyrazin-1-yl]-1-(3-hydroxyphenyl)methyl]-1H-indol-1-yl} pentanoic acid

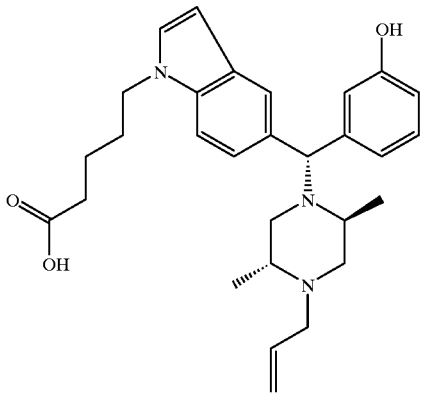

The title compound was prepared from the corresponding ethyl ester using a method similar to that described for Example 22 affording the title compound as a white solid.

$R_f$ 0.35 ( CH$_2$Cl$_2$/MeOH/0.88NH$_3$, 80/20/3, v/v).

m/z: 476 (MH$^+$).

δ$_H$ (400 MHz, DMSO) 7.50 (1H, s), 7.35 (1H, d), 7.30 (1H, d), 7.20 (1H, d), 7.10 (1H, t), 6.80 (2H, m), 6.60 (1H, m), 6.32 (1H, s), 5.85–5.70 (1H, m), 5.20–5.05 (2H, 2xd), 4.90 (1H, s), 4.10 (2H, t), 3.10 (2H, m), 2.90 (1H, m), 2.75–2.60 (2H, m), 2.55 (1H, m), 2.20–2.00 (4H, m), 1.75 (2H, m), 1.45 (2H, m), 1.10 (3H, d), 0.95 (3H, d).

Analysis: Found C, 70.56; H, 7.65; N, 8.73; C$_{29}$H$_{37}$N$_3$O$_3$.1 H$_2$O requires C, 70.55; H, 7.96; N, 8.51%.

The precursors to the above compound were prepared from the aldehyde of Preparation 88 and Ethyl-5-bromovalerate and thereafter following similar methods that were used in the Preparation of Example 46.

Example 87

5-{5-[(R)-1-[(2S,5R)-4-benzyl-2,5-dimethylhexahydropyrazin-1-yl]-1-(3-hydroxyphenyl)methyl]-1H-indazol-1-yl} pentanoic acid

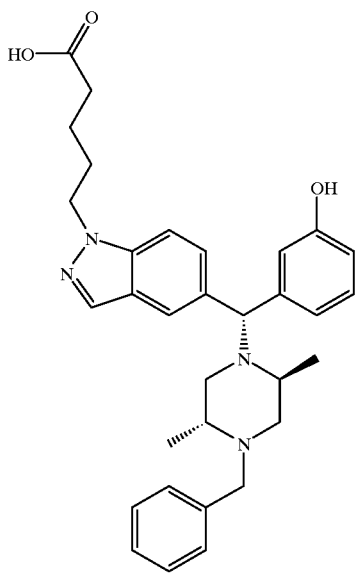

Tetraethyl ammonium fluoride (313 mg) was added to a stirred solution of the compound of Preparation 65 (935 mg) in acetonitrile (25 ml). The reaction mixture was stirred for 30 mins at room temperature and evaporated under reduced pressure the residue was partitioned between EtOAc/sodium hydrogen carbonate. The organic layer was separated dried over MgSO$_4$ and evaporated under reduced pressure, the residue was dissolved in dioxan/MeOH (1/1, 40 ml ) and 2N NaOH (3.5 ml ) added the reaction mixture was stirred at room temperature for 1 hr. 5N NaOH (3 ml) was then added the mixture was stirred for a further 1 hr after which time the solution was acidified to pH 2.0 with 5N HCl and immediately re-basified to pH 9.0 with 0.88NH$_3$. The solution was preabsorbed onto silica gel and evaporated under reduced pressure. The crude product was purified by column chromatography on silica gel eluting with CH$_2$Cl$_2$/MeOH/0.88NH$_3$ (80/20/3, v/v). The product was further purified on polystyrene reverse phase resin eluting with a elution gradient of H$_2$O/Acetonitrile (90/10–10/90). The acetonitrile was evaporated under reduced pressure and the remaining aqueous solution was frozen and lyophilised to afford the title compound as a white solid (535 mg).

$R_f$ 0.17 ( CH$_2$Cl$_2$/MeOH/0.88NH$_3$, 80/20/3).

m/z: 527 (MH$^+$).

δ$_H$ (300 MHz, DMSO) 7.97 (1H, s), 7.68 (1H, s), 7.55 (1H, d), 7.42 (1H, d), 7.23 (5H, m), 7.10 (1H, t), 6.75 (2H, m), 6.60 (1H, d), 4.95 (1H, s), 4.33 (2H, t), 3.73 (1H, d), 3.28 (1H, d), 2.65 (4H, m), 2.17 (2H, m), 1.99 (2H, m), 1.79 (2H, m), 1.42 (2H, m), 1.01 (6H, m).

Analysis: Found C, 70.72; H, 7.44; N, 10.67; C$_{32}$H$_{38}$N$_4$O$_3$. H$_2$O requires C, 70.56; H, 7.40; N, 10.29%.

[α]$_D$ –17.2°, c=0.1/methanol.

Example 88

2-{5-[(R)-1-[(2S,5R)-4-benzyl-2,5-dimethylhexahydropyrazin-1-yl]-1-(3-hydroxyphenyl)methyl-1H-indazol-1-yl} acetic acid

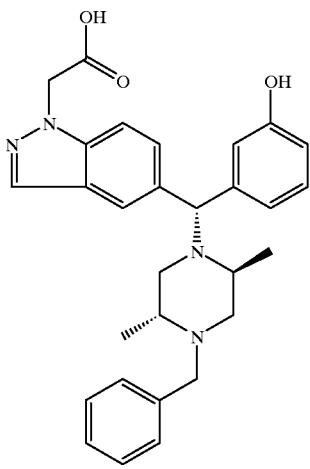

The title compound was prepared and purified by a similar method to that described for Example 87 from the corresponding ester to afford a white solid.

$R_f$ 0.31 ( $CH_2Cl_2$/MeOH/0.88$NH_3$, 80/20/3, v/v).

m/z: 485 (MH$^+$).

$\delta_H$ (400 MHz, MeOD): 7.92 (1H, s), 7.70 (1H, s), 7.43 (7H, m), 7.18 (1H, t), 6.77 (3H, m), 5.26 (1H, bs), 4.96 (2H, s), 4.43 (1H, m), 3.93 (1H, d), 3.25 (1H, m), 3.05 (1H, m), 2.80 (3H, m), 2.29 (1H, m), 1.34 (3H, d), 1.18 (3H, d).

Analysis: Found C, 68.12; H, 6.86; N, 10.94; $C_{29}H_{32}N_4O_3$. 1.5 $H_2O$ requires C, 68.08; H, 6.90: N, 10.95%.

$[\alpha]_D$ –20.2°, c=0.8/methanol.

The precursors to the above compound were prepared from the aldehyde of Preparation 98 and Ethyl bromoacetate and thereafter following similar methods that were used in the Preparation of Example 50.

Example 89

2-{5-[(R)-1-[(2S,5R)-4-benzyl-2,5-dimethylhexahydropyrazin-1-yl]-1-(3-hydroxyphenyl)methyl]-1H-indole-1-yl} acetic acid

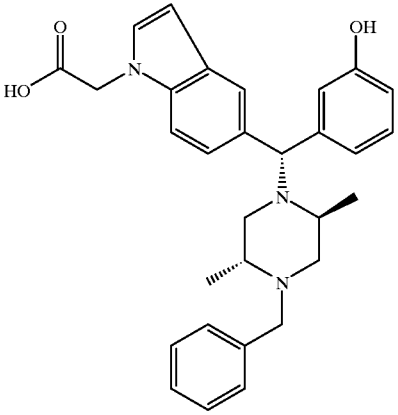

The title compound was prepared and purified by the method of Example 87 from the compound of Preparation 66 to afford the title compound as a white solid.

$R_f$ 0.23 ($CH_2Cl_2$/MeOH/0.88$NH_3$, 80/20/3, v/v).

m/z: 484 ((MH$^+$).

$\delta_H$ (400 MHz, DMSO): 9.20 (1H, bs), 7.50 (1H, s), 7.21 (8H, m), 7.07 (1H, m), 6.75 (2H, m), 6.57 (1H, m), 6.34 (1H, s), 4.87 (3H, s), 3.70 (1H, d), 3.30 (1H, d), (4H,2.64 m), 2.02 (2H, m), 1.02 (6H, m).

Analysis: Found C, 71.83; H, 7.08; N, 8.57; $C_{30}H_{33}N_3O_3 \cdot H_2O$ requires C, 71.83; H, 7.03; N, 8.38%.

$[\alpha]_D$ –18.2°, c=0.1/methanol.

Example 90

2-{5-[(R)-1-[(2S,5R)-4-benzyl-2,5-dimethylhexahydropyrazin-1-yl]-1-(3-hydroxyphenyl)methyl]-1H-indole-1-yl} pentanoic acid

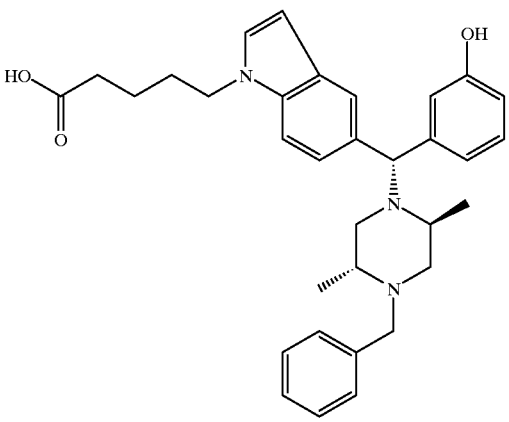

The title compound was prepared and purified by a similar method to that described for Example 87 from the corresponding ester to afford the title compound as a white solid, $R_f$ 0.28 ($CH_2Cl_2$/MeOH/0.88$NH_3$, 80/20/3, v/v).

m/z 526 (MH$^+$).

$\delta_H$ (300 MHz, DMSO): 7.51 (1H, s), 7.32 (6H, m), 7.20 (2H, m), 7.08 (1H, d), 6.78 (2H, m), 6.58 (1H, d), 6.33 (1H, d), 4.87 (1H, bs), 4.12 (2H, t), 3.69 (1H, d), 3.31 (1H, d), 2.68 (4H, m), 2.19 (2H, t), 2.03 (2H, m), 1.61 (2H, m), 1.43 (2H, m), 1.02 (6H, m).

Analysis: Found C, 73.36; H, 7.60; N, 7.79; $C_{33}H_{39}N_3O_3$. 0.75 $H_2O$; requires C, 73.51; H, 7.57; N, 7.79%.

$[\alpha]_D$ −20.70°, c=0.11/methanol.

The precursors to the above compound were prepared from the aldehyde of Preparation 88 and 5-Ethyl bromovalerate and thereafter following similar methods that were used in the Preparation of Example 52.

Example 91 and 92

Ethyl 5-[(R)-1-[(2S,5R)-4-benzyl-2,5-dimethylhexahydropyrazin-1-yl]-1-(3-hydroxyphenyl)methyl]-1-ethyl-1H-indol-1-yl-carboxylate and Ethyl 5-[(S)-1-[(2S,5R)-4-benzyl-2,5-dimethylhexahydropyrazin-1-yl]-1-(3-hydroxyphenyl)methyl]-1-ethyl-1H-indol-1-yl-carboxylate

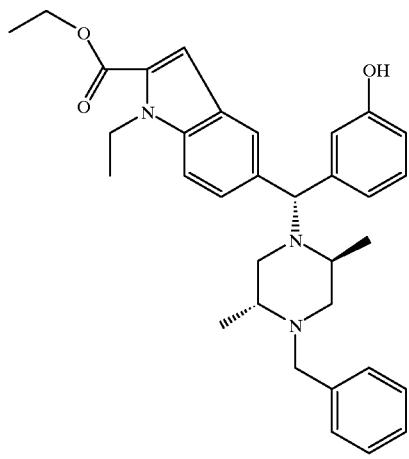

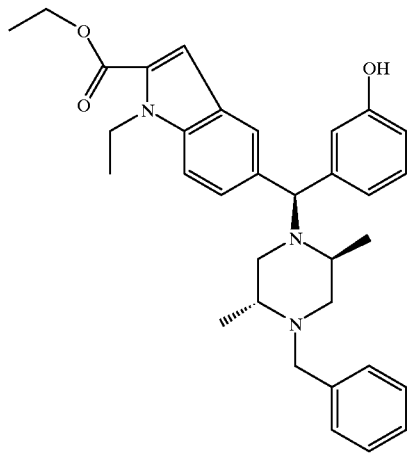

The title compound was prepared by a similar method to that described for Preparation 4 using the compound of Preparation 68, (−)-(2R,5S)-1-benzyl-2,5-dimethylpiperazine, benzotriazole and 3-trimethylsilyloxyphenylmagnesium bromide. The crude product was purified by column chromatography on silica gel eluting with Hexane/Isopropanol/ 0.88$NH_3$ (95/5/0.25, v/v) to afford the separated pure diasteromers.

Example 91

$R_f$ 0.29 (Hexane/Isopropanol/0.88$NH_3$, 90/10/0.75).

m/z: 526 (MH$^+$).

$\delta_H$ (300 MHz, CDCl$_3$): 7.70 (1H, s), 7.48–7.15 (8H, m), 6.90 (2H, m), 6.72 (2H, m), 5.15 (1H, s), 4.80 (1H, bs), 4.60 (2H, q), 4.38 (2H, q), 3.90 (1H, d), 3.25 (1H, d), 2.70 (4H, m), 2.08 (2H, m), 1.40 (6H, m), 1.10 (6H, m).

Example 92

$R_f$ 0.29 (Hexane/Isopropanol/0.88$NH_3$, 90/10/0.75).

m/z: 526 (MH$^+$).

$\delta_H$ (300 MHz, CDCl$_3$): 7.70 (1H, s), 7.48–7.15 (8H, m), 6.90 (2H, m), 6.72 (2H, m), 5.17 (1H, s), 4.60 (1H, bs), 4.40 (2H, q), 4.38 (2H, q), 3.98 (1H, d), 3.29 (1H, d), 2.70 (4H, m), 2.05 (2H, m), 1.40 (6H, m), 1.15 (3H, d), 1.05 (3H, d).

Example 93

5-[(R)-1-[(2S,5R)-4-benzyl-2,5-dimethylhexahydropyrazin-1-yl]-1-(3-hydroxyphenyl)methyl]-1-ethyl-1H-indole-2-carboxylic acid

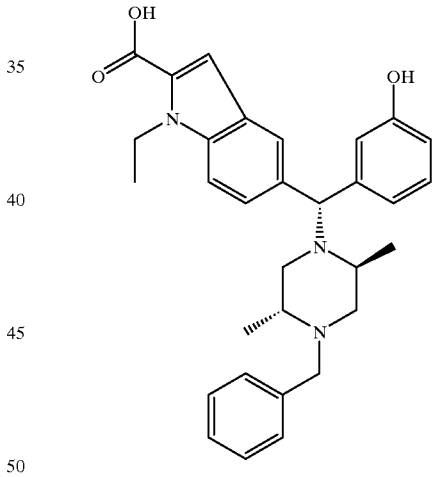

The title compound was prepared by the method of Example 22 from corresponding ester, Example 91 to afford the title compound as a solid.

$R_f$ 0.30 ( $CH_2Cl_2$/MeOH/0.88$NH_3$, 80/20/3, v/v)

Mpt: 172–176° C.

$\delta_H$ (400 MHz, DMSO): 12.24 (1H, bs), 9.23 (1H, s), 7.61(1H, s), 7.50 (1H, d), 7.40 (1H, d), 7.35–7.05 (7H, m), 6.77 (2H, m), 6.58 (1H, d), 4.91(1H, s), 4.55 (2H, q), 3.72 (1H, d), 3.35 (1H, d), 2.69 (4H, m), 2.05 (2H, m), 1.22 (3H, t), 1.02 (6H, m,).

Analysis: Found C, 71.86; H, 7.18; N, 7.95; $C_{31}H_{35}N_3O_3$.1.25 $H_2O$ requires C, 71.58; H, 7.27; N, 8.08%.

$[\alpha]_D$ −25.7°, c=0.11/DMSO.

Example 94

5-[(S)-1-[(2S,5R)-4-benzyl-2,5-dimethylhexahydropyrazin-1-yl]-1-(3-hydroxyphenyl)methyl]-1-ethyl-H-indole-2-carboxyllic acid

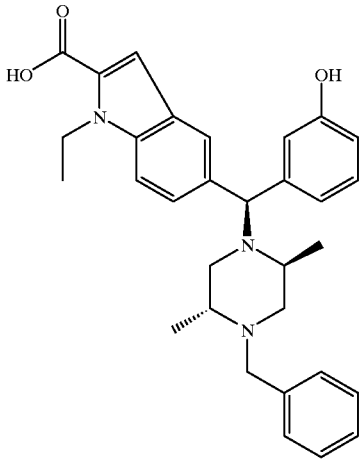

The title compound was prepared by the method of Example 22 from corresponding ester, Example 92 to afford the title compound as a white solid.

$R_f$ 0.30 (CH$_2$Cl$_2$/MeOH/0.88NH$_3$, 80/20/3, v/v)

Mpt: 170–175° C.

$\delta_H$ (400 MHz, DMSO): 9.27 (1H, bs), 7.60 (1H, s), 7.48 (1H, d), 7.37 (1H, d), 7.28 (4H, m), 7.19 (1H, m), 7.07 (2H, m), 6.76 (2H, m), 6.59 (1H, d), 4.90 (1H, s), 4.55 (2H, q), 3.70 (1H, d), 3.30 (1H, d), 2.67 (4H, m), 2.03 (2H, m), 1.25 (3H, t), 1.03 (6H, m).

Analysis: Found C, 71.65; H, 7.23; N, 8.05; C$_{31}$H$_{35}$N$_3$O$_3$.1.25 H$_2$O requires C, 71.58; H 7.27; N, 8.08%.

$[\alpha]_D$−16.0°, c=0.1/DMSO.

Example 95

2-{6-[(R)-1-[(2S,5R)-4-benzyl-2,5-dimethylhexahydropyrazin-1-yl]-1-(3-hydroxyphenyl)methyl]-1H-indole-1-yl} acetic acid

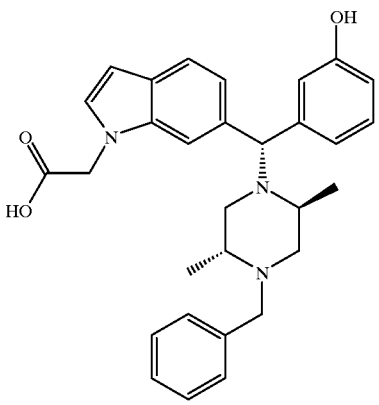

The title compound was prepared and purified by the method of Example 87 from the product of Preparation 71 to afford a solid.

$R_f$ 0.2 ( CH$_2$Cl$_2$/MeOH/0.88NH$_3$, 90/10/1, v/v).

$\delta_H$ (400 MHz, DMSO): 9.20 (1H, bs), 7.40 (2H, d), 7.25 (5H, m), 7.20 (H, m), 7.01 (2H, m), 6.80 (2H, m), 6.55 (1H, d), 6.30 (1H, s), 4.95 (2H, d), 4.78 (1H, s) 360 (1H, d), 3.20 (1H, m), 2.80–2.60 (4H, m), 2.05 (2H, m), 1.05 (3H, d), 0.95 (3H, d).

Analysis Found C, 73.27; H, 6.94; N, 8.55; C$_{30}$H$_{33}$N$_3$O$_3$.0.45 H$_2$O requires C, 73.26; H, 6.93; N, 8.55%.

Solubility 6 mg/1 ml dmso.

$[\alpha]_D$+9.0°, c=0.1/DMSO

Example 96

2-{6-[(R)-1-[(2S,5R)-4-benzyl-2,5-dimethylhexahydropyrazin-1-yl]-1-(3-hydroxyphenyl)methyl]-1H-indole-1-yl} pentanoic acid

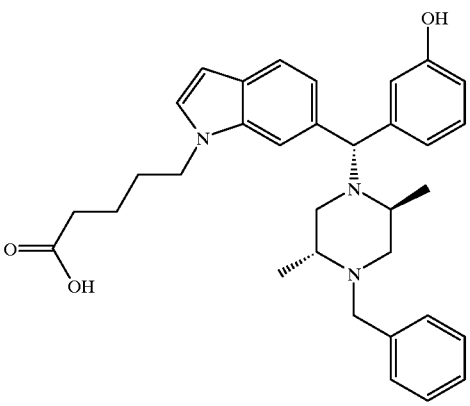

The title compound was prepared and purified by the method of Example 87 from the corresponding ethyl ester to afford the title compound as a white solid.

$R_f$ 0.65 (CH$_2$Cl$_2$/MeOH/0.88NH$_3$, 80/20/4, v/v)

m/z: 526 (MH$^+$).

$\delta_H$ (400 MHz, DMSO): 7.50 (1H, s), 7.40 (1H, d), 7.25 (5H, s), 7.20 (1H, m), 7.00 (2H, m), 6.80 (2H, m), 6.55 (1H, d), 6.25 (1H, s), 4.90 (1H, s), 4.05 (2H, t), 3.63 (1H, d), 3.03 (1H, d), 2.75–2.60 (4H, m), 2.20 (2H, t), 2.05 (2H, m), 1.75 (2H, m), 1.40 (2H, m), 1.05 (3H, d), 0.95 (3H, d).

Analysis: Found C, 72.72; H, 7.60; N, 7.73; C$_{33}$H$_{39}$N$_3$O$_3$.H$_2$O requires C, 72.64; H, 7.48; N, 8.17%.

$[\alpha]_D$−8.00°, c=0.1/methanol.

The precursors to the above compound were prepared from the aldehyde of Preparation 105 and 5-Ethyl bromovalerate and thereafter following similar methods that were used in the Preparation of Example 56.

Example 97

5-{4-[(R)-1-[(2S,5R)-4-benzyl-2,5-dimethylhexahydropyrazin-1-yl]-1-(3-hydroxyphenyl)methyl]phenyl} nicotinic acid

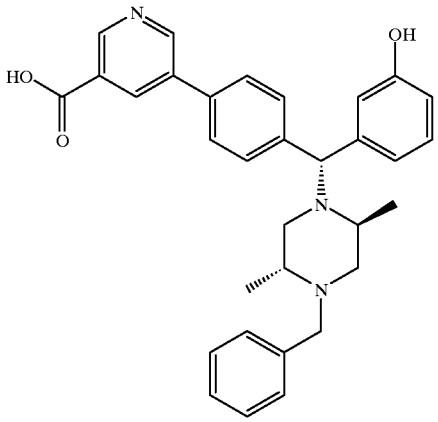

The title compound was prepared and purified by the method of Example 60 from the compound of Preparation 74 to afford the product as a white solid.

m/z: 508 (MH$^+$). $\delta_H$ (400 MHz, DMSO): 8.90 (1H, s), 8.80 (1H, s), 8.30 (1H, s), 7.65 (2H, d), 7.50 (2H, d), 7.30–7.10 (6H, m), 6.80–6.60 (3H, m), 4.95 (1H, s), 3.75 (1H, d), 3.20 (1H, d), 2.65 (4H, m), 2.00 (2H, m), 1.05 (6H, 2xd).

Analysis: Found C, 66.20; H, 6.64; N, 6.87; $C_{32}H_{33}N_3O_3 \cdot 4 H_2O$ requires C, 66.30; H, 7.13; N, 7.25%.

Example 98

3-({5-[(R)-[(2S,5R)-4-benzyl-2,5-dimethylpiperazinyl](3-methoxyphenyl)methyl]-1,3-dihydro-2H-isoindol-2-yl}methyl)benzoic acid

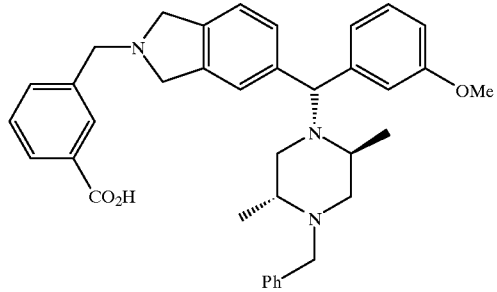

To a solution of the compound of Preparation 79 250 mg) in dry THF (20 ml) was added potassium carbonate (400 mg) and methyl 3-bromomethylbenzoate (156 mg). The reaction mixture was heated under reflux for 2 hours. The mixture was cooled to room temperature and methanol (20 ml) and sodium hydroxide (5 ml, 2N aqueous solution) added. The mixture was heated for a further 2 hours, cooled to room temperature, acidified with hydrochloric acid (2N aqueous solution). The pH of the solution was adjusted with ammonium hydroxide solution and evaporated to dryness in vacuo. The residue was purified by column chromatography over silica gel (dichloromethane:methanol:ammonium hydroxide; 84:14:2) to afford the title compound, 127 mg.

m/z: 576 (MH$^+$)

Example 99

3-({5-[(R)-[(2S,5R)-4-benzyl-2,5-dimethylpiperazinyl](3-hydroxyphenyl)methyl]-1,3-dihydro-2H-isoindol-2-yl}methyl)benzoic acid

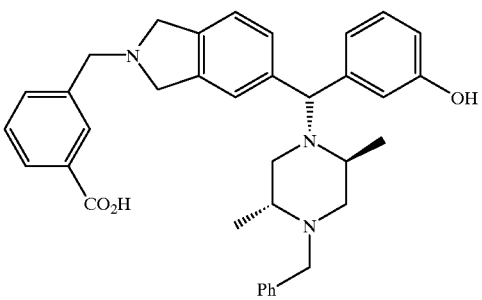

Boron tribromide (800 ml of 1N solution in dichloromethane) was added to a stirred solution of the compound of Example 98 (106 mg). The resulting white precipitate was stirred at room temperature for 2 hours. The reaction was quenched with methanolic ammonium hydroxide (1:1 v/v) and evaporated to dryness in vacuo. The residue was purified by column chromatography over silica gel (dichloromethane:methanol:ammonium hydroxide; 84:14:2) to afford the title compound, 36.5 mg.

m/z: 576 (MH$^+$)

Example 100

2-({5-[(R)-[(2S,5R)-4-benzyl-2,5-dimethylpiperazinyl](3-methoxyphenyl)methyl]-1,3-dihydro-2H-isoindol-2-yl}carbonyl)benzoic acid

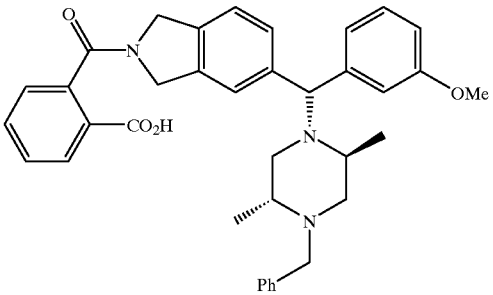

To a solution of the compound of Preparation 79 (250 mg) in dry THF (10 ml) was added phthalic anhydride (84 mg). The reaction mixture was heated under reflux for 2 hours. The mixture was cooled to room temperature evaporated to dryness in vacuo. The residue was purified by column chromatography over silica gel (dichloromethane: methanol:ammonium hydroxide; 84:14:2) to afford the title compound, 200 mg.

m/z: 442 (M-[C$_8$H$_5$O$_3$]$^+$)

$\delta_H$ (400 MHz, d$_6$-DMSO): 8.00 (1H, t), 7-60-6.70 (15H, m), 5.05 (1H, br s), 4.80 (3H, s), 4.40 (2H, d), 4.15 (1H, m), 3.70 (3H, m), 3.60 (1H, m), 2.90–2.60 (4H, m), 2.40–2.00 (2H, m), 1.18 (3H, d), 1.08 (3H, m).

Example 101 methyl 3-(3-{4-[(R)-[(2S,5R)-4-benzyl-2,5-dimethylpiperazinyl](3-methoxyphenyl)methyl]phenyl}-1-azetidinyl)propanoate

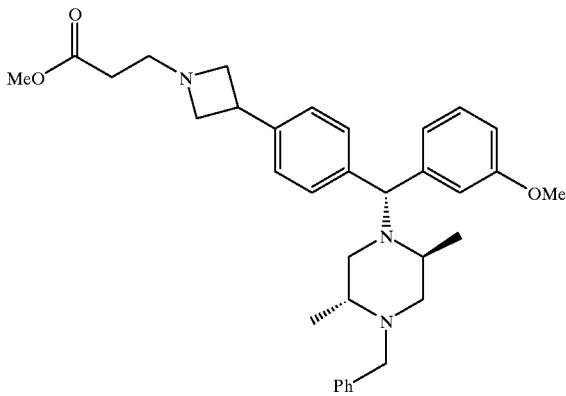

The compound of Preparation 82 (237 mg), potassium carbonate (215 mg) and methyl 2-bromopropionate (63 ml) in dry acetonitrile (25 ml ) was stirred at room temperature for 18 hours. The reaction mixture was evaporated to dryness and the residue partitioned between ethyl acetate and water. The organic layer was separated, dried ($Na_2SO_4$) and evaporated to dryness in vacuo. The residue was purified by column chromatography over silica gel (pentane:isopropanol:ammonium hydroxide; 95:5:0.5) to afford the title compound, 128 mg.

m/z: 542 ($MH^+$)

$R_f$: 0.60 (pentane:isopropanol:ammonium hydroxide; 90:10:0.75)

$\delta_H$ (400 MHz, $CDCl_3$): 7.40 (2H, d), 7.33–7.14 (8H, m), 6.80 (3H, m), 5.07 (1H, s), 3.90 (1H, d), 3.80–3.63 (9H, m), 3.22 (1H, d), 3.12 (2H, m), 2.82–2.52 (6H, m), 2.40 (2H, t), 2.01 (2H, m), 1.08 (6H, d).

Example 102

3-(3-{4-[(R)-[(2S,5R)-4-benzyl-2,5-dimethylpiperazinyl](3-methoxyphenyl)methyl]phenyl}-1-azetidinyl)propanoic acid

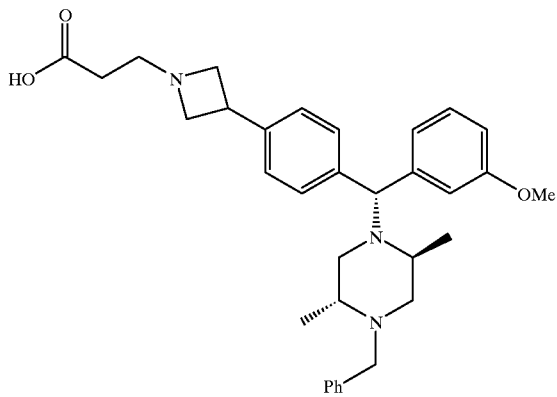

The compound of example 101 (128 mg) was dissolved in methanol (6 ml) and dioxane (6 ml) and sodium hydroxide added (1ml of 5N solution). The reaction mixture was stirred at room temperature for 2 hours. The reaction mixture was acidified with glacial acetic acid and immediately basified to pH9 with ammonium hydroxide. The organic solvents were removed in vacuo and the remaining aqueous solution layered onto reverse phase polystyrene gel column. The column was eluted with water/acetonitrile (100:0 to 0:100 in 100 ml 20% increments). The aqueous solution was freeze-dried to afford the title compound, 111 mg as a white solid.

m/z: 528 ($MH^+$)

m.p.: 93–96° C.

$R_f$ : 0.17 (dichloromethane:methanol:ammonium hydroxide; 80:20:3)

$\delta_H$ (400 MHz, $CDCl_3$): 7.42 (2H, d), 7.33–7.12 (8H, m), 6.79 (3H, m), 5.04 (1H, s), 4.08 (2H, t), 3.88 (2H, d), 3.78 (3H, s), 3.42 (2H, t), 3.02 (1H, m), 2.96 (3H, t), 2.57 (4H, m), 2,40 (2H, t), 2.00 (2H, m), 1.08 (6H, d).

Example 103

3-(3-{4-[(R)-[(2S,5R)-4-benzyl-2,5-dimethylpiperazinyl](3-hydroxyphenyl)methyl]phenyl}-1-azetidinyl)propanoic acid

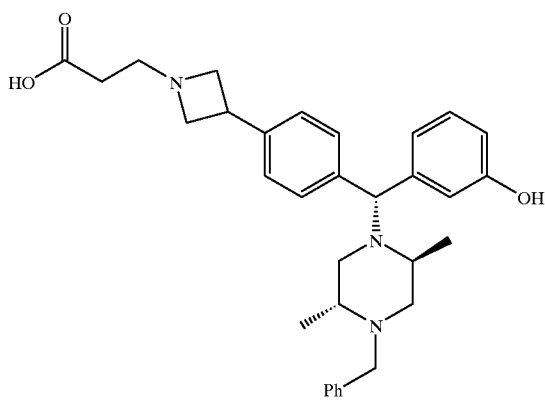

Boron tribromide (462 ml of 1N solution in dichloromethane) was added to a stirred solution of the compound of example 102 (61 mg). The resulting white precipitate was stirred at room temperature for 1 hours. The reaction was quenched with methanolic ammonium hydroxide (1:1 v/v) and evaporated to dryness in vacuo. The residue was purified by column chromatography over silica gel (dichloromethane:methanol:ammonium hydroxide; 80:20:3) to afford the title compound, 42.4 mg.

m/z: 514 ($MH^+$)

$R_f$ : 0.16 (dichloromethane:methanol:ammonium hydroxide; 80:20:3)

m.p.: 142–5° C.

$\delta_H$ (400 MHz, $d_6$-DMSO): 7.35–7.15 (9H, m), 7.08 (1h, t), 6.72 (2H, m), 6.61 (1H, m), 4.80 (1H, s), 3.70 (1H, d), 3.58 (3H, m), 3.27 (1H, d), 3.07 (2H, t), 2.61 (6H, m), 2.18 (3H, t), 1.95 (2H, m), 1.00 (6H, 2xd).

Example 104

Methyl 2-[7-[(R)-[(2S, 5R)-4-benzyl-2,5-dimethylpiperazinyl](3-methoxyphenyl)methyl]-3,4-dihydro-2(1H)-isoquinolinyl]acetate

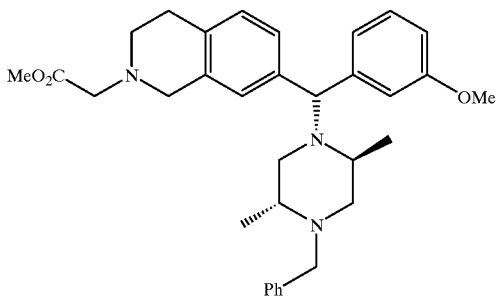

To a solution of the compound of Preparation 92 (1.0 g) in N,N-dimethylformamide (20 ml) was added potassium carbonate (1.22 g) and methyl bromoacetate (0.172 ml) and the reaction heated at 50° C. for 16 hours. The reaction was cooled, water (50 ml) added and the mixture extracted with ethyl acetate (x3). The combined organics were dried (MgSO$_4$), filtered and the solvent removed under reduced pressure. The crude product was purified on silica eluting with dichloromethane:methanol (97.5:2.5) to give the title compound (0.87 g).

MS m/z 529 (MH)$^+$.

$^1$H-NMR (CDCl$_3$): δ=1.06 (6H, m), 2.00 (2H, m), 2.50–2.73 (4H, m), 2.87 (4, m), 3.22 (1H, d), 3.42 (2H, s), 3.74–3.80 (8H, m), 3.97 (1H, d), 4.99 (1H, s), 6.95–7.05 (3H, m), 7.00 (1H, d), 7.07 (1H, s), 7.20 (3H, m), 7.27 (4H, m).

Example 105

2-[7-[(R)-[(2S,5S)-4-benzyl-2,5-dimethylpiperazinyl](3-methoxyphenyl)methyl]-3,4-dihydro-2(1H)-isoquinolinyl]acetic acid

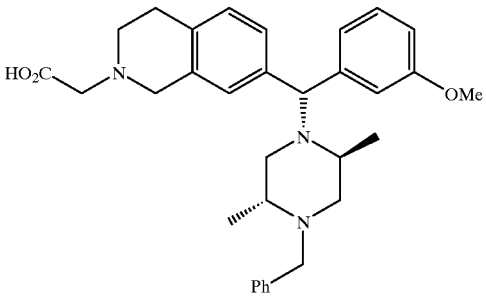

To a solution of the compound of Example 104 (0.85 g) in dioxan (20 ml) and methanol (10 ml) was added an aqueous solution of sodium hydroxide (2N, 5 ml). After 16 hours, the pH of the reaction was adjusted to pH5 using 1N aqueous hydrochloric acid solution and the solvent removed under reduced pressure. The crude product was purified on silica gel, eluting with a solvent gradient of 90:10:2 to 80:20:3 dichloromethane: methanol:ammonia solution. The fractions containing the product were pooled and the solvent removed under reduced pressure. The residue was taken up in a mixture of water and 1 drop of aqueous ammonium hydroxide solution and freeze-dried to give the title compound (0.65 g, 65%).

MS m/z 515 (MH)$^+$.

$^1$H-NMR (CDCl$_3$): δ=0.97 (3H, d), 1.03 (3H, d), 1.99 (2H, m), 2.53–2.83 (8, m), 3.19 (2H, m), 3.29 (1H, d), 3.44–3.90 (6H, m), 4.79 (1H, s), 6.74–7.26 (12H, m).

Example 106

2-[7-[(R)-[(2S,5S)-4-benzyl-2,5-dimethylpiperazinyl](3-hydroxyphenyl)methyl]-3,4-dihydro-2(1H)-isoquinolinyl]acetic acid

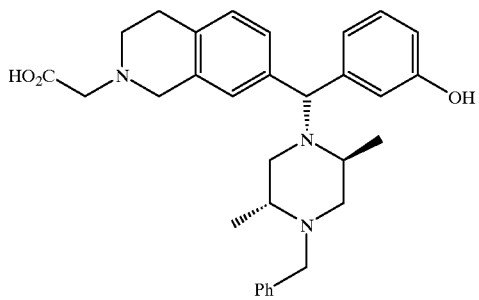

To a solution of the compound of Example 105 (0.34 g) in dichloromethane (20 ml ) at —78° C. was added boron tribromide (2.6 ml ). the reaction was allowed to warm to room temperature. After 2 hours, the reaction was quenched with ammoniacal methanol solution and the solvent removed under reduced pressure. The crude material was purified on silica eluting with 80:20:3 dichloromethane:methanol:ammonium hydroxide. The product containing fractions were pooled and the solvent removed under reduced pressure. The solid was purified further using MCI gel chromatography eluting with a solvent gradient of 100:0 to 0:100 water:methanol. The product-containing fractions were concentrated, a small volume of concentrated ammonium hydroxide added and the solution freeze-dried to give the title compound (0.11 g).

MS m/z 500 (MH)$^+$.

$^1$H-NMR (d$_6$-DMSO): δ=0.97 (3H, d), 1.04 (3H, d), 1.98 (2H, m), 2.54–2.70 (4H, m), 2.70–2.85 (4H, m), 3.22–3.32 (3H, m), 3.63–3.73 (3H, m), 4.73 (1H, s), 6.59 (1H, d), 6.65–6.74 (2H, m), 6.97–7.27 (9H, m).

PREPARATIONS

In the following Preparations, Preparation 31 is a further example of a useful pharmaceutically active compound according to the present invention.

Preparation 1

(−)-(2R,5S)-1-allyl-2,5-dimethylpiperazine and (+)-(2S,5R)-1-allyl-2,5-dimethylpiperazine

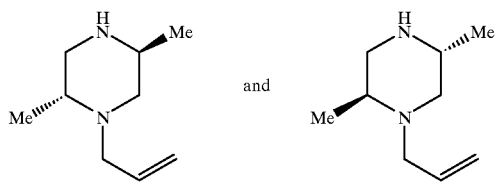

Trans-2,5-dimethylpiperazine (600 g), slurried in toluene (1200 ml), was heated to 85° C. with stirring, at which temperature, the solid dissolved completely. The solution was allowed to cool to room temperature gradually, with stirring, allowing slow precipitation of the solid, then cooled to 10° C. using an ice bath. The solid was filtered, washed with fresh, cold toluene (250 mls), and dried under vacuum (50° C.) overnight to yield a yellow crystalline solid (518.5 g).

Recrystallised trans-2,5-dimethylpiperazine (259.5 g) was slurried in cyclohexane (2.59 1) at room temperature. Sodium hydroxide solution (5M; 500 ml) was added in one go with tetrabutylammonium chloride (4.3 g) and the reaction mixture was stirred whilst the allyl bromide solution (302.4 g) in cyclohexane (300 ml) was added in a stream, over approximately 30 mins. The temperature of the reaction mixture rose slowly to 33° C. over 30 mins, and was stirred for a further 1 hr. T.l.c analysis showed that the organic phase contained mostly mono-allylated product, with traces of bis-allylated impurity and starting material. The aqueous contained mostly starting material and some mono-allylated product. The two phases were separated and the aqueous was stirred with fresh cyclohexane (2.5L). Allyl bromide (82.5 g) in cyclohexane (100 ml), and sodium hydroxide solution (5M, 136 ml) were added, and the mixture was stirred at room temperature for 1 hr. The phases were separated and the two cyclohexane phases were combined. The cyclohexane phase was backwashed with NaOH (1M, 200 ml) to remove traces of starting material and this wash was added to the aqueous layer and kept on one side. The organic extracts (containing only mono- and bis- allylated material) were stirred with water (1.5L), and the pH of the mixture adjusted to precisely 8.0 using c.HCl. TLC showed the aqueous contained mono with a faint trace of bis. Organic contained bis with a faint trace of mono. The layers were separated, and the pH of the aqueous adjusted to 13.5 using NaOH (10M), and extracted with Dichloromethane (4×1L). The previously held-back aqueous washings were extracted with Dichloromethane (4×1L). The combined organic extracts were dried over $MgSO_4$ and stripped (50° C.) to yield racemic 1-allyl-2,5-dimethylpiperazine as a yellow, mobile oil (278.9 g, 80%). [$R_f$ =0.4, (Dichloromethane/Methanol/ammonium hydroxide; 80:20:1)]

A solution of racemic 1-allyl-2,5-dimethylpiperazine (537.7 g) in acetone (1075 ml) was added in one portion to a stirred solution of (1R,3S)-(+)-camphoric acid in acetone (5.2L) at 40° C. Strirring was continued at 40° C. and a white precipitate began to form after approximately five minutes, which soon became very thick. The reaction mixture was stirred at gentle reflux for a further 1 hr before being cooled to 10° C. in an ice bath, and filtered. The precipitate was slurry-washed with fresh acetone (2L), then washed on the filter pad with more acetone (1L). The camphoric acid salt of (+)-(2S,5R)-1-allyl-2,5-dimethylpiperazine was dried under vacuum (60° C.) overnight to yield a white solid (577 g).

The crude enriched (−)-(2R,5S)-1-allyl-2,5-dimethylpiperazine (185.5 g) was redissolved in acetone (370 ml) and added to a solution of di-p-tolyl-D-tartaric acid monohydrate (486.5 g) in acetone (6.8L) at 40° C. The reaction mixture was gently refluxed for 1 hr. The reaction mixture was cooled to 10° C. in an ice bath, filtered, washed with fresh acetone (3×500 mls), and dried under vacuum (60° C.) overnight to afford the tartrate salt as a white solid (466.4 g, mpt 191.7° C.). The di-p-tolyl-D-tartrate salt (466.4 g) was fully dissolved in methanol (10L) at gentle reflux. The resulting pale yellow solution was distilled at atmospheric pressure to approximately half its original volume. The resulting clear solution was allowed to cool to room temperature and stirred for 72 hrs, during which time a thick white precipitate formed. The precipitate was filtered, washed with fresh methanol (2×500 mls) and dried under vacuum (50° C.) overnight to yield a white solid (382.1 g, mpt 194.3° C.).

A solution of sodium hydroxide (2M, 31) and dichloromethane (31) were stirred together at room temperature. The di-p-tolyl-D-tartrate salt from above (371.4 g) was added in one go, and the mixture stirred for 1 hr. The phases were separated and the aqueous washed with fresh Dichloromethane (3×1L). The organic extracts were combined and evaporate in vacuo to afford the title compound (−)-(2R, 5S)-1-allyl-2,5-dimethylpiperazine as a mobile yellow oil (104.3 g,).

$R_f$: 0.25 (90/10/2; dichloromethane/methanol/ammonium hydroxide)

$[\alpha]_D$ −54.8° (c=1.19, ethanol)

The (+)-(1R,3S)-camphoric acid salt of (+)-(2S,5R)-1-allyl-2,5-dimethylpiperazine (577 g) from above was recrystallised from hot methanol (1225 ml). The crude, damp solid was further recrystallised from hot methanol (500 ml). The solid was collected by filtration and dried at 80° C. in vacuo to afford the compound as white crystals, 352 g $R_f$: 0.25 (90/10/2; dichloromethane/methanol/ammonium hydroxide)

$[\alpha]_D$ +48.3° (c=1.0, ethanol)

Optical purity determined to be >99% by HPLC analysis.

Preparation 2

(2S,5R)-1-allyl-4-benzyl-2,5-dimethylpiperazine

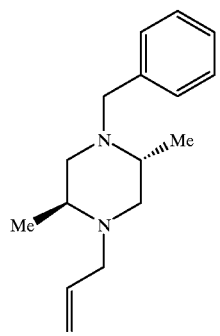

To a suspension of the (+)-(1R,3S)-camphoric acid salt of (+)-(2S,5R)-1-allyl-2,5-dimethylpiperazine from Preparation 1 (78.2 g) and benzaldehyde (26.5 g) in tetrahydrofuran (500 ml) containing glacial acetic acid (2 ml) was added sodium triacetoxyborohydride (93.3 g) portionwise over 10 minutes. The resulting mixture was stirred at room temperature for 4 hours. The reaction was partitioned between ethyl acetate (1500 ml) and aqueous sodium hydroxide (750 ml of 2N solution). The layers were separated and the organic phase was washed with 10% sodium metabisulphite solution (200 ml) and saturated brine solution. The organic layer was dried ($MgSO_4$) and evaporated to dryness in vacuo to give the title compound, 52.1 g.

m/z: 245 (MH+)

Rf: 0.63 (93/7/1 dichloromethane/methanol/ammonium hydroxide)

Preparation 3

(−)-(2R,5)-1-benzyl-2,5-dimethylpiperazine

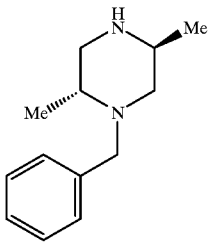

Tris(triphenylphosphine)rhodium(I) chloride (3 g) was added to a solution of the compound of Preparation 2 (52.1 g) in acetonitrile (400 ml) and water (80 ml). The reaction mixture was heated under a gentle reflux and the solvent allowed to distil off slowly. Additional acetonitrile/water (250 ml; 4:1 v/v) was added a such a rate as to maintain a steady distillation. After the addition of solvent was complete the distillation was continued until the volume was reduced to approximately 200 ml. The cooled solution was partitioned between ethyl acetate and 2N hydrochloric acid. The layers were separated and the organic phase extracted with further 0.5N hydrochloric acid. The combined aqueous extracts were basified with 2N sodium hydroxide solution and extracted into dichloromethane. The combined organic extracts were dried (MgSO$_4$) and evaporated to dryness in vacuo, to afford the title compound, 38.2 g.

m/z: 205 (MH$^+$)
Rf:0.27 (93/711 dichloromethane/methanol/ammonia)
[α]$_D$−113° (c 0.2, methanol)

Preparation 4

(2R,5S)-1-benzyl-4-[(R)-1-(4-bromophenyl)-1-(3-methoxyphenyl)methyl]-2,5-dimethylhexahydrolpyrazine

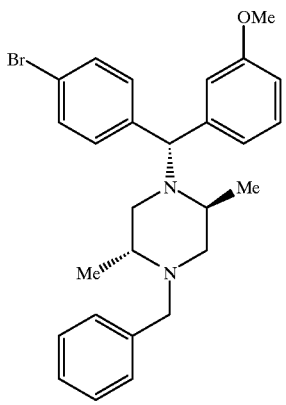

A solution of 4-bromobenzaldehyde (12 g), benzotriazole (7.73 g), and the compound of Preparation 3 (13.25 g) in toluene (200 ml) was heated under reflux with azeotropic removal of water for 3 hours. The solution was allowed to cool to room temperature, and then added dropwise to a cooled (−20° C.) solution of 3-methoxyphenylmagnesium bromide (prepared from 16.3 ml of the corresponding bromide and 3.15 g of magnesium turnings) in tetrahydrofuran (100 ml) and the reaction stirred at room temperature, under a nitrogen atmosphere for an hour. Saturated aqueous ammonium chloride solution was added, and the mixture stirred for 20 minutes. The mixture was diluted with ethyl acetate, the phases separated and the aqueous extracted with further ethyl acetate. The combined organic phases were dried (MgSO$_4$) and evaporated to dryness in vacuo. The residue was purified by column chromatography over silica gel, using gradient elution (10/90–20/80 ethyl acetate/hexane) to afford the title compound, 19.32 g.

R$_f$: 0.26 (10/90 ethyl acetate/hexane)

m/z: 479 (MH$^+$)

δ$_H$ (400 MHz, CDCl$_3$): 7.17–7.38 (10H, m), 6.76 (2H, m), 6.70 (1H, s), 5.00 (1H, s), 3.87 (1H, d), 3.74 (3H, s), 3.17 (1H, d), 2.49–2.61 (3H, m), 1.94 (2H, m), 1.05 (6H, 2xd).

Preparation 5

(2R,5S)-1-allyl-4-[(R)-1-(4-bromophenyl-1-(3-methoxyphenyl)methyl]-2,5-dimethylhexahydropyrazine

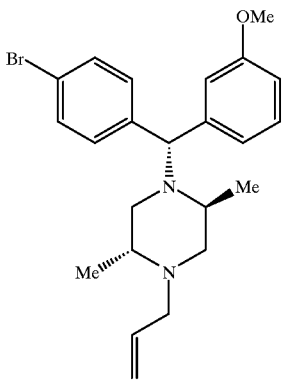

The compound of the above formula was prepared using a method similar to that used in Preparation 4 using (−)-(2R,5S)-1-allyl-2,5-dimethylpiperazine, 4-bromobenzaldehyde, benzotriazole and 3-methoxyphenyl magnesium bromide.

R$_f$: 0.30 (pentane/ethyl acetate, 1/1, v/v)

[α]$_D$+13.1 (c=0.13. methanol)

m/z: 429 (MH$^+$)

δ$_H$ (300 MHz, CDCl$_3$): 7.40 (2H, d), 7.33 (2H, d), 7.22 (1H, dd), 6.70–6.84 (3H, m), 5.85 (1H, m), 5.11–5.21 (3H, m), 3.78 (3H, s), 3.35 (1H, dd), 2.83 (2H, m), 2.60 (2H, m), 2.45 (1H, m), 2.11 (1H, m), 1.89 (1H, m), 1.16 (3H, d), 0.98 (3H, d).

Found: C, 64.01; H, 6.91; N, 6.86. C$_{23}$H$_{29}$BrN$_2$O requires C, 64.33; H, 6.81; N, 6.52%

The S isomer was also isolated.

Preparation 6

1-(1-ethoxymethyl)-1H-1,2,4-triazole

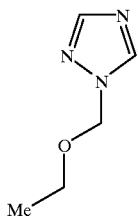

A solution of chloromethyl ethyl ether (23.5 g) in toluene (300 ml), was added dropwise, over an hour, to a solution of 1,2,4-triazole (50 g) in toluene (50 ml), and the reaction stirred at room temperature for 18 hours. On cooling, the reaction mixture was evaporated to dryness in vacuo, the residue triturated with dichloromethane, and the resulting suspension filtered. The filtrate was evaporated in vacuo and purified by column chromatography over silica gel (5/95 methanol/dichloromethane) to afford the title compound as a colorless oil, 23.9 g.

$R_f$: 0.26 (95/5 dichloromethane/methanol)

$\delta_D$ (300 MHz, CDCl$_3$): 8.28 (1H, s), 8.00 (1H, s), 5.54 (2H, s), 3.61 (2H, q), 1.22 (3H, t).

Preparation 7

(2R,5S)-1-allyl-4-[(R)-1-4-[1-(ethoxymethyl)-1H-1,2,4-triazol-5-yl]phenyl-1-(3-1-(3methoxyphenyl)methyl]-2,5-dimethylhexahydropyrazine

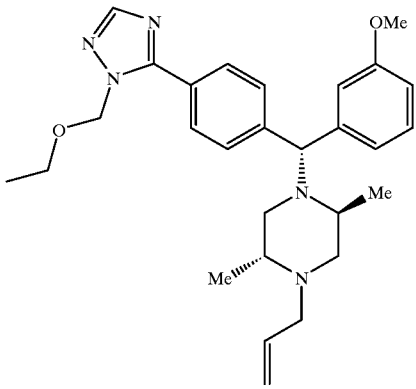

n-Butyl lithium (2.35 ml, 2,5M in pentanes) was added dropwise to a cooled (–70° C.) solution of the compound of Preparation 6 (860 mg) in tetrahydrofuran (20 ml) under a nitrogen atmosphere, and the mixture stirred for 10 minutes. Zinc chloride (6.77 ml, 1M in diethyl ether) was added and the reaction allowed to warm to room temperature. Tetrakis(triphenylphosphine)palladium(0) (260 mg) and a solution of the compound from Preparation 5 (1.94 g) in tetrahydrofuran (20 ml) were then added and the reaction stirred at 90° C., under a nitrogen atmosphere for 3 days. On cooling, methanol was added and the mixture evaporated to dryness in vacuo. The residue was purified by column chromatography over silica gel using gradient elution (95/5/0.25–90/10/0.5 toluene/isopropanol/ammonium hydroxide) to afford the title compound, as a yellow foam, 1.0 g.

$R_f$: 0.41 (90/10/0.75 hexane/isopropanol/ammonium hydroxide)

m/z: 476 (MH$^+$)

$[\alpha]_D$+21.7 (c=0.115, methanol)

$\delta_H$ (300 MHz, CDCl$_3$): 7.95 (1H, s), 7.84 (2H, d), 7.60 (2H, d), 7.24 (1H, dd), 6.80 (3H, m), 5.87 (1H, m), 5.52 (2H, s), 5.20 (3H, m), 3.77 (4H, m), 3.37 (1H, dd), 2.85 (1H, dd), 2.63 (2H, m), 2.51 (1H, m), 2.15 (1H dd), 1.92 (1H, dd), 1.26 (3H, t), 1.20 (3H, d), 1.00 (3H, d).

Found: C, 70.10; H, 7.59; N, 14.23. C$_{28}$H$_{37}$N$_5$O$_2$3/10 water requires C, 69.91; H, 7.88; N, 14.56%

Preparation 8

(2R,5S)-1-allyl-4-(R)-1-(3-methoxyphenyl)-1-[4-(1H-1,2,4-triazol--5-yl)phenyl]methyl-2,5-dimethylhexahydropyrazine

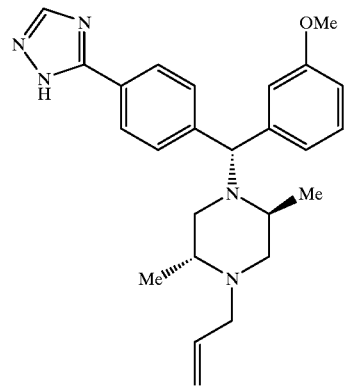

Hydrochloric acid (12 ml, 5N) was added to a solution of the compound from Preparation 7 (1.13 g) in methanol (30 ml), and the reaction stirred at room temperature for an hour, followed by 4 hours heating under reflux. The mixture was cooled in ice and basified with ammonium hydroxide and then evaporated to dryness in vacuo. The residue was partitioned between water (20 ml) and dichloromethane (150 ml), the phases separated and the aqueous extracted with further dichloromethane (2×150 ml). The combined organic extracts were dried (Na$_2$SO$_4$) and evaporated to dryness in vacuo. This material was purified by column chromatography over silica gel (85/15/1 pentane/isopropanol/ammonium hydroxide) to afford the title compound as a foam, 723 mg.

$R_f$: 0.31 (90/10 dichloromethane/methanol)

m/z: 418 (MH$^+$)

$\delta_H$ (300 MHz, CDCl$_3$): 8.16 (1H, s), 7.94 (2H, d), 7.55 (2H, d), 7.25 (1H, dd), 6.28 (2H, 2xd), 6.74 (1H, s), 5.88 (1H, m), 5.20 (3H, m), 3.78 (3H, s), 3.38 (1H, dd), 2.85 (2H, m), 2.64 (2H, m), 2.52 (1H, m), 2.18 (1H, dd), 1.93 (1H, dd), 1.20 (3H, d), 1.11 (3H, d).

Found: C, 71.57; H, 7.36; N, 15.78. C$_{25}$H$_{31}$N$_5$O 3/10CH$_3$CH(OH)CH$_3$ requires C, 71.42; H, 7.73; N, 16.08%

Preparation 9

(2R,5S)-1-benzyl-4-[(R)-1-4-[1-(2-ethoxyethyl)-1H-1,2,4-triazol-5-yl]phenyl-1-(3-methoxyphenyl)methyl]-2,5-dimethylhexahydropyrazine

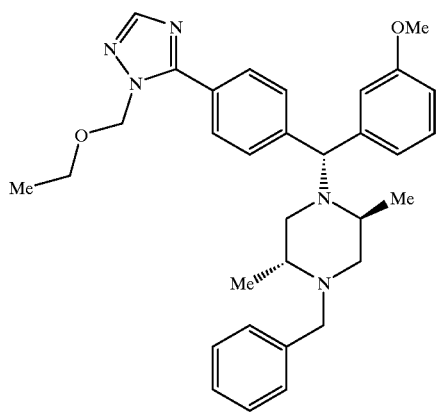

n-Butyl lithium (32.7 ml, 1.6M in hexane) was added dropwise to a cooled (−70° C.) solution of of the compound of Preparation 6 (7.67 g) in tetrahydrofuran (150 ml) under a nitrogen atmosphere, so as to maintain the temperature below −65° C., and the mixture stirred for 10 minutes. Zinc chloride (60.4 ml, 1M in diethyl ether) was added dropwise and the reaction allowed to warm to room temperature. Tetrakis(triphenylphosphine)palladium(0) (3.49 g) and a solution of the compound from Preparation 4 (19.3 g) in tetrahydrofuran (150 ml) were then added and the reaction stirred at 90° C., under a nitrogen atmosphere for 3 days. On cooling, methanol was added and the mixture evaporated to dryness in vacuo. The residue was purified by column chromatography over silica gel using gradient elution (90/10/0.75–80/20/2 hexane/isopropanol/ammonium hydroxide) to afford the title compound, as a yellow foam, 1.51 g, and recovered starting material.

$R_f$: 0.42 (hexane/isopropanol/ammonium hydroxide)

m/z: 526 (MH$^+$)

$\delta_H$ (400 MHz, CDCl$_3$): 7.91 (1H, s), 7.80 (2H, d), 7.58 (2H, d), 7.10–7.30 (6H, m), 6.72–6.80 (3H, m), 5.48 (2H, s), 5.12 (1H, s), 3.87 (1H, d), 3.74 (5H, m), 3.18 (1H, d), 2.53 (4H, m), 2.00 (2H, m), 1.20 (6H, 2xd), 1.08 (3H, t).

Preparation 10

(2R,5S)-1-benzyl-4-(R)-1-(3-methoxyphenyl)-1-[4-(1H-1,2,4-triazol-5-yl)phenyl]methyl-2,5-dimethylhexahydropyrazine

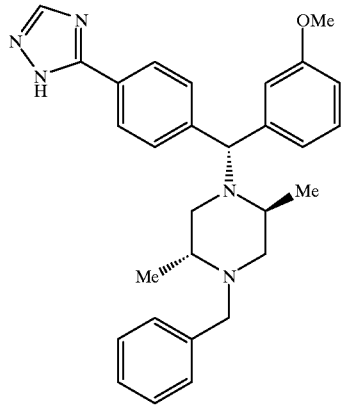

The compound of the above formula was prepared using the compound of Preparation 7 following a similar procedure to that described in Preparation 8, and was obtained in 37% yield.

m/z: 468 (MH$^+$)

$\delta_H$ (400 MHz, CDCl$_3$): 8.06 (1H, s), 7.90 (2H, d), 7.70 (2H, d), 7.16–7.28 (6H, m), 6.78 (3H, m), 5.09 (1H, s), 3.88 (1H, d), 3.74 (3H, s), 3.19 (1H, d), 2.54–2.72 (4H, m), 2.00 (2H, m), 1.07 (6H, 2xd).

Preparation 11

(2R,5S)-1-allyl-4-[(R)-1-(4-bromophenyl)-1-(3-[1-(tert-butyl)-1,1-dimethylsilyl]oxyphenyl)methyl]-2,5-dimethylhexahydropyrazine

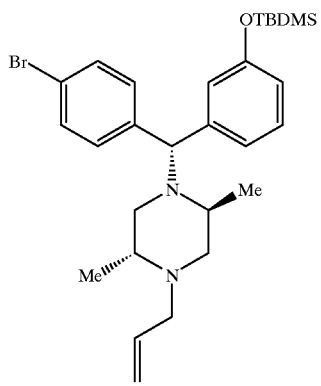

A solution of 4-bromobenzaldehyde (12.88 g), benzotriazole (8.29 g), (−)-(2R,5S)-1-allyl-2,5-dimethylpiperazine (10.74 g) in toluene (350 ml) was heated under reflux with azeotropic removal of water for 8 hours. The solution was allowed to cool to room temperature, and then added dropwise to a cooled (−20° C.) solution of 3-tertbutyldimethylsilyloxyphenylmagnesium bromide (prepared from 40 g of the corresponding bromide and 24.3 g of magnesium turnings) in tetrahydrofuran (250 ml) and the reaction stirred at room temperature under a nitrogen atmosphere for an hour. Saturated aqueous ammonium chloride solution was added, and the mixture stirred for 20 minutes. The mixture was diluted with ethyl acetate, the phases separated and the aqueous layer extracted with further ethyl acetate. The combined organic phases were dried (MgSO$_4$), and evaporated to dryness in vacuo. The residue was purified by column chromatography over silica gel using gradient elution (98/2–90/10 dichloromethane/methanol) to afford the title compound, 26.1 g.

R$_f$ : 0.33 (5/95 methanol/dichloromethane)

m/z: 528 (M$^+$)

Preparation 12

(2S,5R)-1-[(R)-1-(4-bromophenyl)-1-(3-[1-(tert-butyl)-1,1-dimethylsilyl]oxyphenyl)methyl]-2,5-dimethylhexahydropyrazine

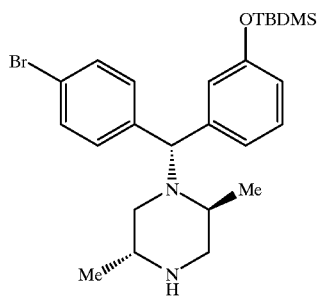

Tris(triphenylphosphine)rhodium(I) chloride (3.05 g) was added to a solution of the compound of Preparation 11 (17.44 g) in acetonitrile (400 ml) and water (100 ml), and the reaction stirred under reflux, while allowing the solvent to distill off, for 2 hours. Additional acetonitrile/water (4/1 by volume) was added at such a rate as to maintain a steady reflux. On cooling, the reaction mixture was diluted with brine and extracted with dichloromethane. The combined organic extracts were dried (Na$_2$SO$_4$) and evaporated to dryness in vacuo. The residue was purified by column chromatography over silica gel using gradient elution (95/5–90/10 dichlorormethane/methanol) to afford the title compound, 10.53 g.

R$_f$: 0.34 (90/10 dichloromethane/methanol)

m/z: 489 (MH$^+$)

δ$_H$ (300 MHz, CDCl$_3$): 7.37 (2H, d), 7.28 (2H, d), 7.17 (1H, dd), 6.73 (2H, m), 6.54 (1H, s), 5.16 (1H, s), 2.92 (2H, m), 2.58–2.72 (2H, m), 2.40 (1H, m), 1.65 (1H, dd), 1.14 (3H, d), 0.98 (3H, d), 0.92 (9H, s), 0.12 (6H, s).

Preparation 13

(2R,5S)-1-benzyl-4-[(R)-1-(4-bromophenyl)-1-(3-[1-(tert-butyl)-1,1-dimethylsilyl]oxyphenyl)methyl]-2,5-dimethylhexahydropyrazine

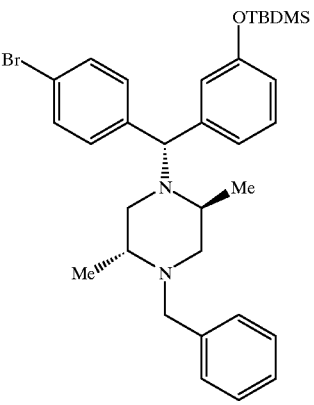

A solution of the compound from Preparation 12 (10.53 g), benzaldehyde (2.84 ml), acetic acid (1.35 ml) and sodium triacetoxyborohydride (9.12 g) in tetrahydrofuran (75 ml) was stirred at room temperature for 18 hours. The reaction mixture was then partitioned between ethyl acetate (25 ml) and aqueous ammonium chloride solution, and the phases separated. The aqueous layer was extracted with further ethyl acetate, the combined organic extracts dried (MgSO$_4$) and evaporated to dryness in vacuo. The residue was purified by column chromatography over silica gel using gradient elution (100/0–95/5 dichloromethane/methanol) to afford the title compound, 10.4 g.

R$_f$ : 0.30 (99/1 dichloromethane/methanol)

m/z: 580 (MH$^+$)

δ$_H$ (400 MHz, CDCl$_3$): 7.40 (2H, d), 7.33 (2H, d), 7.29 (4H, m), 7.22 (1H, m), 7.17 (1H, dd), 6.77 (2H, m), 6.66 (1H, s), 5.00 (1H, s), 3.90 (1H, d), 3.20 (1H, d), 2.70 (1H, d), 2.58 (3H, m), 2.00 (2H, m), 1.08 (6H, 2xd), 0.97 (9H, s), 0.18 (6H, s).

Preparation 14

(2R,5S)-1-benzyl-4-((R)-1-(3-[1-(tert-butyl)-1,1-dimethylsilyl]oxyphenyl)-1-4-[2-(1,1,1-trimethylsilyl)eth-1-ynyl]phenylmethyl)-2,5-dimethylhexahydropyrazine

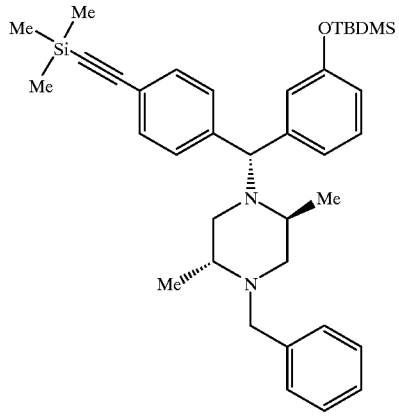

A suspension of the compound from Preparation 13 (4.0 g), (trimethylsilyl)acetylene (1.17 ml), copper(I)iodide (19 mg) and bis(triphenylphosphine)palladium(II) chloride (140 mg) in diethylamine (50 ml) was stirred at 150° C. for 9 hours. On cooling, the reaction mixture was partitioned between aqueous ammonium chloride solution, and ethyl acetate. The phases were separated and the aqueous layer extracted with further ethyl acetate, the combined organic extracts dried (MgSO$_4$) and evaporated in vacuo. The residue was purified by column chromatography over silica gel using gradient elution (100/0–90/10 pentane/ethyl acetate) to afford the title compound as a brown oil, 2.24 g.

m/z: 597 (MH$^+$)

$\delta_H$ (400 MHz, CDCl$_3$): 7.36 (4H, m), 7.23 (4H, m). 7.19 (1H, m), 7.14 (1H, dd), 6.77 (1H, d), 6.72 (1H, d), 6.62 (1H, s), 5.02 (1H, s), 3.88 (1H, d), 3.18 (1H, d), 2.68 (1H, d), 2,54 (3H, m), 1.96 (2H, m), 1.05 (6H, 2xd), 0.92 (9H, s), 0.22 (6H, s), 0.14 (6H, s).

Preparation 15
(2R,5S)-1-benzyl-4-[(R)-1-(3-[1-(tert-butyl)-1,1-dimethylsilyl]oxyphenyl)-1-(4-eth-1-ynylpenyl)methyl]-2,5-dimethylhexahydropyrazine

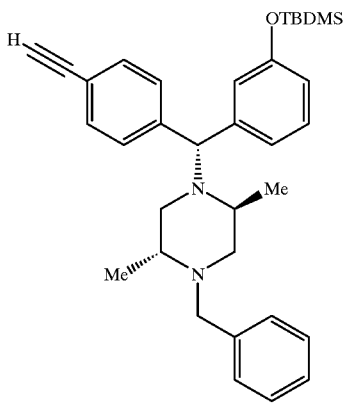

Aqueous sodium hydroxide solution (8 ml, 1N) was added to a solution of the compound from Preparation 14 (2.24 g) in methanol (10 ml) and tetrahydrofuran (10 ml) and the reaction stirred at room temperaturee for 18 hours. The mixture was concentrated in vacuo and the residue partitioned between water and ethyl acetate. The phases were separated and the aqueous layer extracted with ethyl acetate. The combined organic extracts were dried (MgSO$_4$) and evaporated in vacuo. This material was purified by column chromatography over silica gel using gradient elution (95/5–60/40 pentane/ethyl acetate) to afford the title compound as a brown oil, 0.96 g.

m/z: 525 (MH$^+$)

$\delta_H$ (400 MHz, CDCl$_3$): 7.39 (4H, m), 7.12–7.30 (6H, m), 6.78 (1H, d), 6.72 (1H, d), 6.62 (1H, s), 5.04 (1H, s), 3.88 (1H, d), 3.18 (1H, d), 2.68 (1H, d), 2.55 (3H, m),1.98 (2H, m), 1.30 (1H, m), 1.06 (6H, 2xd), 0.93 (9H, s), 0.14 (6H, s).

Preparation 16
(2R,5S)-1-benzyl-4-(R)-1-(3-[1-(tert-butyl)-1,1-dimethylsilyl]oxyphenyl)-1-[4-(1H-1,2,3-triazol-4-yl)phenyl]methyl-2,5-dimethylhexahydropyrazine

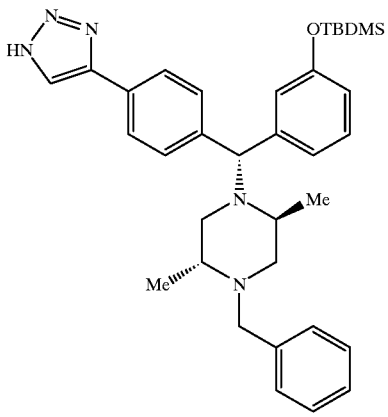

A solution of the compound from Preparation 15 (688 mg) in trimethylsilyl azide (5 ml) was heated in a sealed vessel to 170° C. for 18 hours. On cooling, the mixture was partitioned between aqueous ammonium chloride solution and ethyl acetate, and the phases separated. The aqueous layer was extracted with ethyl acetate, and the combined organic extracts dried (MgSO$_4$) and evaporated in vacuo. The residue was purified by column chromatography over silica gel using gradient elution (95/5–75/25 pentane/ethyl acetate) to afford the title compound, as a brown oil, 433 mg.

$R_f$: 0.38 (75/25 pentane/ethyl acetate)

m/z: 568 (MH$^+$)

$\delta_H$ (400 MHz, CDCl$_3$): 7.90 (1H, s), 7.70 (2H, d), 7.50 (2H, d), 7.18–7.28 (5H, m), 7.15 (1H, dd), 6.80 (1H, d), 6.73 (1H, d), 6.68 (1H, s), 5.08 (1H, s), 3.89 (1H, d), 3.20 (1H, d), 2.55–2.72 (4H, m), 2.00 (2H, m), 1.08 (6H, 2xd), 0.92 (9H, s), 0.14 (6H, s).

Preparation 17

[2-(4-{4-[(R)-1-[(2S,5R)-4-benzyl-2,5-dimethylhexahydropyrazin-1-yl]-1-(3-hydroxyphenyl)methyl]phenyl}-1H-1,2,3-triazol-1-yl)ethoxy]methyl cyanide and

[2-(4-{4-[(R)-1-[(2S,5R)-4-benzyl-2,5-dimethylhexahydropyrazin-1-yl]-1-(3-hydroxyphenyl)methyl]phenyl}-2H-1,2,3-triazol-2-yl)ethoxy]methyl cyanide

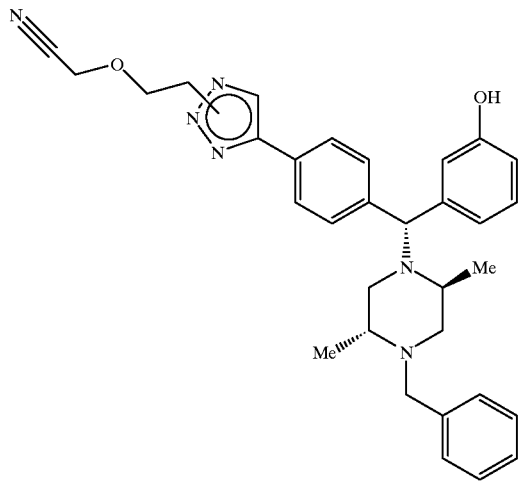

A solution of the compound of Preparation 16 (3.50 g), 5-bromo-3-oxopentanenitrile (0.968 g) and potassium carbonate (2.55 g) in acetonitrile (90 ml) was heated under reflux for 18 hrs. The reaction mixture was quenched with ammonium chloride solution and the product extracted with ethyl acetate (×3). The combined organic layers were dried over MgSO$_4$ and evaporated under reduced pressure. The crude product was purified on silica gel using a gradient elution (ethyl acetate/hexane, 2.5/7.5–1/1, v/v) to afford the N2 iosmer, 1.904 g.

m/z: 538 (MH$^+$)

$R_f$ 0.2 (ethyl acetate/hexane, 25/75)

$\delta_H$ (400 MHz, CDCl$_3$) 7.80 (1H, s), 7.70 (2H, d), 7.50 (2H, d), 7.30–7.10 (6H, m), 6.80 (1H, d), 6.70 (2H, m), 5.06 (1H, s), 4.65 (2H, m), 4.25 (2H, s), 4.15 (2H, m), 3.90 (1H, d), 3.22 (1H, d), 2.80–2.50 (4H, m), 2.05 (2H, m), 1.10 (6H, m).

followed by the N1 isomer, 717 mg.

m/z: 538 (MH$^+$)

$R_f$ 0.1 (ethyl acetate/hexane, 25/75)

$\delta_H$ (400 MHz, CDCl$_3$): 7.80 (1H, s), 7.75 (2H, d), 7.50 (2H, d), 7.35–7.15 (6H, m), 6.80

(1H, d), 6.70 (2H, m), 5.05 (1H, s), 4.60 (2H, m), 4.25 (2H, s), 4.05 (2H, m), 3.90 (1H, d), 3.25 (1H, d), 2.75–2.55 (4H, m), 2.05 (2H, m), 1.10 (6H, m).

Preparation 18

4-cyano-[(R)-a-(2(S),5(R)-4-allyl-2,5-dimethyl-1-piperazinyl)-3-tert-butyldimethylsilyloxybenzyl]benzene.

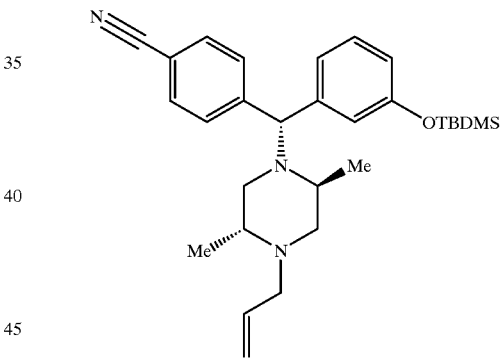

A solution of (−)-(2R,5S)-1-allyl-2,5-dimethylpiperazine (21.6 g), benzotriazole (16.68 g) and 4-cyanobenzaldehyde (18.35 g) in toluene (800 ml) was heated under reflux with azeotropic removal of water for 3 hours. The solution was cooled to ambient temperature and added to a cold solution (−10° C.) of 3-tert-butyldimethylsilyloxyphenylmagnesium bromide (prepared from 79 g of the corresponding bromide and 6.8 g of magnesium turnings) in tetrahydrofuran (500 ml) at such a rate as to maintain the internal temperature in the range −10 to 0° C. The resulting solution was stirred at 0° C. for 15 minutes, ambient temperature for 30 minutes and then quenched with saturated aqueous ammonium chloride solution. The layers were separated and the aqueous solution extracted with diethyl ether (2×200 ml). The combined organic extracts were dried (Na$_2$SO$_4$) and evaporated to dryness in vacuo. The residue was purified by column chromatography over silica gel using gradient elution (5–20% ethyl acetate/dichloromethane) to afford the title compound, 4-[(R)-a-(2(S),5(R)-4-ally-2,5-dimethyl-1-piperazinyl)-3-tert-butyldimethylsilyloxybenzyl]cyanobenzene, 32.9 g.

m/z: 476 (MH⁺)

$R_f$: 0.35 (90/10/2; hexane/ethyl acetate/diethylamine)

Found: C, 72.26; H, 8.78; N, 8.09. $C_{29}H_{41}N_3OSi.3/10$ ethyl acetate requires C, 72.23; H, 8.71; N, 8.37%

$[\alpha]_D$+22.9° (c=0.112, methanol)

Preparation 19

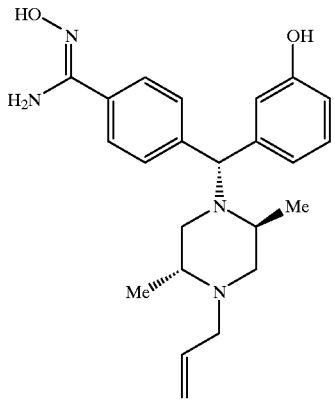

A solution of sodium bicarbonate (35 g), and hydroxylamine hydrochloride (10.97 g) in water (75 ml) was added dropwise to a solution of the compound from Preparation 18 (10 g) in methanol (150 ml) and the reaction stirred at reflux for 18 hours. On cooling, the reaction mixture was extracted with dichloromethane (2×200 ml), the combined organic extracts dried ($Na_2SO_4$) and evaporated to dryness in vacuo. The residue was purified by column chromatography over silica gel using gradient elution (97/3/0.5–97/3/1 dichloromethane/methanol/ammonium hydroxide) to afford the title compound, 5.3 g.

$R_f$: 0.39 (90/10/2 dichloromethane/methanol/ammonium hydroxide)

m/z: 395 (MH⁺)

$[\alpha]_D$+24.00 (c=0.110, methanol)

$\delta_H$ (300 MHz, $CDCl_3$): 7.54 (2H, d), 7.46 (2H, d), 7.16 (1H, dd), 6.69 (2H, 2xd), 6.59 (1H, s), 5.88 (1H, m), 5.16 (3H, m), 4.83 (2H, s), 3.38 (1H, dd), 2.87 (2H, m), 2.46–2.68 (3H, m), 2.14 (1H, dd), 1.94 (1H, dd), 1.16 (3H, d), 1.00 (3H, d).

Preparation 20

[(R)-1-(2S,5R)-2,5-dimethyl-4-benzyl-1-piperazinyl-1-(3-(tert-butyldimethylsilyl)oxyphenyl)methyl]benzonitrile.

and

[(S)-1-(2S,5R)-2,5-dimethyl-4-benzyl-1-piperazinyl-1-(3-(tert-butyldimethylsilyl)oxyphenyl)methyl]benzonitrile.

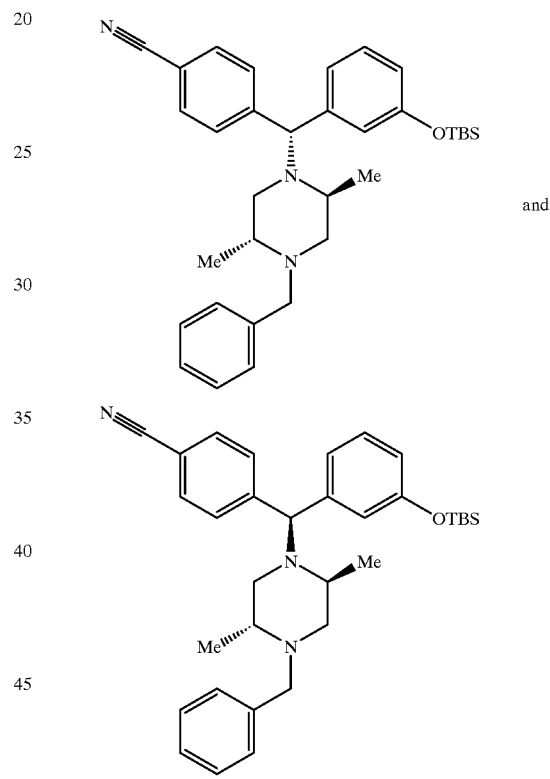

and

A solution of the compound of Preparation 3 (10.2 g), benzotriazole (5.95 g) and 4-cyanobenzaldehyde (6.55 g) in toluene (150 ml) was heated under reflux with azeotropic removal of water for 3 hours. The solution was cooled to ambient temperature and added to a cold solution (−25° C.) of 3-tert-butyldimethylsilyloxyphenylmagnesium bromide (prepared from 28.7 g of the corresponding bromide and 2,4 g of magnesium turnings) in tetrahydrofuran (100 ml) at such a rate as to maintain the internal temperature at −25° C. The resulting solution was stirred at 0° C. for 15 mins, ambient temperature for 30 min and then quenched with 2N sodium hydroxide solution. The layers were separated and the aqueous solution extracted with ethyl acetate (2×). The combined organic extracts were washed with water, and brine. The organic extracts were dried ($Na_2SO_4$) and evaporated to dryness in vacuo. The residue was purified by column chromatography over silica gel using gradient elution (100% dichloromethane to 10% ethyl acetate/dichloromethane) to afford the title compounds. The aR-diastereomer was the first to elute, 17.38 g.

m/z: 526 ($MH^+$)

$R_f$ : 0.62 (3/1 hexane/ethyl acetate)

The aS-diastereomer was also isolated and eluted second, 2.61 g.

m/z: 526 ($MH^+$)

$R_f$ : 0.53 (3/1 hexane/ethyl acetate)

Preparation 21

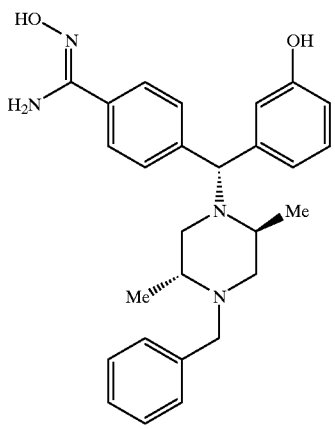

The title compound was prepared using the compound from Preparation 20, using a similar method to that described in Preparation 19.

m/z: 445 ($MH^+$)

$\delta_H$ (300 MHz, $CDCl_3$): 7.48 (4H, m), 7.24 (5H, m), 7.12 (1H, m), 6.54–6.72 (3H, m), 5.05 (1H, m), 4.87 (1H, br s), 3.94 (1H, d), 3.20 (1H, d), 2.52–2.74 (4H, m), 2.02 (2H, m), 1.10 (3H, d), 1.02 (3H, d).

Preparation 22

Ethyl 2-(4-formylphenyl)-1,3-thiazole-4-carboxylate

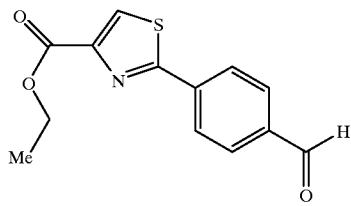

2-(4-thiobenzamido)-1,3-dioxalane (4.5 g) was added to a solution of ethyl-3-bromopyruvate (4.2 g) in dimethylformamide (70 ml) and the reaction stirred at room temperature for 18 hours and a further 3 hours at 80° C. On cooling, the mixture was partitioned between water and dichloromethane, and the phases separated. The aqueous phase was extracted with dichloromethane, the combined organic extracts dried ($Na_2SO_4$), and evaporated to dryness in vacuo, to give a brown solid. Hydrochloric acid (40 ml of 2N solution) was added to a solution of this material in dichloromethane (40 ml) and the reaction stirred at room temperature for 18 hours. The phases were separated, and the aqueous layer extracted with dichloromethane (2×50 ml). The combined organic extracts were dried ($Na_2SO_4$) and evaporated to dryness in vacuo. The residue was purified by column chromatography over silica gel (97/3 dichloromethane/diethyl ether) to afford the title compound, 5.01 g.

$R_f$ : 0.51 (98/2 dichloromethane/methanol)

m/z: 262 ($MH^+$)

$\delta_H$ (400 MHz, $CDCl_3$): 10.10 (1H, s), 8.28 (1H, s), 8.20 (2H, d), 7.98 (2H, d), 4.48 (2H, q), 1.45 (3H, t).

Preparation 23

Ethyl 2-(4-formylphenyl)-1,3-thiazole-4-acetate

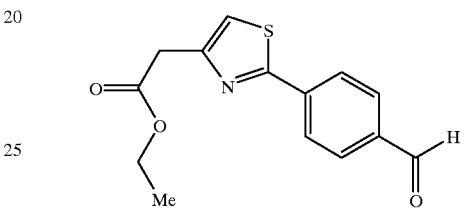

The title compound was prepared from 2-(4-thiobenzamido)-1,3-dioxalane and ethyl 4-bromoacetoacetate following a similar method to that described in Preparation 22, and was obtained in 82% yield.

$R_f$ : 0.55 (50/50 hexane/ethyl acetate)

m/z: 276 ($MH^+$)

$\delta_H$ (300 MHz, $CDCl_3$): 10.05 (1H, s), 8.13 (2H, d), 7.95 (2H, d), 7.32 (1H, s), 4.24 (2H, q), 3.96 (2H, s), 1.30 (3H, t).

Preparation 24

(+)-Ethyl 2-{4-[(R)-1-[(2S,5 R)-4-allyl-2,5-dimethylhexahydropyrazin-1-yl]-1-(3-[1-(tert-butyl)-1,1-dimethylsilyl]oxyphenyl)methyl]phenyl}-1,3-thiazole-4-carboxylate

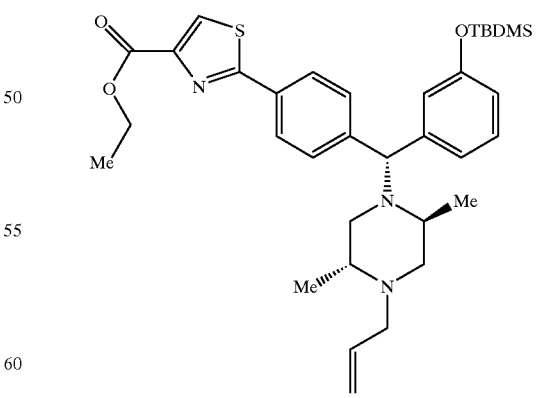

The compound of the above formula was prepared by a similar method to that described for Preparation 4, using the compound of Preparation 22 (10 g), benzotriazole (4.6 g), and (−)-(2R,5S)-1-allyl-2,5-dimethylpiperazine (5.9 g) and 3-tert-butyldimethylsilyloxyphenyl-magnesium bromide to afford the title compound as a yellow foam, 3.89 g.

$R_f$: 0.14 (98/2 dichloromethane/methanol)

m/z: 606 (MH$^+$)

$[\alpha]_D$+11.37 (c=0.127 methanol)

$\delta_H$ (400 MHz, CDCl$_3$): 8.13 (1H, s), 7.93 (2H, d), 7.54 (2H, d), 7.19 (1H, dd), 6.81 (1H, d), 6.76 (1H, d), 6.64 (1H, s), 5.88 (1H, m), 5.18 (3H, m), 4.44 (2H, q), 3.37 (1H, m), 2.84 (1H, m), 2.92 (2H, m), 2.50 (1H, m), 2.16 (1H, m), 1.92 (1H, m), 1.44 (3H, t), 1.10 (3H, d), 0.98 (12H, m), 0.17 (6H, s).

Preparation 25

Ethyl 2-(2-{4[(R)-1-[(2S,5R)-4-allyl-2,5-dimethylhexahydropyrazin-1-yl]-1-(3-[1-(tert-butyl)-1,1-dimethylsily]oxyphenylmethyl]phenyl}-1,3-thiazole-4-yl)acetate

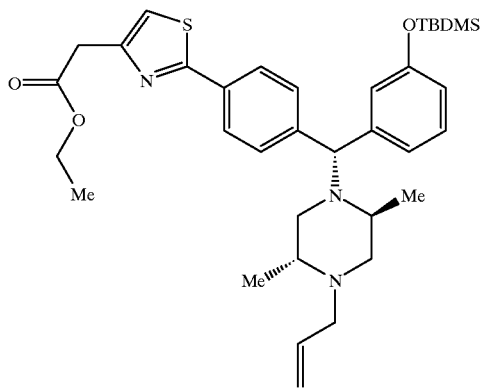

The compound of the above formula was prepared using the compound from Preparation 23, (−)-(2R,5S)-1-allyl-2,5-dimethylpiperazine, benzotriazole and 3-tert-butyldimethylsilyloxy-phenylmagnesium bromide following a similar procedure to that described in Preparation 4, and was obtained in 54% yield.

$R_f$: 0.33 (95/5 dichloromethane/methanol)

m/z: 620 (MH$^+$)

$\delta_H$ (400 MHz, CDCl$_3$): 7.85 (2H, d), 7.52 (2H, d), 7.28 (2H, m), 6.81 (1H, d), 6.76 (1H, d), 6.66 (1H, s), 5.88 (1H, m), 5.17 (3H, m), 4.22 (2H, q), 3.90 (2H, s), 3.36 (1H, dd), 2.85 (2H, m), 2.61 (2H, m), 2.50 (1H, m), 2.15 (1H, m), 1.92 (1H, m), 1.30 (3H, t), 1.19 (3H, d), 0.98 (12H, m), 0.18 (6H, s).

Preparation 26

(+)-3-((R)-1-[(2S,5R)-4-allyl-2,5-dimethylhexahydropyrazin-1-yl]-1-4-[4-(hydroxymethyl)-1,3-thiazol-2-yl]phenylmethyl) phenyl [1-(tert-butyl)-1,1-dimethylsilyl]ether

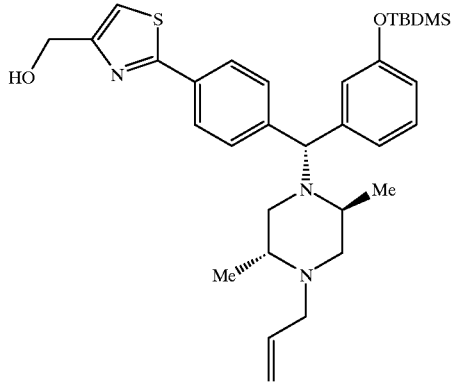

The above shown compound was prepared by reduction of the compound of Preparation 24 by use of LiAlH in THF.

The results were:

m/z: 564 (MH$^+$)

$[\alpha]_D$+8.84 (c=0.120 methanol)

$\delta_H$ (300 MHz, CDCl$_3$): 7.87 (2H, d), 7.51 (2H, d), 7.18 (2H, m), 6.78 (2H, 2xd), 6.63 (1H, s), 5.89 (1H, m), 5.18 (3H, m), 4.80 (2H, d), 3.37 (1H, m), 2.85 (2H, m), 2.60 (2H, m), 2.50 (1H, m), 2.30 (1H, t), 2.17 (1H, m), 1.93 (1H, m), 1.18 (3H, d), 0.96 (12H, m), 0.16 (6H, s).

Preparation 27

3-((R)-1-[(2S,5R)-4-allyl-2,5-dimethylhexahydropyrazin-1-yl]-1-4-[4-(hydroxyethyl)-1,3-thiazol-2-yl]phenylmethyl) phenyl [1-(tert-butyl)-1,1-dimethylsilyl]ether

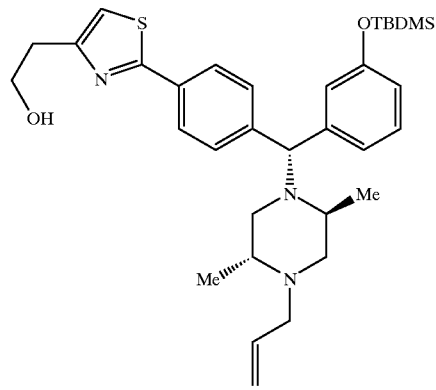

The compound of the above formula was prepared by a similar method to that described for Preparation 26, using the compound of Preparation 25 m/z: 578 (MH$^+$)

$\delta_D$ (400 MHz, CDCl$_3$): 7.85 (2H, d), 7.53 (2H, d), 7.18 (1H, dd), 6.95 (1H, s), 6.80 (1H, d), 6.76 (1H, d), 6.66 (1H, s), 5.88 (1H, m), 5.17 (3H, m), 4.00 (2H, q), 3.48 (1H, m), 3.36 (1H, dd), 3.04 (2H, m), 2.87 (2H, m), 2.62 (2H, m), 2.50 (1H, m), 2.17 (1H, m), 1.93 (1H, m), 1.20 (3H, d), 0.98 (3H, d).

Preparation 28

(+)-2-{4-[(R)-1-[(2S,5R)-4-allyl-2,5-dimethylhexahydropyrazin-1-yl]-1-(3-[1-(tert-butyl)-1,1-dimethylsilyl]oxyphenyl)methyl]phenyl}-1,3-thiazole-4-carboxaldehyde

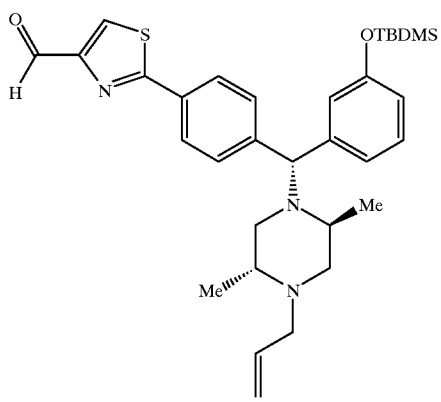

Manganese dioxide (6.8 g) was added to a solution of the compound from Preparation 26 (1.8 g) in dichloromethane (50 ml) and the reaction stirred at room temperature for 5 days. The reaction mixture was filtered through a pad of Arbocel, and washed well with further dichloromethane (200 ml). The filtrated was then evaporated to dryness in vacuo. The residue was purified by column chromatography over silica gel (30/70 ethyl acetate/hexane) to afford the title compound, 960 mg.

$R_f$: 0.41 (50/50 ethyl acetate/hexane)

m/z: 562 (MH$^+$)

$[\alpha]_D$+9.35 (c=0.113 methanol)

$\delta_H$ (400 MHz, CDCl$_3$): 10.10 (1H, s), 8.15 (1H, s), 7.90 (2H, d), 7.56 (2H, d), 7.19 (1H, dd), 6.78 (2H, m), 6.64 (1H, s), 5.86 (1H, m), 5.18 (3H, m), 3.37 (1H, m), 2.83 (2H, m), 2.60 (3H, m), 2.18 (1H, m), 1.93 (1H, m), 1.20 (3H, d), 1.97 (12H, m), 0.15 (6H, s).

Found: C, 68.10, H, 7.76; N, 7.40. C$_{32}$H$_{43}$N$_3$O$_2$SSi requires C, 68.41; H, 7.71; N, 7.48

Preparation 29

(+)-Ethyl 2-[2-(2-{4-[(R)-1-[(2S,5R)-4-allyl-2,5-dimethylhexahydropyrazin-1-(3-[1-(tert-butyl)-1,1-dimethylsilyl]oxyphenyl)methyl]phenyl}-1,3-thiazol-4-yl)ethyl]aminoacetate

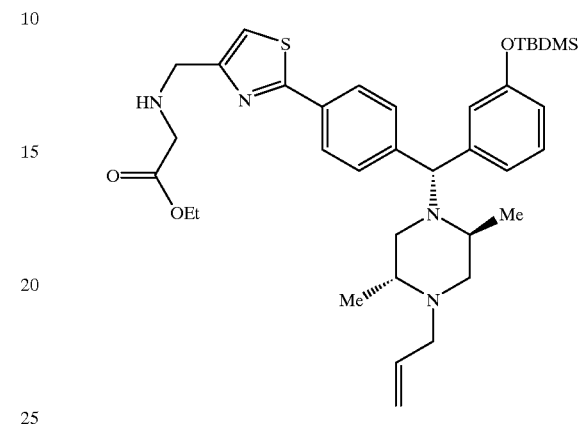

Sodium triacetoxyborohydride (498 mg) was added to a solution of the compound from Preparation 28 (660 mg) and glycine ethyl ester hydrochloride (197 mg) in acetonitrile (40 ml) and the reaction stirred at room temperature for 18 hours. The mixture was partitioned between ethyl acetate and saturated aqueous sodium bicarbonate solution, and the phases separated. The aqueous phase was extracted with ethyl acetate, the combined organic extracts dried (Na$_2$SO$_4$), and evaporated to dryness in vacuo. The residue was purified by column chromatography over silica gel (70/30/2 hexane/ethyl acetate/diethylamine) to afford the title compound as a viscous gum, 478 mg.

$R_f$: 0.18 (70/30/2 hexane/ethyl acetate/diethylamine)

m/z: 649 (MH$^+$)

$[\alpha]_D$+15.61 (c=0.083 methanol)

$\delta_H$ (400 MHz, CDCl$_3$): 7.87 (2H, d), 7.52 (2H, d), 7.20 (1H, dd), 7.10 (1H, s), 6.82 (1H, d), 6.76 (1H, d), 6.65 (1H, s), 5.88 (1H, m), 5.18 (3H, m), 4.20 (2H, q), 4.00 (2H, s), 3.52 (2H, s), 3.38 (1H, m), 2.89 (2H, m), 2.64 (2H, m), 2.52 (1H, m), 2.18 (1H, m), 1.94 (1H, m), 1.30 (3H, t), 1.10 (3H, d), 0.98 (12H, m), 0.18 (6H, s).

Found: C, 66.14; H, 8.11; N, 8.57. C$_{36}$H$_{52}$N$_4$O$_3$SSi requires C, 66.63; H, 8.08; N, 8.63%

Preparation 30

(+)-Ethyl 2-[[2-(2-{4-[(R)-1-[(2S,5R)-4-allyl-2,5-dimetylhexahydropyrazin-1-yl-1-(3-[1-(tert-butyl)-1,1-dimethylsilyl]oxyphenyl)methyl]phenyl}-1,3-thiazol-4-yl)ethyl](methyl)amino]acetate

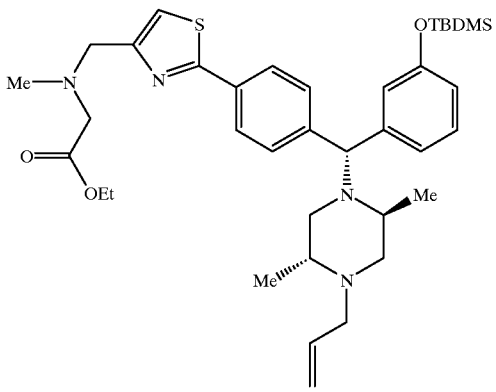

The title compound was prepared from sarcosine ethyl ester hydrochloride and the compound of Preparation 28 following a similar procedure to that described in preparation 29 and was obtained as a viscous gum, in 92% yield.

$R_f$: 0.27 (95/5 dichloromethane/methanol)

$[\alpha]_D$ +7.0° (c=0.13, methanol)

$\delta_H$ (400 MHz, CDCl$_3$): 7.87 (2H, d), 7.52 (2H, d), 7.19 (2H, m), 6.82 (1H, d), 6.76 (1H, d), 6.66 (1H, s), 5.89 (1H, m), 5.20 (3H, m), 4.20 (2H, q), 3.96 (2H, s), 3.39 (3H, m), 2.86 (1H, m), 2.62 (2H, m), 2.50 (3H, s), 2.18 (1H, m), 1.94 (1H, m), 1.30 (3H, t), 1.20 (3H, d), 1.10 (12H, m), 0.18 (6H, s).

Preparation 31

Ethyl 2-4-[(R)-1-[(2S,5S)-2,5-dimethylhexahydropyrazin-1-yl]-1-(3-hydroxyphenyl)methyl]phenyl-1,3-thiazole-4-carboxylate

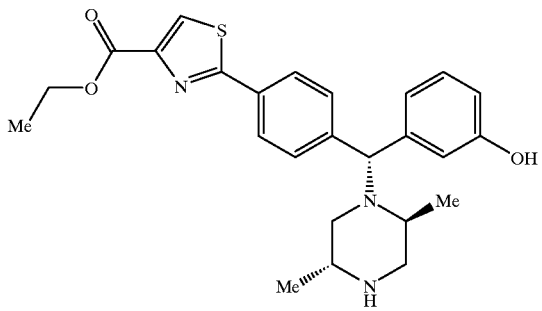

Tris(triphenylphosphine)rhodium(I) chloride (1.04 g) was added to a solution of the compound of Example 37 (5.51 g) in acetonitrile (240 ml) and water (60 ml), and the reaction stirred under reflux while allowing the solvent to distill off for 2 hours. Additional acetonitrile/water (4/1 by volume) was added at such a rate as to maintain a steady reflux. On cooling, the reaction mixture was extracted with dichloromethane (2×300 ml), and the combined organic extracts dried (Na$_2$SO$_4$), and evaporated to dryness in vacuo. The residue was purified by column chromatography over silica gel using gradient elution (90/10–83/17 dichloromethane/methanol) to afford the title compound as a foam, 4.26 g.

$R_f$: 0.34 (85/15 dichloromethane/methanol)

$\delta_H$ (400 MHz, CDCl$_3$): 8.14 (1H, s), 7.92 (2H, d), 7.50 (2H, d), 7.20 (1H, dd), 6.79 (1H, d), 6.70 (2H, m), 5.26 (1H, s), 4.45 (2H, q), 3.04 (2H, m), 2.74 (2H, m), 2.60 (1H, m), 1.88 (1H, m), 1.44 (3H, t), 1.19 (3H, d), 1.09 (3H, d).

Preparation 32

Ethyl 2-4-[(R)-1-[(2S,5S)-2,5-dimethylhexahydropyrazin-1-yl]-1-(3-tert-butylmethylsilyloxyphenyl)methyl]phenyl-1,3-thiazole-4-carboxylate

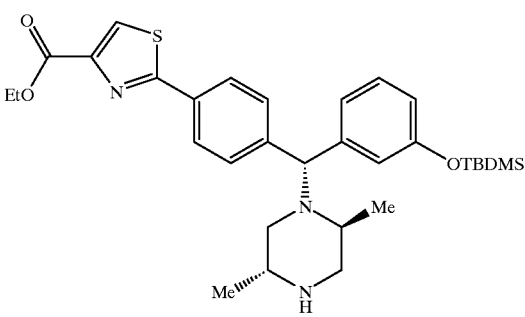

The title compound was prepared using the compound from Preparation 24, following a similar procedure to that described in Preparation 31, and was obtained in 70% yield.

$R_f$: 0.10 (95/5/0.5 dichloromethane/methanol/ammonium hydroxide)

m/z: 580 (MH$^+$)

$\delta_H$ (400 MHz, CDCl$_3$): 7.86 (2H, d), 7.52 (2H, d), 7.22 (1H, dd), 7.18 (1H, s), 6.79 (2H, m), 6.61 (1H, s), 5.36 (1H, s), 4.22 (2H, q), 3.90 (2H, s), 2.94 (2H, m), 2.62–2.76 (2H, m), 2.38 (1H, m), 1.62 (1H, m), 1.30 (1H, m), 1.20 (3H, d), 0.96 (12H, m), 0.17 (6H, s).

Preparation 33

Ethyl 2-{4-[(R)-1-[(2S,5R)-4-propyl-2,5-dimethylhexahydropyrazin-1yl-]-1-(3-[1-(tert-butyl)-1,1-dimethylsilyl]oxyphenyl)methyl]phenyl}-1-1,3-thiazole-4-carboxylate

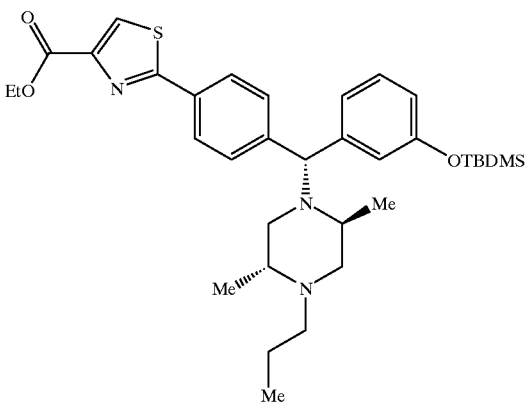

The title compound was prepared using the compound from Preparation 32 following a similar procedure to that described in Example 44, and was obtained in 73% yield.

R$_f$ : 0.32 (ethyl acetate/hexane)

m/z: 622 (MH$^+$)

δ$_H$ (300 MHz, CDCl$_3$): 7.84 (2H, d), 7.52 (2H, d), 7.18 (2H, m), 6.82 (1H, d), 6.75 (1H, d), 6.69 (1H, s), 5.14 (1H, s), 4.22 (2H, q), 3.88 (2H, s), 2.84 (1H, m), 2.47–2.72 (4H, m), 2.19 (2H, m), 1.94 (1H, m), 1.47 (2H, m), 1.29 (3H, d), 1.18 (3H, d), 0.98 (9H, S), 0.88 (3H, t), 0.18 (6H, s).

Preparation 34

Ethyl 2-{4-[(R)-1-[(2S,5R)-4-benzyl-2,5-dimethylhexahydropyrazin-1-yl]-1-(3-[1-(tert-butyl)-1,1-dimethylsilyl]oxyphenyl)methyl]phenyl}-1,3-thiazole-4-carboxylate

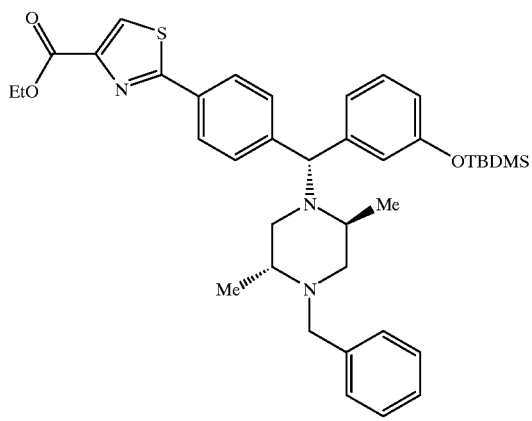

The title compound was prepared using the compound from Preparation 32 and benzaldehyde following a similar procedure to that described in Example 44, and was obtained in 55% yield.

R$_f$ : 0.81 (95/5 dichloromethane/methanol)

m/z: 670 (MH$^+$)

δ$_H$ (300 MHz, CDCl$_3$): 7.84 (2H, d), 7.50 (2H, d), 7.15–7.32 (7H, m), 6.84 (1H, d), 6.74 (2H, m), 5.06 (1H, s), 4.21 (2H, q), 3.88 (2H, s), 3.24 (1H, d), 2.58–2.77 (4H, m), 2.05 (2H, m), 1.29 (3H, t), 1.10 (6H, 2xd), 0.97 (9H, s), 0.18 (6H, s).

Preparation 35

Ethyl 2-(2-{4-[(3-[1-(tert-butyl)-1,1-dimethylsilyl]oxyphenyl)(hydroxy)methyl]phenyl}-1,3-thiazol-4-yl)acetate

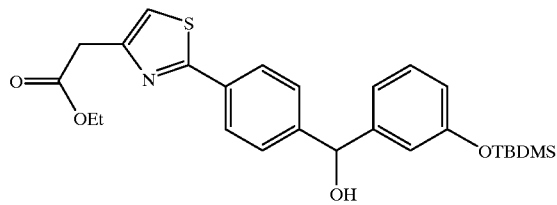

A solution of 3-tert-butyldimethylsilyloxyphenylmagnesium bromide (prepared from 15.78 g of the corresponding bromide and 1.2 g of magnesium turnings) in tetrahydrofuran (65 ml) was added dropwise to a cooled solution (−78° C.) of the compound from Preparation 23 (4.65 g) in tetrahydrofuran (50 ml). The reaction was stirred under a nitrogen atmosphere at −78° C. for 3 hours, followed by a further 18 hours at room temperature. The reaction mixture was evaporated to a minimum volume in vacuo and partitioned between ethyl acetate and aqueous ammonium chloride solution. The phases were separated, the aqueous layer extracted with ethyl acetate, and the combined organic extracts dried (MgSO$_4$) and evaporated to dryness in vacuo. The residue was purified by column chromatography over silica gel using gradient elution (80/20–65/35 hexane/ethyl acetate) to afford the title compound, 1.83 g.

R$_f$ : 0.23 (95/5 dichloromethane/methanol)

δ$_H$ (400 MHz, DMSO-d$_6$): 7.82 (2H, d), 7.46 (2H, d), 7.18 (1H, dd), 6.97 (1H, d), 6.87 (1H, s), 6.68 (1H, d), 5.97 (1H, s), 5.69 (1H, s), 4.12 (2H, q), 3.84 (2H, s), 1.18 (3H, t), 0.90 (9H, s), 0.14 (6H, s).

Preparation 36 ethyl 2-{4-[(3-[1-(tert-butyl)-1,1-dimethylsilyl]oxyphenyl)(hydroxy)methyl]phenyl}-1,3-thiazole-4-carboxylate

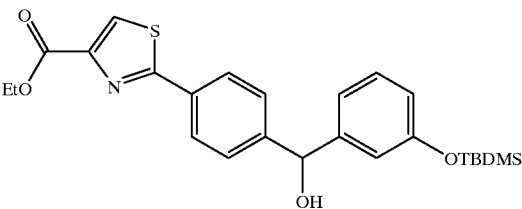

The title compound was prepared using the compound from Preparation 22, following a similar procedure to that described in Preparation 35 and was obtained in 44% yield.

R$_f$ : 0.50 (50/50 ethyl acetate/hexane)

m/z: 469 (M$^+$)

δ$_H$ (400 MHz, DMSO-d$_6$): 8.52 (1H, s), 7.90 (2H, d), 7.50 (2H, d), 7.17 (1H, dd), 6.98 (1H, d), 6.87 (1H, s), 6.67 (1H, d), 6.00 (1H, s), 5.72 (1H, s), 4.33 (2H, q), 1.32 (3H, t), 0.91 (9H, s), 0.14 (6H, s).

Preparation 37

Ethyl 2-(2-{4-[(3-[1-(tert-butyl)-1,1-dimethylsilyl]oxyphenyl)(chloro)methyl]phenyl}-1,3-thiazol-4-yl)acetate

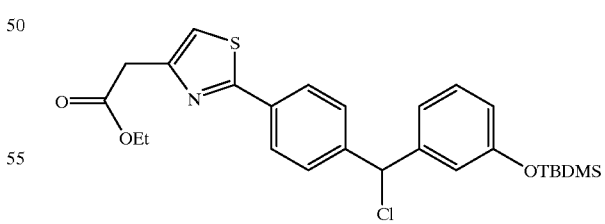

N-ethyldiisopropylamine (1.6 ml) and methanesulphonyl chloride (0.8 ml) were added to an ice-cooled solution of the compound from Preparation 35 (1.83 g) in dichloromethane (30 ml), and the reaction stirred at room temperature for 3 hours. The reaction mixture was washed with water and then saturated aqueous sodium bicarbonate solution. The layers were separated, and the aqueous extracted with dichloromethane. The combined organic extracts were dried (MgSO$_4$), and evaporated to dryness in vacuo, to afford the title compound as an orange oil.

m/z: 503 (MH$^+$)

$\delta_H$ (300 MHz, DMSO-d$_6$): 7.92 (2H, d), 7.56 (3H, m), 7.25 (1H, dd), 7.07 (1H, d), 6.93 (1H, s), 6.78 (1H, d), 6.54 (1H, s), 4.10 (2H, q), 3.87 (2H, s), 1.18 (3H, t), 0.90 (9H, s), 0.14 (6H, s).

Preparation 38

Ethyl 2-{4-[(3-[1-(tert-butyl)-1,1-dimethylsilyl] oxyphenyl)(chloro)methyl]phenyl}-1,3-thiazole-4-carboxylate

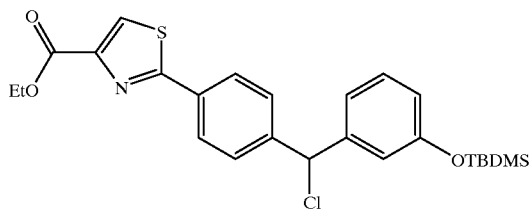

Thionyl chloride (1.57 ml) was added to an ice-cooled solution of the compound from Preparation 36 (3.4 g) in toluene (35 ml), and the reaction stirred at 100° C. for 18 hours. On cooling, the reaction mixture was evaporated to dryness in vacuo. The residue was purified by column chromatography over silica gel using gradient elution (93/7–85/15 hexane/ethyl acetate) to afford the title compound, 2.6 g.

R$_f$ : 0.39 (80/20 hexane/ethyl acetate)

$\delta_H$ (300 MHz, CDCl$_3$): 8.16 (1H, s), 8.00 (2H, d), 7.50 (2H, d), 7.21 (1H, dd), 6.98 (1H, d), 6.92 (1H, s), 6.80 (1H, d), 6.08 (1H, s), 4.45 (2H, q), 1.44 (3H, t), 0.98 (9H, s), 0.20 (6H, s).

Preparation 39

(8aR)perhydropyrrolo[1,2-α]pyrazine-1,4-dione

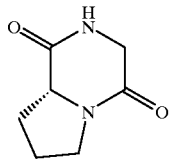

Pyridine (2.5 ml ), and thionyl chloride (22.5 ml) were added to a solution of N-phthaloylglycine (57.5 g) in dichloromethane and the reaction stirred under reflux for 18 hours. The mixture was allowed to cool to room temperature, (R)-proline (30.5 g) added and the reaction again stirred under reflux for 18 hours. On cooling, water was added and the resulting precipitate filtered, washed with further water and dried. This material was suspended in ethanol (330 ml) and dichloromethane (250 ml), and hydrazine hydrate (26.5 ml) added. The reaction mixture was stirred at room temperature for 18 hours, filtered and the filtrate evaporated to dryness in vacuo. This material was crystallised from ethanol, to afford the title compound, 26.05 g.

$\delta_H$ (300 MHz, DMSO-d$_6$): 8.07 (1H, s), 3.92–4.14 (2H, m), 3.26–3.55 (3H, m), 2.09 (1H, m), 1.66–1.89 (3H, m).

Preparation 40

(8aR)perhydropyrrolo[1,2-α]pyrazine

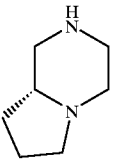

Lithium aluminium hydride (130 ml, 1M in tetrahydrofuran) was added slowly to a solution of the compound from Preparation 39 (10 g) in tetrahydrofuran (800 ml) and the reaction stirred under reflux for 20 hours. The mixture was cooled to 0° C., and a solution of aqueous tetrahydrofuran (80 ml, 20%) was added at such a rate as to maintain the reaction temperature below 10° C. Aqueous sodium hydroxide solution (33 ml, 5N), followed by water (117 ml) were then added and the mixture stirred for an hour at 0° C. The reaction mixture was filtered and washed well with diethyl ether. The filtrate was separated and the organic layer, dried (Na$_2$SO$_4$) and evaporated in vacuo to afford the title compound as an oil which was used without further purification.

m/z: 127 (MH$^+$)

Preparation 41

(3S, 8aS) -3-methylperhydropyrrolo[1,2-α])pyrazine

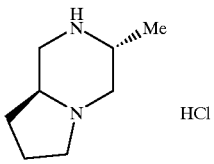

Lithium aluminium hydride (978 mg) was added to a solution of cyclo-(D-Ala-Pro) (2 g) in diethyl ether (30 ml) and the reaction stirred under reflux for 18 hours. The mixture was cooled to 0° C., water (2.7 ml) added followed by aqueous sodium hydroxide solution (6.6 ml, 5N) and further water (23.5 ml) and the mixture stirred for an hour. The resulting suspension was filtered and washed well with diethyl ether. The filtrate was separated and the organic layer dried (Na$_2$SO$_4$) and cooled to 0° C. Hcl gas was bubbled through the solution for 10 minutes, and the mixture then evaporated to dryness in vacuo, to afford the title compound, 1.2 g.

R$_f$ : 0.14 (93/7/1 dichloromethane/methanol/ammonium hydroxide)

m/z: 141 (MH$^+$)

Preparation 42

Ethyl 2-(2-{4-[(4-allylpiperazino)(3-[1-(tert-butyl)-1,1-dimethylsilyl]oxyphenyl)methyl]phenyl}-1,3-thiazol-4-yl)acetate

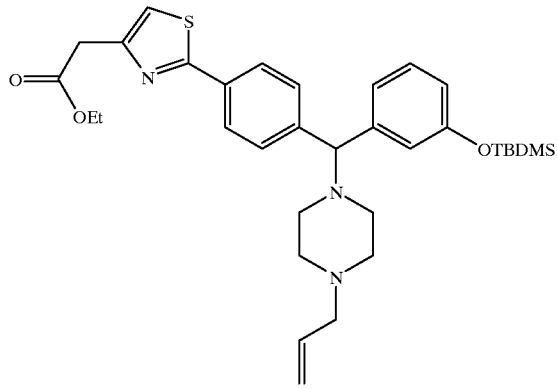

A suspension of the compound from Preparation 37 (1.91 g), 1-allylpiperazine (0.96 g) and sodium bicarbonate (0.96 g) in acetonitrile (20 ml) was stirred under reflux for 3 hours. On cooling, the reaction mixture was evaporated to dryness in vacuo. The residue was purified by column chromatography over silica gel using gradient elution (75/25–50-50 hexane/ethyl acetate) to afford the title compound as a light brown oil, 1.1 g.

m/z: 592 (MH$^+$)

$d_H$ (400 MHz, DMSO-$d_6$): 7.81 (2H, d), 7.49 (3H, m), 7.15 (1H, dd), 6.98 (1H, d), 6.94 (1H, s), 6.65 (1H, d), 5.77 (1H, m), 5.06–5.17 (2H, m), 4.30 (1H, s), 4.11 (2H, q) 3.83 (2H, s), 2.92 (2H, d), 2.28–2.42 (8H, m), 1.18 (3H, t), 0.90 (9H, s), 0.14 (6H, s).

Preparation 43

4-Iodobenzaldehyde

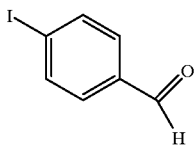

To a suspension of 4-iodobenzoic acid (14.88 g) in dry tetrahydrofuran (75 ml) was added borane dimethyl sulphide (6.12 ml) dropwise under a nitrogen atmosphere. The reaction mixture was heated under reflux for 1 hr, after which time the reaction mixture was cooled to room temperature and evaporated under reduced pressure. The residue was dissolved in dichloromethane (20 ml) and added to a suspension of the pyridinium chlorochromate (14.23 g) in dichloromethane (100 ml). The resulting mixture was heated under reflux for 1 hr and allowed to cool to room temperature. The resulting mixture was diluted with diethyl ether (250 ml) and filtered through a plug of arbocel. The filtrate was evaporated under reduced pressure, and the crude product was purified by column chromatography over silica gel eluting with dichloromethane to afford the title compound as a white solid (11.33 g).

$R_f$ 0.85 (Dichloromethane/Methanol, 98/2, v/v).

$\delta_H$ (300 MHz, CDCl$_3$) 9.98 (1H, s), 7.90 (2H, d), 7.55 (2H, d).

Preparation 44

(2R,5S)-1-benzyl-4-[(R)-1-(4-iodophenyl)-1-(3-[1-(tert-butyl)-1,1-dimethylsilyl]oxyphenyl)methyl]-2,5-dimethylhexahydropyrazine

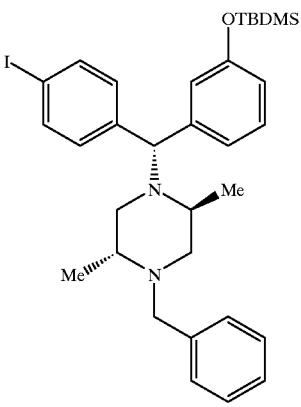

The compound of the above formula was prepared using a method similar to that described for preparation 4 using the compounds of Preparation 3, Preparation 43, benzotriazole and 3-tert-butyldimethylsilyloxymagnesium bromide to afford the title compound as a oil.

$R_f$ 0.2 (ethyl acetate/pentane, 1/30, v/v).

$\delta_H$ (300 MHz, CDCl$_3$): 7.60 (2H, d), 7.30–7.10 (9H, m), 6.75 (2H, t), 6.65 (1H, s), 5.05 (1H, s), 3.90 (1H, d), 3.20 (1H, d), 2.70 (1H, d), 2.60 (3H, m), 2.00 (2H, m), 1.10 (6H, d), 0.97 (9H, s), 0.20 (6H, s).

Preparation 45

4-Bromo-1-trityl-1H-pyrazole

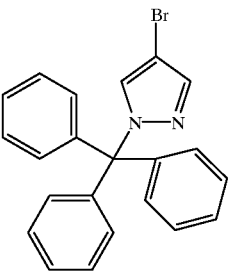

Trityl chloride (9.02 g) was added to a stirred solution of 4-bromopyrazole (4.24 g) and 4-dimethylaminopyridine (0.711 g) in pyridine (90 ml). The reaction mixture was heated to 85° C. for 20 hrs, cooled to room temperature and partitioned between diethyl ether and water. The organic layer was separated, dried (MgSO₄) and evaporated under reduced pressure. The crude product was recrystallized from hexane/toluene (5/1, 180 ml) to afford the title compound (4.0 g). The remaining solids and the mother liquors were combined and purified by column chromatography on silica gel eluting with pentane/ether (30/1, v/v) to afford a second batch of title compound (3.0 g).

$\delta_H$ (300 MHz, CDCl₃): 7.60 (1H, s), 7.40 (1H, s), 7.30 (9H, m), 7.20 (6H, m).

Preparation 46

4-( 1,1,1-Tributylstannyl)-1-trityl-1H-pyrazole

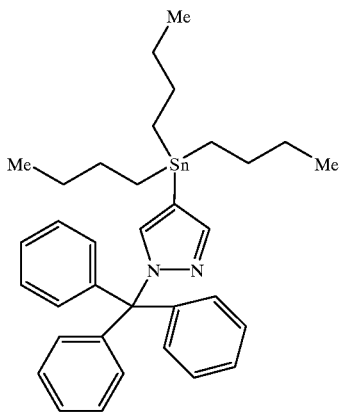

tert-Butyllithium (5.5 ml or 1.6M solution in hexanes) was added to a stirred solution of the product from Preparation 45 (2.34 g) in ether (30 ml ) and tetrahydrofuran (30 ml ) at −78° C. The reaction mixture was stirred for 1.5 hrs at −78° C. and tributyltin chloride (2.1 ml) added dropwise. The resulting mixture was stirred for 16 hrs in a expiring ice/acetone bath warming slowly to room temperature. The reaction mixture was quenched with saturated ammonium chloride (4 ml) and partitioned between water and diethylether, the organic layer was separated, dried over MgSO₄ and evaporated under reduced pressure. The crude product was purified by column chromatography on silica get eluting with pentane/ethyl acetate/triethylamine (50/1/1, v/v) to afford the title compound as a oil (2.8 g).

$R_f$ 0.3 (pentane/ethyl acetate/triethylamine, 50/1/1, v/v).

$\delta_H$ (400 MHz, CDCl₃): 7.60 (1H, s), 7.25 (9H, m), 7.15 (1H, s), 7.10 (6H, m), 1.40 (6H, m), 1.20 (6H, m), 0.95 (6H, m), 0.80(9H, m).

Preparation 47

(2R,5S)-1-Benzyl-4-(R)-1-(3-[1-(tert-butyl)-1,1-dimethylsilyl]oxyphenyl)-1-[4-(1-trityl-1H-pyrazol-4-yl) phenyl]methyl-2,5-dimethylhexahydropyrazine

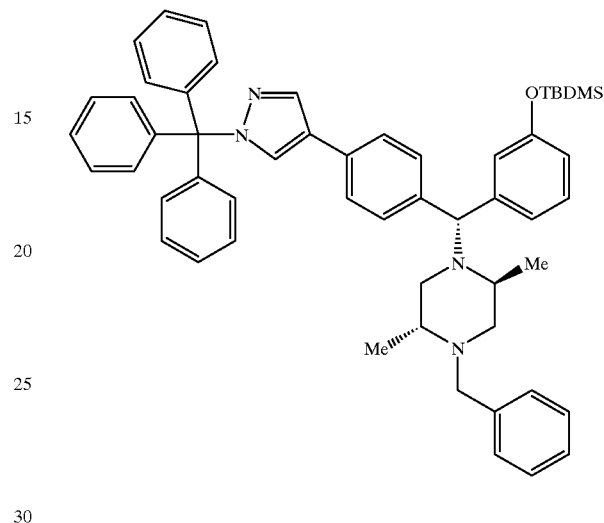

Copper iodide (70 mg) was added to a stirred solution of the compound of Preparation 44 (2.6 g), the compound of Preparation 46 (2.5 g), 10% Palladium on charcaol (47 mg) and triphenyl arsine(234 mg) in acetonitrile (55 ml). The reaction mixture was then heated to reflux under an atmosphere of argon for 60 hrs. A gum and a black powder were observed, the solution was then cooled to room temperature, and dichloromethane and methanol added until the gum had dissolved. The black powder was filtered off, and the filtrate evaporated under reduced pressure. The crude product was purified by column chromatography on silica gel eluting with ethyl acetate/pentane (1/10, v/v) to afford the title compound (2.3 g).

$R_f$ 0.25 (ethyl acetate/pentane, 1/10, v/v).

$\delta_H$ (300 MHz, CDCl₃): 7.90 (1H, s), 7.60 (1H, s), 7.40–7.10 (25H, m), 6.80 (1H, d), 6.65 (2H, d), 5.05 (1H, s), 3.85 (1H, d), 3.20 (1H, d), 2.80–2.50 (4H, m), 2.00 (2H, m), 1.10 (6H, d), 0.97 (9H, s), 0.20 (6H, s).

119

Preparation 48

(2R,5S)-1-Benzyl-4-(R)-1-(3-[1-(tert-butyl)-1,1-dimethylsilyl]oxyphenyl)-1-[4-(1H-pyrazol-4-yl)phenyl]methyl-2,5-dimethylhexahydropyrazine

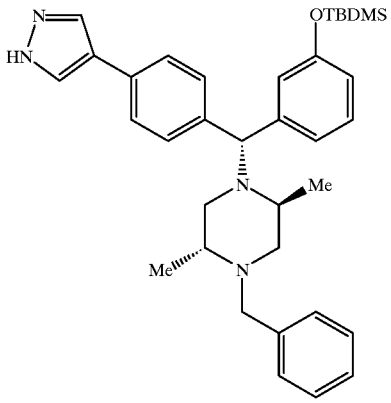

To a solution of the compound of Preparation 47 (2.5 g) in dichloromethane (20 ml) was added 1M HCl in diethyl ether (9.9 ml) at 0° C. under an atmosphere of nitrogen. The reaction mixture was stirred at 10° C. for 1 hr after which time it was poured into saturated sodium bicarbonate solution and the product was extracted with ethyl acetate. The organic layer was dried (MgSO$_4$) and evaporated under reduced pressure, and the crude product purified by column chromatography over silica gel eluting with (ethyl acetate/pentane, 1/1, v/v) to afford the title compound as a oil (0.8 g).

R$_f$ 0.2 (ethyl acetate/pentane, 1/1, v/v)

δ$_H$ (300 MHz, CDCl$_3$): 7.85 (2H, s), 7.42 (4H, s), 7.35–7.10 (6H, m), 6.82 (1H, d), 6.75 (2H, d), 5.05 (1H, s), 3.90 (1H, d), 3.23 (1H, d), 2.80–2.50 (4H, m), 2.05 (2H, m), 1.10 (6H, d), 0.95 (9H, s), 0.20 (6H, s).

Preparation 49

Methyl 2-(4-4-[(R)-1-[(2S,5R)-4-benzyl-2,5-dimethylhexahydropyrazin-1-yl]-1-(3-[1-(tert-butyl)-1,1-dimethylsilyl]oxyphenyl)methyl]phenyl-1H-pyrazol-1-yl)acetate

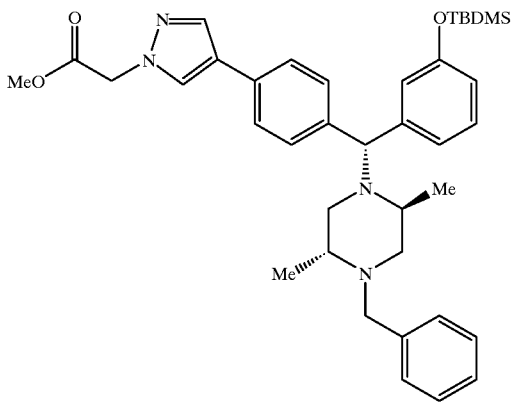

The compound of the above formula was prepared by a similar method to that described for Example 7 using the compound of Preparation 48, and methyl bromoacetate. The crude product was purified by column chromatography over silica gel eluting with (Dichloromethane/Methanol, 95/5. v/v) to afford the title compound (155 mg).

R$_f$ 0.2 (Dichloromethane/Methanol, 95/5, v/v).

δ$_H$ (300 MHz, CDCl$_3$): 7.80 (1H, s), 7.70 (1H, s), 7.40 (4H, m), 7.35–7.10 (6H, m), 6.80 (1H, d), 6.70 (2H, d), 5.05 (1H, s), 3.95 (1H, d), 3.80 (3H, s), 3.25 (1H, s), 2.80–2.50 (4H, m), 2.05 (2H, m), 1.65 (1H, m), 1.40 (1H, m), 1.10 (6H, d), 0.95 (9h, s), 0.20 (6H, s).

Preparation 50

Methyl 4-[(R)-1-1-[(2S,5R)-4-benzyl-2,5-dimethylhexahydropyrazin-1-yl]-1-(3-[1-(tert-butyl)-1,1-dimethylsilyl]oxyphenyl)methyl]benzoate

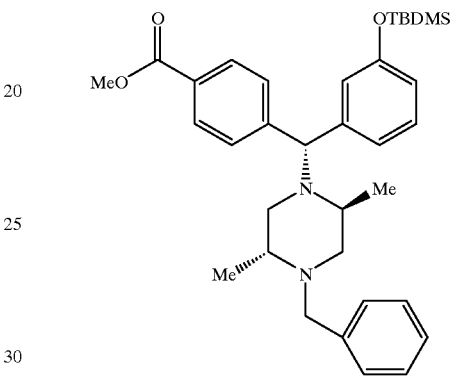

The compound of the above formula was prepared by a similar method to that described for Preparation 4, using 4-carbomethoxybenzaldehyde (2.41 g), benzotriazole (1.75 g), the compound of Preparation 3 (3.00 g) and 3-tert-butyldimethylsilylphenylmagnesium bromide to afford the title compound as a yellow oil (898 mg).

R$_f$ 0.73 (dichloromethane/diethylether, 95/5, v/v).

m/z: 559 (MH$^+$)

Preparation 51

4-[(R)-1-[(2S,5R)-4-Benzyl-2,5-dimethylhexahydropyrazin-1-yl]-1-(3-hydroxyphenyl)methyl]benzene-1-carbohydrazide

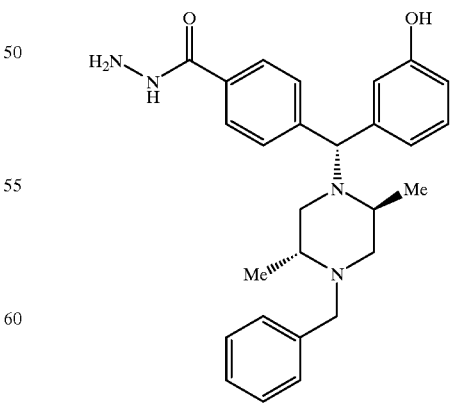

Hydrazine hydrate (1.0 ml) was added to a solution of the compound of Preparation 50 (557 mg) in methanol (10 ml).

The resulting solution was refluxed for 40 hrs, the reaction mixture was partitioned between ethyl acetate/water the organic phase separated, washed with saturated brine, dried over MgSO$_4$ and evaporated under reduced pressure. The crude product was purified by column chromatography on silica gel eluting with ethyl acetate/Pentane (75/25–90/10, v/v) to afford the title compound as a white foam (240 mg).

R$_f$ 0.43 (ethyl acetate)

m/z: 445 (MH$^+$)

Preparation 52

Methyl 3-formylbenzoate

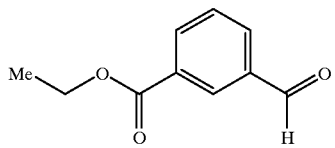

Potasium carbonate (6.84 g) was added to a solution of 3 formylbenzoic acid (5.00 g), ethyl iodide (5.15 g) in acetonitrile (100 ml). The reaction mixture was refluxed for 18 hrs after cooling the mixture was partitioned between ethyl acetate and water, the organic phase separated, washed with saturated brine, dried over MgSO$_4$ and evaporated under reduced pressure to afford the title compound as a yellow oil (4.84 g).

R$_f$ 0.46 (dichloromethane ).

m/z: 196 (MNH$_4^+$).

$\delta_H$ (300 MHz, CDCl$_3$): 10.09 (1H, s), 8.53 (1H, d), 8.31 (1H, d), 8.08 (1H, d), 7.63 (1H, d, d), 4.43 (2H, q), 1.43 (3H, t).

Preparation 53

Ethyl 3-[(R)-1-[(2S,5R)-4-benzyl-2,5-dimethylhexahydropyrazin-1-yl]-1-(3-[1-(tert-butyl)-1,1-dimethylsilyl]oxyphenyl)methyl]benzoate

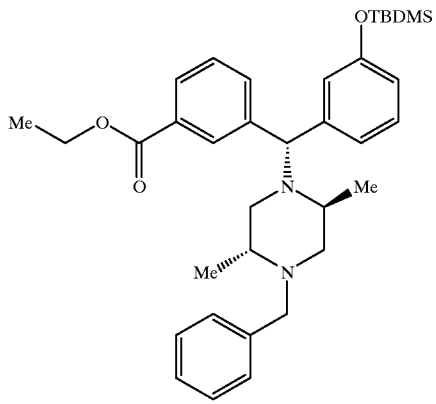

The compound of the above formula was prepared by a similar method to that described for Preparation 4 using the compound of Preparation 52, the compound of Preparation 3, benzotriazole and 3-tert-butyldimethylsilyloxyphenylmagnesium bromide. The crude product was purified by column chromatography on silica gel eluting with dichloromethane/diethyl ether (95/5, v/v) to afford the title compound as a brown oil (5.509 g).

R$_f$ 0.52 (dichloromethane/diethyl ether, 95/5. v/v).

m/z: 573 (MH$^+$).

Preparation 54

3-[(R)-1-[(2S,5R)-4-benzyl-2,5-dimethylhexahydropyrazin-1-yl]-1-(3-hydroxyphenyl)methyl]benzene-1-carbohydrazide

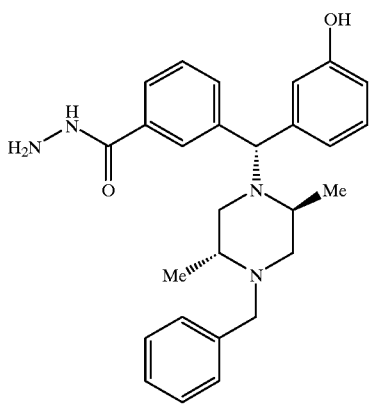

The compound of the above formula was prepared by a similar method to that described for Preparation 51 using the compound of Preparation 53 and hydrazine hydrate to afford the title compound as a oil (768 mg).

R$_f$ 0.46 (ethyl acetate).

m/z: 445 (MH$^+$)

Preparation 55

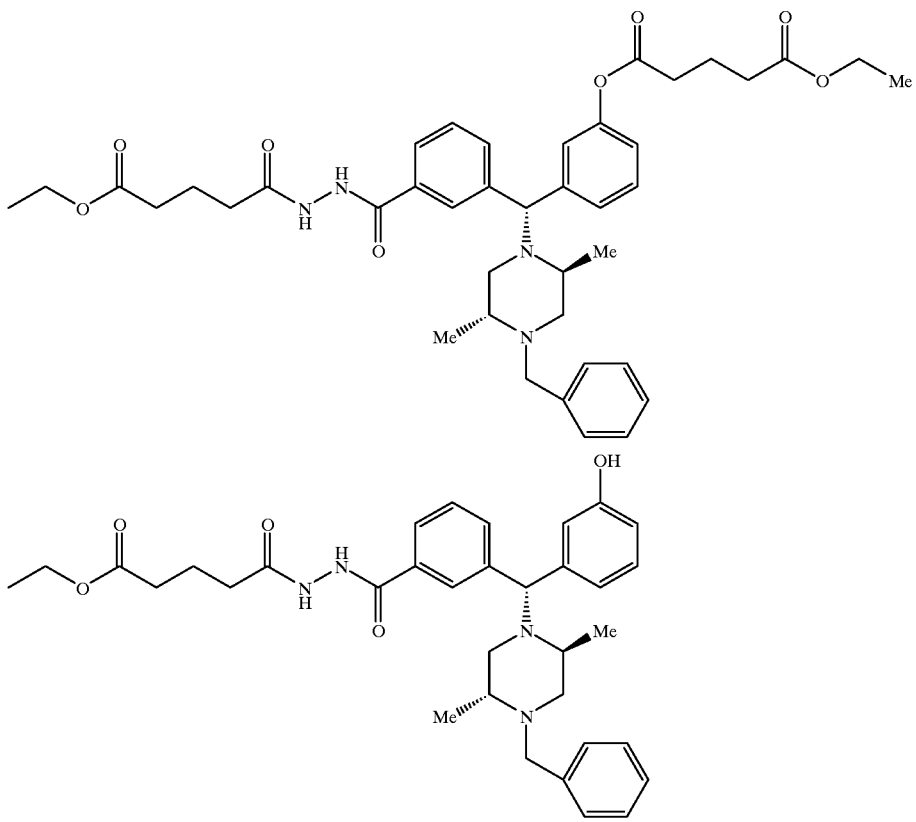

4-ethoxycarbonyl butanol chloride (729 mg) was added to a solution of the compound of Preparation 54 (726 mg) and triethylamine (0.91 ml) in dichloromethane (10 ml). The reaction mixture was stirred at room temperature for 18 hrs, and then partitioned between ethyl acetate/water the organic phase was separated and washed with aqueous ammonium chloride, saturated brine dried over $MgSO_4$ and evaporated under reduced pressure. The crude product was purified by column chromatography on silica gel eluting with ethyl acetate/Hexane (1/1,v/v) to afford a mixture of the above shown compounds as an oil (481 mg).

$R_f$ 0.79 (ethyl acetate).

m/z: 729 ($MH^+$).

Preparation 56

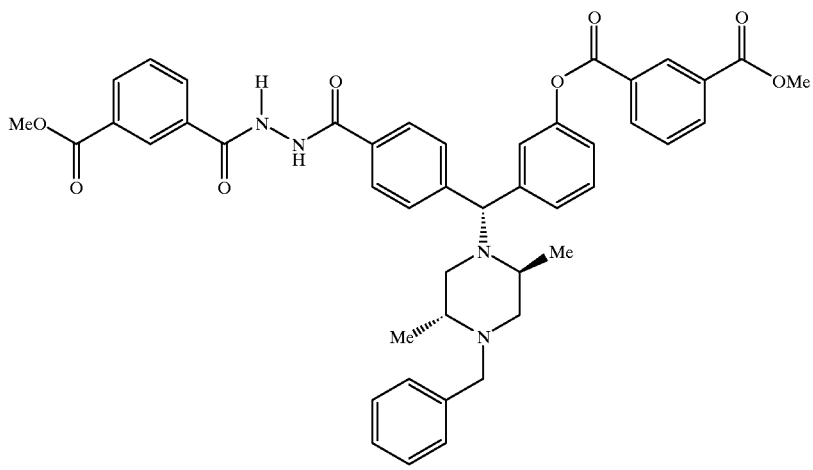

-continued

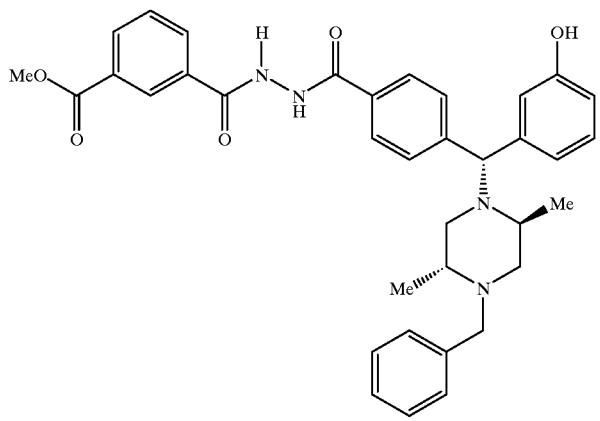

The compounds of the above formula were prepared by a similar method to that described for Preparation 55 from the compound of Preparation 51 and 3-carboxymethylbenzoyl chloride [Gazz. Chim. Ital, 117 (9), 529–31, (1987)]. The crude product was purified by column chromatography on silica gel eluting with ethyl acetate/Pentane (25/75-1/1, v/v) to afford a mixture of the above shown compounds as a white solid (159 mg).

$R_f$ 0.38 (Ether).

m/z: 769 (MH$^+$).

Preparation 57

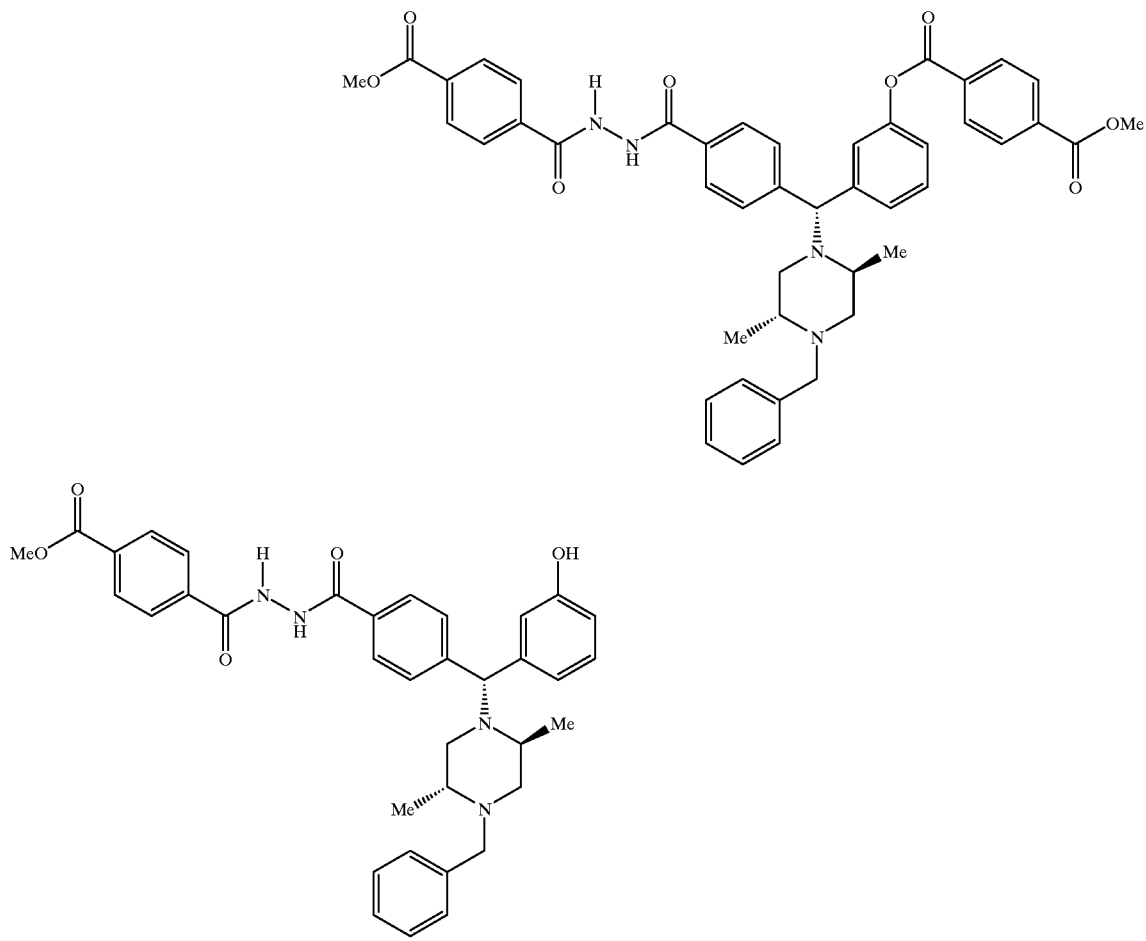

To a solution of the compound of Preparation 51(200 mg) in Dichloromethane (5 ml ) was added monomethyl terphthalate (89 mg), 1-hydroxybenzotriazole (73 mg), 1-(3- dimethylaminopropyl)-3-ethylcarbodiimide (104 mg) and N-methylmorpholine (0.17 ml ). The reaction mixture was stirred at room temperature for 18 hrs after which time it was partitioned between ethyl acetate/water the organic layer was separated and washed with saturated sodium bicarbonate solution, brine, dried over MgSO$_4$ and evaporated under reduced pressure. The crude product was purified by column chromatography on silica gel eluting with ethyl acetate/Pentane (1/1, v/v) to afford a mixture of the above shown compounds as a white solid (259 mg).

R$_f$ 0.40 (Diethyl ether).

m/z: 607 (MH$^+$)

Preparation 58

3-[(R)-1-[(2S,5R)-4-benzyl-2,5-dimethylhexahydropyrazin-1-yl]-1-(3-[1-(tert-butyl)-1,1-dimethylsilyl]oxyphenyl)methyl]benzonitrile

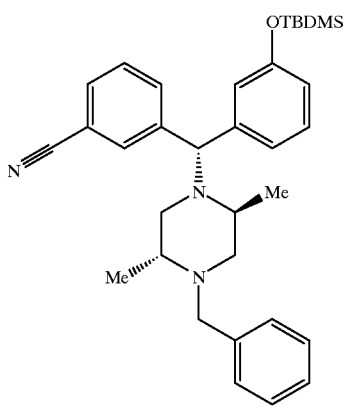

The compound of the above formula was prepared by a similar method to that described for Preparation 4 using 3-cyanobenzaldehyde, the compound of Preparation 3, benzotriazole, and 3-tert-butyldimethylsilyloxyphenylmagnesium bromide. The crude product was purified by column chromatography on silica gel eluting with Dichloromethane/Methanol (95/5, v/v) to afford the title compound (5.4 g).

R$_f$ 0.24 (Hexane/isopropanol/ammonium hydroxide, 98/2/0.2, v/v).

m/z: 526 (MH$^+$).

$\delta_H$ (300 MHz, CDCl$_3$): 7.80 (1H, s), 7.62 (1H, d), 7.50 (1H, d), 7.38 (1H, t), 7.20 (6H, m), 6.80 (2H, m), 6.60 (1H, s), 5.10 (1H, s), 3.85 (1H, d), 3.20 (1H, d), 2.60 (4H, m0, 1.90 (2H, m), 1.06 (6H, m), 0.95 (9H, s), 0.18 (6H, s).

Preparation 59

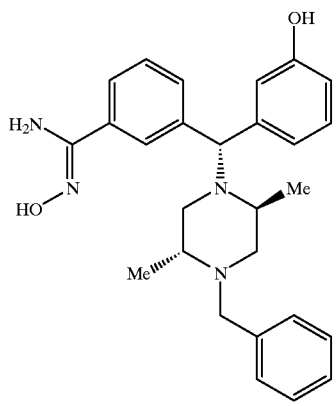

The compound of the above formula was prepared by a similar method to that described for Preparation 19 using the compound of Preparation 58. The crude product was purified by column chromatography on silica gel eluting with Dichloromethane/Methanol/ammonium hydroxide (97/3/1, v/v) to afford the title compound (687 mg).

R$_f$ 0.22 (Dichloromethane/Methanol, 95/5, v/v).

m/z: 446 (MH$^-$)

Preparation 60

1H-Indole-5-carbaldehyde

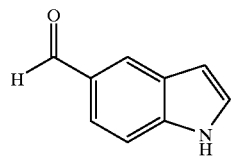

5-bromoindole (5.0 g) was added to a stirred suspension of potassium hydride (2.92 g) in diethyl ether (100 ml) at 0° C. The reaction mixture was stirred for 15 mins, cooled to −78° C. before tert-butyl lithium (31.5 ml) was added, and after 30 minutes dimethylformamide (10 ml). The reaction mixture was stirred at room temperature for 18 hrs and then poured into ice-cold 1N HCl the layers were separated and the aqueous was extracted with ethyl acetate (×3). The combined organic layers were washed with saturated sodium bicarbonate solution, brine, dried MgSO$_4$ and evaporated under reduced pressure. The crude product was purified by column chromatography on silica gel eluting with Dichloromethane/Methanol (97/3, v/v) to afford a white solid (1.8 g).

Preparation 61

Ethyl 2-(5-formyl-1H-indol-1-yl)acetate

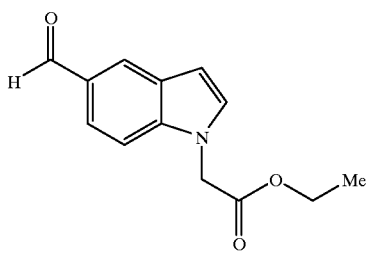

Potassium carbonate (7.84 g) was added to a solution of the compound of Preparation 60 (1.65 g) and ethylbromoacetate (1.5 ml) in methylethyl ketone (50 ml). The reaction mixture was heated to reflux and stirred for 18 hrs after which time the cooled mixture was filtered and the filtrate evaporated under reduced pressure to afford the title compound as a white solid (2.117 g).

m/z: 233 (MH$^+$)

Preparation 62

Ethyl 2-{5-[(R)-1-[(2S,5R)-4-allyl-2,5-dimethylhexahydropyrazin-1-yl]-1-(3-{[1-tert-butyl)-1,1-dimethylsilyl]oxy}phenyl)methyl]-1H-indole-1-yl}acetate

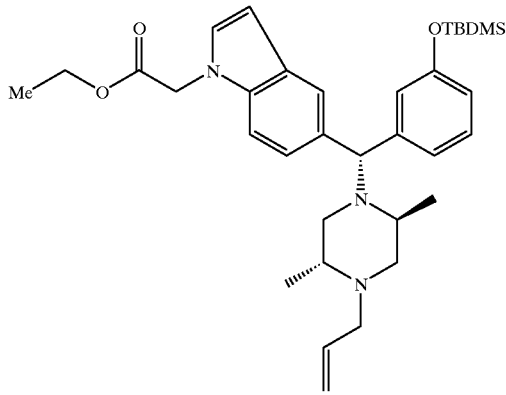

The compound of the above formula was prepared by a similar method to that described for Preparation 4 using the compound of Preparation 61, (−)-(2R,5S)-1-allyl-2,5-dimethylpiperazine, benzotriazole and 3-tert-butyldimethylsilyloxy phenylmagnesium bromide. The crude product was purified by column chromatography on silica gel eluting with Dichloromethane/Methanol (98/2, v/v) to afford the title compound (650 mg).

R$_f$ 0.7 (Dichloromethane/Methanol, 96/4, v/v).

m/z: 576 (MH$^+$).

Preparation 63

1H-indazole-5-carbaldehyde

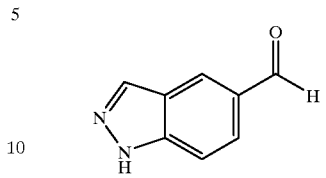

5-Cyanoindazole (2.32 g) [Hailey etc Synthetic communications, (1997), 27 (7), 1199–1207] was dissolved in a mixture of water (16.7 ml), glacial acetic acid (16.7 ml) and pyridine (33.4 ml) under a atmosphere of nitrogen. Sodiun hydrogen phosphate (4.64 g) was added to the mixture followed by raney nickel/ water (2 g/ml). The reaction mixture was heated to 50° C. for 5 hrs and then allowed to cool to room temperature and stirred for 18 hrs. The catalyst was then filtered off and washed with pyridine and water. The pH of the solution was adjusted to 9.0 with sodium carbonate and the product extracted with ethyl acetate (×2). The organic layers were dried over MgSO$_4$ and evaporated under reduced pressure. The crude solid was purified by washing with toluene to afford the title compound as a beige solid (2.36 g).

R$_f$ 0.15 (dichloromethane/diethyl ether, 95/5, v/v).

$\delta_H$ (300 MHz, CDCl$_3$): 10.35 (1H, bs), 10.03 (1H, s), 8.28 (1H, s), 8.22 (1H, s), 7.94 (1H, d), 7.57 (1H, d).

Preparation 64

Ethyl 5-(5-formyl-1H-indazol-1-yl) pentanoate

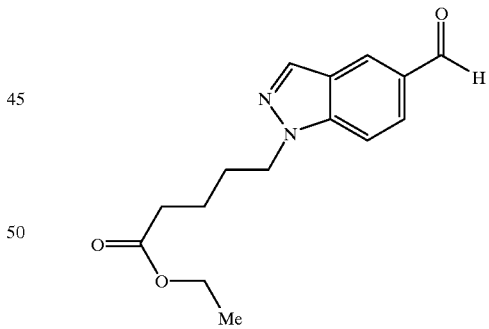

The compound of the above formula was prepared by a similar method to that described for Preparation 61 using the compound of Preparation 61 and Ethyl 5-bromovalerate. The crude product was purified by column chromatography on silica gel eluting with ethyl acetate/Hexane (35/50–60/40) to afford the title compound as a oil which crystallised upon standing (1.037 g).

R$_f$ 0.47 (ethyl acetate/Hexane, 1/1, v/v).

m/z: 275(MH$^+$).

Preparation 65

Ethyl 5-{5-[(R)-1-[(2S,5R)-4-benzyl-2,5-dimethylhexahydropyrazin-1-yl]-1-(3-{[1-tert-butyl)-1,1-dimethylsilyl]oxy}phenyl)methyl]-1H-indazol-1-yl}pentanoate

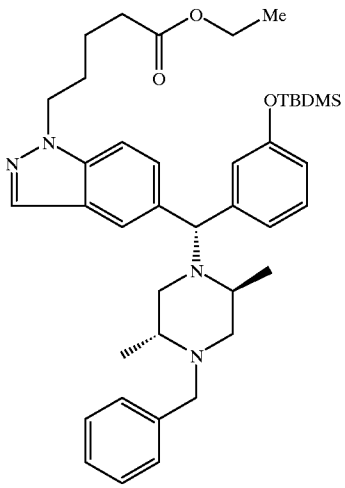

The compound of the above formula was prepared by a similar method to that described for Preparation 4 using the compound of Preparation 64, (−)-(2R,5S)-1-benzyl-2,5-dimethylpiperazine, benzotriazole and 3-tert-butyldimethylsilyloxy phenylmagnesium bromide. The crude product was purified by column chromatography on silica gel eluting with Hexane/Isopropanol/0.88 ammonium hydroxide (95/5/0.25, v/v) to afford the title compound as a oil (949 mg).

$R_f$ 0.23 (dichloromethane/Methanol, 98/2).

m/z: 466 (MH$^+$).

Preparation 66

Ethyl 2-{5-[(R)-1-[(2S,5R)-4-benzyl-2,5-(dimethylhexahydropyrazin-1-yl]-1-(3-{[1-tert-butyl)-1,1-dimethylsilyl]oxy}phenyl)methyl]-1H-indol-1-yl}acetate

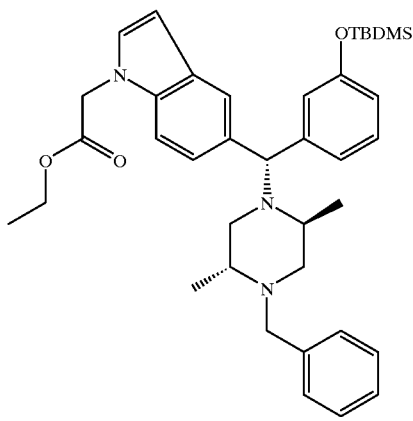

The compound of the above formula was prepared by a similar method to that described for Preparatio 4 using the compound of Preparation 61, (−)-(2R,5S)-1-benzyl-2,5-dimethylpiperazine, benzotriazole and 3-tert-butyldimethylsilyloxy phenylmagnesium bromide. The crude product was purified by column chromatography eluting with Hexane/Isopropanol/0.88 ammonium hydroxide (95/5/0.25, v/v) to afford the title compound (1.17 g).

$R_f$ 0.38 (Hexane/Isopropanol/0.88 ammonium hydroxide, 95/5/0.5, v/v).

m/z: 626 (MH$^+$).

Preparation 67

Ethyl 5-cyano-1-ethyl-1H-indole-2-carboxylate

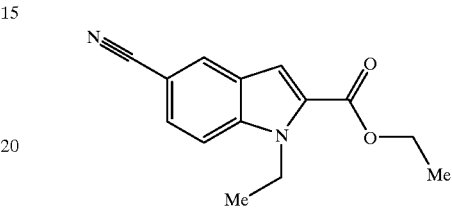

2 Ethylcarboxy-5-cyanoindole (497 mg) [Liebigs Ann Chem, (3), 438–55 (1986)] and potassium carbonate (960 mg) were mixed in acetonitrile (25 ml) and bromoethane (191 µl) added. The reaction mixture was stirred for 18 hrs at 80° C. under a atmosphere of nitrogen. Iodoethane (200 µl) was added and the reaction mixture heated to 60° C. for 18 hrs after which time the mixture was diluted with ethyl acetate (100 ml) and washed with water, dried over MgSO$_4$ and evaporated under reduced pressure. The crude product was purified by column chromatography on silica gel eluting with Hexane/Isopropanol/ 0.88 ammonium hydroxide (95/5/0.25, v/v) to afford the title compound as a white solid (455 mg).

$R_f$ 0.59 (Hexane/Isopropanol/0.88 ammonium hydroxide, 90/10/0.75, v/v).

m/z: 243 (MH$^+$).

Preparation 68

Ethyl 1-ethyl-5-formyl-1H-indole-2-carboxylate

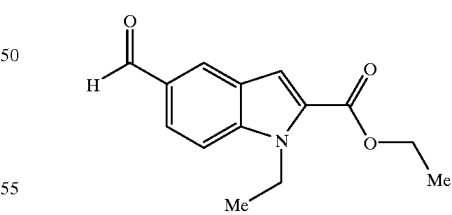

The compound of the above formula was prepared by a similar method to that described for Preparation 63 from the product of Preparation 67 and Raney nickel. The crude product was purified by column chromatography on silica gel eluting with Dichloromethane/Methanol (95/5, v/v) to afford the title compound as a oil (367 mg).

$R_f$ 0.48 (Dichloromethane/Diethyl ether, 98/2, v/v).

m/z: 246 (MH$^+$).

Preparation 69

1H-indole-6-carbaldehyde

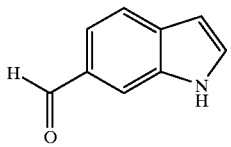

Potassium hexamethyldisilazane (0.5M in toluene) (56 ml) was added dropwise to a ice cold solution of 6-bromoindole (5.0 g) in diethyl ether (50 ml). The reaction mixture was warmed to room temperature for 30 mins and then cooled to −78° C. tBuLi (1.7M) (31.5 ml) was added to the mixture keeping the temperature below −65° C. the mixture was further stirred at −78° C. for 30 mins after which time a solution of DMF (6 ml) in diethyl ether (10 ml) was added, the reaction mixture was warmed to room temperature and quenched with ice cold 2N HCl the product was then extracted into diethyl ether (×3). The combined organic layers were dried over $MgSO_4$ and evaporated under reduced pressure. The crude product was purified by column chromatography on silica gel eluting with Dichloromethane/Methanol (97/3, v/v) to afford the title compound as a solid (1.49 g).

Preparation 70

Methyl 2-(6-formyl-1H-indol-1-yl)acetate

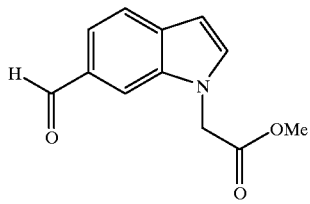

The compound of the above formula was prepared by a similar method to that described for Preparation 61 from the compound of Preparation 69 and methyl bromoacetate. The crude product was purified by column chromatography on silica gel eluting with diethyl ether/pentane (1/1–75/25, v/v) to afford the title compound (620 mg).

m/z: 218 (MH$^+$).

δ(CDCl$_3$): 10.2 (1H, s), 7.70 (1H, d), 7.62 (1H, d), 7.30 (1H, d), 6.62 (1H, d), 4.92 (2H, s), 3.76 (3H, s).

Preparation 71

Methyl 2-{6-[(R)-1-[(2S,5R)-4-benzyl-2,5-dimethylhexahydropyrazin-1-yl]-1-(3-{[1-(tert-butyl)-1,1-dimethylsilyl]oxy}phenylmethyl]-1H-indol-1-yl}acetate

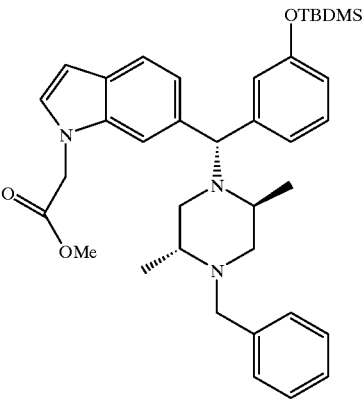

The compound of the above formula was prepared by a similar method to that described for Preparation 4 using the product of Preparation 70, (−)-(2R,5S)-1-benzyl-2,5-dimethylpiperazine, benzotriazole and 3-tert-butyldimethylsilyloxy phenylmagnesium bromide. The crude product was purified by column chromatography on silica gel eluting with Pentane/ethyl acetate (95/5–85/15, v/v) to afford the title compound (468 mg).

R$_f$ 0.3 (Dichloromethane/Methanol, 95/5, v/v).

m/z: 612 (MH$^+$).

Preparation 72

2-(4-formylphenyl)-4-pyridyl cyanide

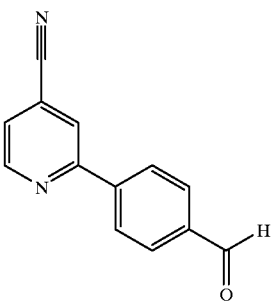

Benzaldehyde-4-boronic acid (1.36 g), 2-bromo-4-cyano pyridine (1.5 g), cesium fluoride (2.72 g) and tetrakis (triphenylphosphine)palladium(0) (285 mg) were mixed together in dimethyl ethylene glycol (30 ml ). The reaction mixture was refluxed for 16 hrs under a atmosphere of nitrogen after which time the cooled mixture was diluted with diethyl ether (40 ml ) and washed with water (40 ml), the organic layer was separated and washed with saturated brine, dried over MgSO$_4$ and evaporated under reduced pressure. The crude product was purified by column chromatography eluting with Dichloromethane/Diethyl ether (97.5/2.5, v/v) to afford the title compound (0.81 g).

R$_f$ 0.3 (Dichloromethane/Diethyl ether, 97.5/2.5, v/v).

δ$_H$ (400 MHz, CDCl$_3$): 10.15 (1H, s), 8.95 (1H, d), 8.20 (2H, d), 8.05 (3H, m), 7.55 (1H, d).

Preparation 73

2-{4-[(R)-1-[(2S,5R)-4-benzyl-2,5-dimethylhexahydropyrazin-1-yl]-1-(3-{[1-(tert-butyl)-1,1-dimethylsilyl]oxy}phenyl)methyl]phenyl}-4-pyridyl cyanide

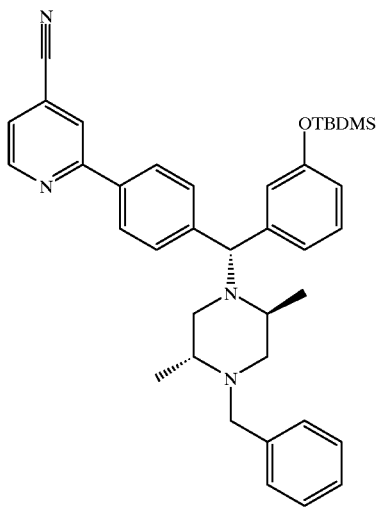

The compound of the above formula was prepared by a similar method to that described for Preparation 4 using the compound of Preparation 72, (−)-(2R,5S)-1-benzyl-2,5-dimethylpiperazine, benzotriazole and 3-tert-butyldimethylsilyloxy phenylmagnesium bromide. The crude product was purified by column chromatography on silica gel eluting with ethyl acetate/Pentane (1/4, v/v) to afford the title compound (0.47 g).

δ$_H$ (300 MHz, CDCl$_3$): 8.90 (1H, d), 7.95 (3H, d), 7.60 (2H, d), 7.40 (1H, d), 7.30–7.15 (5H, m), 6.85 (1H, d), 6.80–6.70 (2H, m), 5.15 (1H, s), 3.95 (1H, d), 3.25 (1H, d), 2.80–2.55 (4H, m), 2.05 (2H, m), 1.15 (6H, t), 1.00 (9H, s), 0.20 (6H, s).

Preparation 74

5-{4-[(R)-1-[(2S,5R)-4-benzyl-2,5-dimethylhexahydropyrazin-1-yl]-1-(3-{[1-(tert-butyl)-1,1-dimethylsilyl]oxy}phenyl)methyl]phenyl}-3-pyridyl cyanide

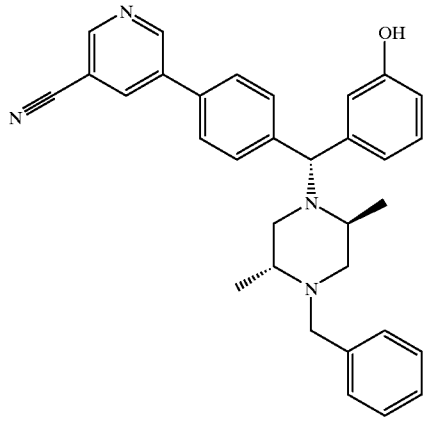

3-Cyano-5-(tributylstannyl)pyridine [prepared by the method of A. D. Brown. et. al., PCT int Appl, WO 9321178] (684 mg), 10% palladium on charcoal (20 mg), triphenyl arsine (98 mg), copper iodide (29 mg) and the compound from Prepration 44 (1.09 g) were mixed together in acetonitrile (25 ml). The reaction mixture was heated to reflux for 36 hrs after which time the mixture was cooled and tetraethylammonium fluoride (888 mg) was added. The reaction mixture was stirred for 20 mins and then aquoeus potassium fluoride (20 ml ) was added. After stirring for 30 minutes the organic layer was separated, filtered through a plug of Arbocel® and evaporated under reduced pressure. The crude product was purified by column chromatography eluting with EtOAc/Hexane (1/2, v/v) to afford the title compound (0.73 g).

R$_f$ 0.3 (ethyl acetate/Hexane, 2/1, v/v).

δ$_H$ (300 MHz, CDCl$_3$): 9.05 (1H, s), 8.90 (1H, s), 8.10 (1H, s), 7.60 (2H, d), 7.50 (2H, d), 7.35–7.10 (6H, m), 6.85–6.60 (3H, m), 5.10 (2H, m), 3.90 (1H, d), 3.25 (1, d), 2.80–2.50 (4H, m), 2.00 (2H, m), 1.10 (6H, 2xd).

Preparation 75 tert-butyl di(2-propynyl)carbamate

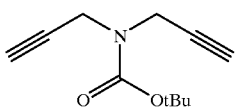

A solution of di-tert-butyl dicarbonate (49.21 g) in dichloromethane (50 ml) was added dropwise to an ice-cold solution of dipropargylamine (20 g) and triethylamine (26 g) in dichloromethane (150 ml). The reaction mixture was allowed to warm up to room temperature and stirred overnight. The reaction mixture was washed three-times with water (200 ml), saturated brine solution, dried (MgSO$_4$) and evaporated to dryness in vacuo to afford the title compound as a brown solid, 42.60 g. The compound was used without further purification.

m/z: 211 (MNH$_4^+$)

$\delta_H$(400 MHz, CDCl$_3$): 4.20 (4H, br s), 2.25 (2H, m), 1.50 (9H, s).

Preparation 76 tert-butyl 5-(hydroxymethyl)-1,3-dihydro-2H-isoindole-2-carboxylate

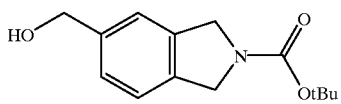

Propargyl alcohol (8.49 g) was added via syringe to an ice-cold solution of the compound of Preparation 75 (7.32 g) in ethanol (160 ml). Wilkinson's catalyst (1.06 g) was added in one portion and the resulting mixture stirred and allowed to warm to room temperature overnight. The reaction mixture was concentrated under reduced pressure and the residue purified over silica gel (ethyl acetate:pentane; 1:2) to afford the title compound, 5.79 g as a cream solid.

m/z: 250 (MH$^+$)

R$_f$: 0.29 (ethyl acetate:pentane; 1:2)

Preparation 77 tert-butyl 5-formyl-1,3-dihydro-2H-isoindole-2-carboxylate

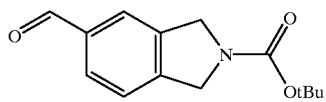

To a solution of the compound of Preparation 76 (4.76 g) in dry DMF (80 ml) was added sequentially sodium bicarbonate (4 g), 4-iodotoluene (4.2 g) and tetraethylammonium chloride (5.3 g). The solution was degassed three time, palladium (II) acetate (4.3 g) added and the mixture degassed a further two times. The very dark solution was heated at 100° C. under nitrogen for 20 hours. The cooled solution was partitioned between 2N HCl and ethyl acetate. The organics separated, washed with water (4×), dried (MgSO$_4$) and evaporated in vacuo. The residue was purified by column chromatography over silica gel using gradient elution (ethyl acetate:pentane; 4:1 to 1:1) to afford a brown solid. This solid was triturated with diisopropyl ether to afford the title compound as an off-white solid, 2.43 g.

$\delta_H$(400 MHz, CDCl$_3$): 10.00 (1H, s), 7.85–7.70 (2H, m), 7.46–7.35 (1H, m), 4.80 –4.70 (4H, m), 1.52 (9H, s).

Preparation 78 tert-butyl 5-[(R)-[(2S,5R)-4-benzyl-2,5-dimethylpiperazinyl](3-methoxyphenyl)methyl]-1,3-dihydro-2H-isoindole-2-carboxylate

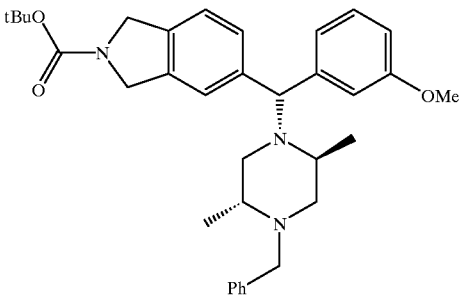

The compound of the above formula was prepared by a similar method to that described for Preparation 4 using the compound of Preparation 77 (mg), benzotriazole (409 mg). (–) -(2R, 5S)-1-benzyl-2,5-dimethylpiperazine (702 mg) and the Grignard reagent prepared from 3-bromoanisole (1.28 g).

Yield: 941 mg

R$_f$: 0.52 (diethyl ether:pentane; 1:1)

$\delta_H$ (400 MHz, CDCl$_3$): 7.40–7.05 (9H, m), 6.85–6.75 (3H, m), 5.04 (1H, br s), 4.62 (4H, m), 3.87 (1H, s), 3.77 (3H, s), 3.23 (1H, m), 2.75–2.55 (4H, m), 2.02 (2H, m), 1.50 (9H, s), 1.08 (6H, m).

$[\alpha]_D$ –6.2° (c=0.1, methanol)

Preparation 79

5-[(R)-[(2S,5R)-4-benzyl-2,5-dimethylpiperazinyl] (3-methoxyphenyl)methyl]isoindoline hydrochloride

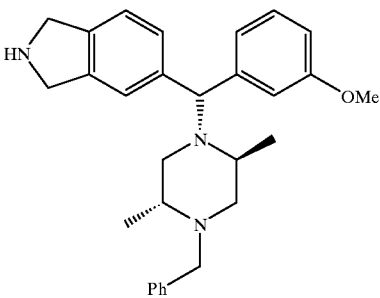

Hydrogen chloride was bubbled through an ice-cold solution of the compound of Preparation 78 (871 mg) and anisole (0.8 ml) in dichloromethane (40 ml) until saturation was achieved. The ice-cold solution was stirred for a further 30 minutes before being evaporated to dryness to afford a mixture of the title compound and anisole. 1.573 g as a cream solid. This material was used without further purification in subsequent reactions.

R$_f$: 0.42 (dichloromethane:methanol:ammonium hydroxide; 90:10:1)

m/z: 442 (MH$^+$)

Preparation 80 tert-butyl 3-(4-formylphenyl)-1-azetidinecarboxylate

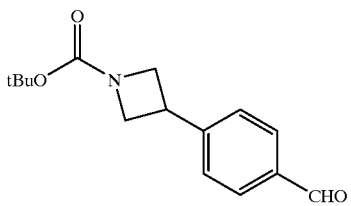

Zinc dust (253 mg) was stirred under nitrogen overnight. To this was added DMF (5 ml) and dibromomethane (55 mg) dissolved in DMF (1 ml) and the mixture warmed to ~70° C. The reaction mixture was cooled to room temperature and chlorotrimethylsilane (32 mg) in DMF (1 ml) added and stirred at room temperature for 15 minutes. To this was added 2-iodo-N-Boc-azetidine (Billotte, S., Synlett, 1998, 379–380) (1.04 g) in DMF (5 ml). The reaction mixture warmed to 40° C. and the mixture sonicated for 30 minutes during which time the zinc powder dissolved to leave a hazy solution. To the solution of zincate was added 4-iodobenzaldehyde (Preparation 43) (851 mg in 5 ml DMF), tri-2-furylphosphine (35 mg in 1 ml DMF) and Pd(dbq)$_2$ (42 ml in 1 ml DMF). The resulting mixture was heated at 60–70° C. for 4 hours, cooled to room temperature and partitioned between ammonium chloride solution and diethyl ether, and the aqueous layer was extracted with diethyl ether (3×). The combined organic extracts were dried (Na2SO4), evaporated in vacuo and purified over silica (pentane:ethyl acetate; 4:1) to afford the title compound as a mobile oil, 626 mg.

m/z: 262 (MH+)

R$_f$: 0.19 (pentane:ethyl acetate; 4:1)

Preparation 81 tert-butyl 3-{4-[(R)-[(2S,5R)-4-benzyl-2,5-dimethylpiperazinyl](3-methoxyphenyl)methyl]phenyl}-1-azetidinecarboxylate

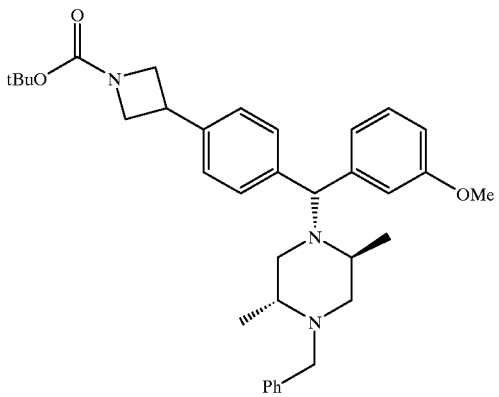

The compound of the above formula was prepared by a similar method to that described for Preparation 4 using the compound of Preparation 80 (610 mg), benzotriazole (278 mg), (–)-(2R, 5S)-1-benzyl-2,5-dimethylpiperazine (477 mg) and the Grignard reagent prepared from 3-bromoanisole (873 mg).

Yield: 925 mg m/z: 556 (MH$^+$)

R$_f$: 0.50 (pentane:isopropanol:ammonium hydroxide; 90:10:0.75)

Preparation 82

(2S,5R)-1-[(R)-[4-(3-azetidinyl)phenyl](3-methoxyphenyl)methyl]-4-benzyl-2,5-dimethylpiperazine

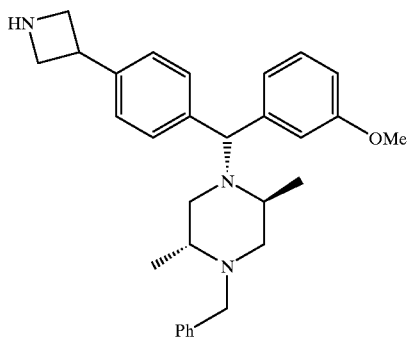

Excess trifluroacetic acid (12 ml) was added to an ice-cold solution of the compound of Preparation 81 (920 mg) in dry diethyl ether (35 ml ). The reaction was evaporated to dryness, dissolved in dichloromethane and washed with 2N sodium hydroxide solution. The organic layer was separated, dried (Na$_2$SO$_4$) and evaporated to dryness in vacuo to afford the title compound, 715 mg, which was used without further purification.

m/z: 456 (MH$^+$)

R$_f$ : 0.06 (pentane:isopropanol:ammonium hydroxide; 80:20:1.5)

δ$_H$ (400 MHz, CDCl$_3$): 7.39 (2H, d), 7.25 (2H, d), 6.80 (3H, m), 5.08 (1H, s), 4.00–3.77 (9H, m), 3.22 (1H, d), 2.65 (4H, m), 2.00 (2H, m), 1.75 (1H, br s), 1.09 (6H, d).

Preparation 83

7-Isoquinolinyl methyl ether

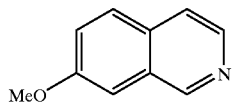

To a solution of BF$_3$.AcOH complex (33.78 g, 0.180 mol) in triflouoracetic anhydride (40 ml) at 0° C. was added a solution of the imine prepared from 3-methoxybenzaldehyde and aminoethanaldiethylacetal (Tetrahedron, 1971, 27, 1253) (15.06 g, 0.0599 mol) in trifluoroacetic anhydride (40 ml), maintaining the temperature below 10° C. After 48 hours, the mixture was poured into ice-water (300 ml), the solution made basic with concentrated ammonium hydroxide and extracted with dichloromethane. The organic phase was then extracted with aqueous hydrochloric acid solution (5N, 2×400 ml). The combined aqueous was made basic with concentrated ammonium hydroxide solution and extracted with dichloromethane. The organic phase was dried (MgSO$_4$), filtered, the solvent removed under reduced pressure and the residue purified on silica, eluting with a solvent gradient of 98:2 to 95:5 dichloromethane:methanol, to give the title compound, (6.85 g, 72%).

δ$_H$ (400 MHz, CDCl$_3$): 3.96 (3H, s), 7.22 (1H, s), 7.35 (1H, d), 7.58 (1H, d), 7.73 (1H, d), 8.42 (1H, d), 9.16 (1H, s).

Preparation 84

7-Isoquinolinol

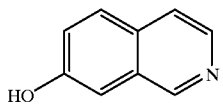

A solution of the compound of Preparation 83 (10.16 g, 0.0638 mol) in 48% hydrobromic acid (100 ml) was heated under reflux for 17 hours. The reaction was cooled to room temperature, diluted with water (150 ml) and the solution made neutral with saturated aqueous sodium bicarbonate solution. The cream precipitate formed was filtered under vacuum and dried to give the title compound. (5.95 g).

MS m/z 146 (MH)$^+$.

$^1$H-NMR (d$_6$-DMSO): δ=7.25 (1H, s), 7.32 (1H, d), 7.65 (1H, d), 7.80 (1H, d), 8.25 (1H, d), 9.07 (1H, s), 10.06 (1H, br).

Preparation 85

1,2,3,4-Tetrahydro-7-isoquinolinol

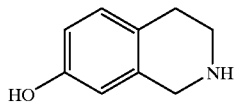

To a solution of the compound of Preparation 84 (10 g) in glacial acetic acid (100 ml) was added platinum oxide (0.5 g) and the mixture placed under an atmosphere of hydrogen at 40 p.s.i. for 16 hours. The crude mixture was filtered through a short pad of celite, eluting with ethanol and the filtrate evaporated under reduced pressure to give the title compound, (10.27 g), which was used without further purification.

$^1$H-NMR (CDCl$_3$): δ=2.90 (2H, s), 3.30 (2H, s), 4.01 (2H, s), 6.30 (1H, s), 6.65 (1H, d), 6.86 (1H, d).

Preparation 86 tert-Butyl 7-hydroxy-3,4-dihydro-2(1H) isoquinolinecarboxylate

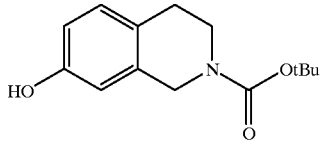

To a stirred solution of the compound of Preparation 85 (51.4 g) in water (200 ml) and tetrahydrofuran (500 ml) was added triethylamine (48 ml), followed by tert-butyldicarbonate (75.3 g). After 16 hours, the reaction mixture was concentrated under reduced pressure and extracted with ethyl acetate (×3). The combined organics were dried (MgSO$_4$), filtered and the solvent removed under reduced pressure to give the title compound, (78.55 g, 91%), which was used without further purification.

MS m/z 250 (MH)$^+$.

H-NMR (CDCl$_3$): δ=1.50 (9H, s), 2.74 (2H, t), 3.62 (2H, t), 4.52 (2H, s), 6.58–6.71 (2H, m), 6.98 (1H, d).

Preparation 87 tert-Butyl 7-{[(trifluoromethyl)sulphonyl]oxy}-3,4-dihydro-2(1H)-isoquinolinecarboxylate

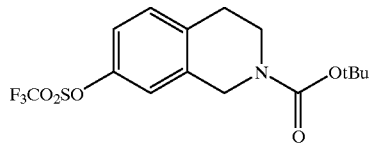

To a solution of the compound of Preparation 86 (3 g) in dichloromethane (50 ml) was added triethylamine (1.7 ml) and N-phenylbis(trifluoromethanesulponimide) (4.51 g) and the mixture stirred at room temperature for 48 hours. The mixture was evaporated to dryness under reduced pressure and the residue purified on silica gel eluting with a gradient of 85:15 to 5:1 hexane:ethyl acetate, to give the title compound (3.5 g, 76%).

MS m/z 382 (MH)$^+$.

$^1$H-NMR (CDCl$_3$): δ=1.50 (9H, s), 2.83 (2H, t), 3.65 (2H, t), 4.59 (2H, s), 7.00–7.10 (2H, m), 7.21 (1H, d).

Preparation 88 tert-Butyl 7-[(E)-3-ethoxy-3-oxo-1-propenyl]-3,4-dihydro-2(1H)-isoquinolinecarboxylate

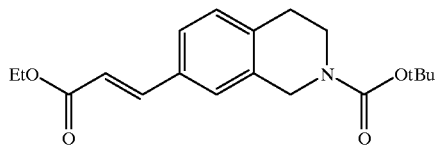

To a solution of the compound of Preparation 87 (22.6 g) in acetonitrile (250 ml) was added ethyl acrylate (8.35 ml), palladium acetate (0.8 g), tri-o-tolylphosphine (2.34 g) and triethylamine (16.5 ml). The solution was degassed and heated at reflux for 16 hours. The reaction was concentrated under reduced pressure and partitioned between ethyl acetate and saturated aqueous ammonium chloride solution. The aqueous phase was extracted with ethyl acetate and the combined organics dried (MgSO$_4$), filtered and the solvent removed under reduced pressure. The residue was purified on silica gel eluting with a solvent gradient of 1:9 to 1:3 ethyl acetate: hexane to give the title compound (8.56 g).

MS m/z 332 (MH)$^+$. $^1$H-NMR (CDCl$_3$): δ=1.33 (3H, t), 1.50 (9H, s), 2.84 (2H, t), 3.64 (2H, t), 4.25 (2H, q), 4.56 (2H, s), 6.40 (1H, d), 7.13 (1H, d), 7.25 (1H, s), 7.32 (1H, d), 7.62 (1H, d).

Preparation 89 tert-Butyl 7-(3-ethoxy-1,2-dihydroxy-3-oxopropyl)-3,4-dihydro-2(1H)-isoquinolinecarboxylate

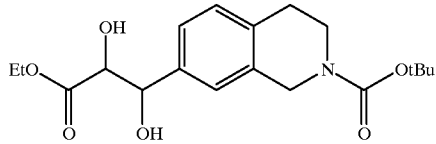

To a solution of the compound of Preparation 88 (14.43 g) in acetone (100 ml) and water (20 ml) was added N-methylmorpholine-N-oxide (7.65 g) followed by osmium tetroxide (4.7 ml, 2.5% wt solution). After 16 hours, the reaction was concentrated under reduced pressure and extracted with ethyl acetate. The organic phase was dried (MgSO$_4$), filtered and the solvent removed under reduced pressure. The residue was purified on silica gel eluting with a solvent gradient of 1:2 to 2:3 ethyl acetate: hexane to give the title compound (8.4 g).

MS m/z 383 (MNH$_4$)$^+$.

$^1$H-NMR (CDCl$_3$): δ=1.30 (3H, t), 1.48 (9H, s), 2.68 (1H, d), 2.82 (2H, t), 3.09 (1H, d), 3.62 (2H, t), 4.23–4.37 (3H, m), 4.58 (1H, s), 4.98 (1H, d), 7.10–7.22 (3H, m).

Preparation 90 tert-Butyl 7-formyl-3,4-dihydro-2(1H)-isoquinolinecarboxylate

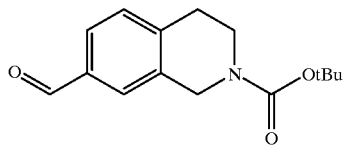

To a solution of the compound of Preparation 89 (5 g) in diethyl ether (200 ml) and water (150 ml) was added sodium periodate (5.85 g) and the reaction stirred at room temperature for 16 hours. The organic phase was separated and the aqueous phase extracted with ethyl acetate. The combined organics were dried (MgSO$_4$). filtered and the solvent removed under reduced pressure to give the title compound (3.52 g, 98%), which was used without further purification.

MS m/z 262 (MH)$^+$. $^1$H-NMR (CDCl$_3$): δ=1.47 (9H, s), 2.90 (2H, t), 3.66 (2H, t), 4.63 (2H, s), 7.29 (1H, d), 7.42 (1H, s), 7.47 (1H, d), 9.96 (1H, s).

Preparation 91 tert-Butyl 7-(R)-[(2S,5R)-4-benzyl-2,5-dimethylpiperazinyl](3-methoxyphenyl)methyl]-3,4-dihydro-2(1H)-isoquinolinecarboxylate

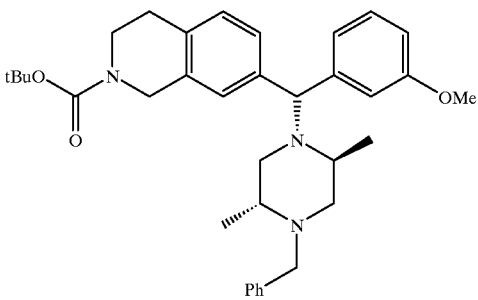

To a solution of the compound of Preparation 90 (3.5 g) in toluene (150 ml) was added (−)-(2R, 5S)-1-benzyl-2,5-dimethylpiperazine (2.74 g) and benzotriazole (1.6 g) and the reaction heated under Dean-Stark conditions for 3 hours. The reaction was cooled in an ice-water bath and a tetrahydrofuran solution of 2 equivalents of 3-methoxyphenylmagnesium bromide (prepared from 3-methoxybromobenzene and magnesium in tetrahydrofuran) added. The reaction was allowed to warm to room temperature and stirred for 90 minutes. Saturated aqueous ammonium chloride was added and the mixture extracted with ethyl acetate (×3). The combined organics were dried (MgSO$_4$), filtered and the solvent removed under reduced pressure to give the crude product which was purified on silica gel eluting with a solvent gradient of 1:4 to 1:1 ethyl acetate:hexane, to give the title compound (2.55 g).

MS m/z 556 (MH)$^+$.

$^1$H-NMR (CDCl$_3$): δ=1.10 (6H, m), 1.47 (9H, s), 1.96–2.05 (2H, m), 2.53–2.72 (4H. m), 2.79 (2H, t), 3.23 (1H, d), 3.62 (2H, t), 3.78 (3H, s), 3.86 (1H, d), 4.51 (2H, s), 5.00 (1H, s), 6.75–6.84 (3H, m), 7.03 (1H, d), 7.13–7.32 (8H, m).

Preparation 92

7-(R)-[(2S,5R)-4-benzyl-2,5-dimethylpiperazinyl](3-methoxyphenyl)methyl]-1,2,3,4-tetrahydroisoquinoline trihydrochloride

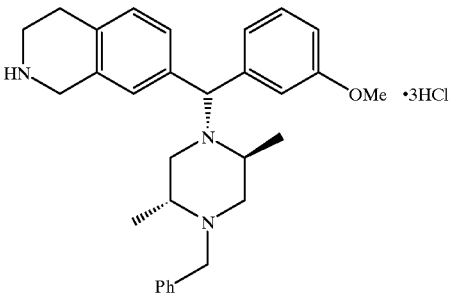

Into a solution of the compound of Preparation 91 (0.59 g) in dichloromethane (50 ml), cooled in an ice-water bath, was bubbled HCl gas. After 15 minutes, diethyl ether (50 ml) was added and the solvent removed under reduced pressure to give the title compound (0.587 g), which was used without further purification.

MS m/z 456 (MH)⁺.

$^1$H-NMR (d$_4$-MeOH): δ=1.25 (3H, br), 1.53 (3H, br), 3.06–3.34 (9H, m), 3.50 (2H, t), 3.80 (3H, s), 4.17 (1H, d), 4.36 (2H, s), 7.23–7.58 (12H, m).

Isolated Tissue Studies

Opioid activity was studied in isolated the mouse vas deferens (MVD) tissue. In this regard, MVD (DCI strain, Charles River, 25–35 g) were suspended in 15 ml organ baths containing Mg$^{++}$-free Krebs' buffer of the following composition (mM): NaCl, 119; KCl, 4.7; NaHCO$_3$, 25; KH$_2$PO$_4$, 1.2; CaCl$_2$, 2,5 and glucose, 11. The buffer was gassed with 95% O$_2$ and 5% CO$_2$. The tissues were suspended between platinum electrodes, attached to an isometric transducer with 500 mg tension and stimulated with 0.03 Hz pulses of 1-msec pulse-width at supramaximal voltage. IC$_{50}$ values were determined by the regression analysis of concentration-response curves for inhibition of electrically-induced contractions in the presence of 300 nM of the mu-selective antagonist CTOP. This test is a measure of δ agonism.

Each of the compounds according to the present invention that were tested had a pIC50 value of from 7 to 11.

Modifications will be apparent to those skilled in the art. What is claimed is:

1. A compound of the formula (I)

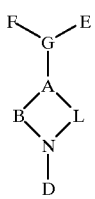

(1)

wherein:
A is N [or C-X]
G is C-Y
  wherein Y is H or C$_{1-4}$ alkyl;
B is ethylene optionally substituted;
L is ethylene optionally substituted;
further wherein:
  either D is H or C$_{1-10}$ hydrocarbyl group,
  or D is a C$_{1-10}$ hydrocarbyl group linked to B or L to form a second ring which includes the N of the first ring structure, which second ring structure is fused to the first ring structure and which second ring structure has from 5–7 atoms in the ring;
E is a phenyl group substituted by at least one or more of hydroxy, C$_{1-4}$ alkoxy or NH$_2$SO$_2$—C$_{1-4}$ alkylene;
F represents a combination of a phenyl group and a heterocyclic group, wherein
  (i) the heterocyclic group is not a tetrazole,
  (ii) the phenyl group is positioned in between G and the heterocyclic group,
  (iii) the phenyl group is linked directly to the heterocyclic group or is attached via a spacer group to the heterocyclic group, wherein the spacer group is any one of C$_{1-4}$ alkylene, carbonyl or SO$_2$, and
  (iv) the heterocyclic group is substituted by at least one or more of: a —COOH group, a bio-isostere of a —COOH group, a biolabile ester derivative of a —COOH group, a C$_{1-10}$ hydrocarbyl group comprising one or more —COOH groups, a C$_{1-10}$ hydrocarbyl group comprising one or more bio-isosteres of a —COOH group or a C$_{1-10}$ hydrocarbyl group comprising one or more biolabile ester derivatives of a —COOH group, or a pharmaceutically acceptable salt of the compound, or a pharmaceutically acceptable solvate of the compound of salt.

2. A compound, salt or solvate according to claim 1 wherein G is CH.

3. A compound, salt or solvate according to claim 1 wherein the hydrocarbyl group substituted on the heterocyclic group F and the hydrocarbyl group D are any one of an alkyl group, an alkenyl group, an alkynyl or an aryl group, including combinations thereof which groups may optionally contain one or more heteroatoms or groups, and may further comprise substituents on the chain or rings.

4. A compound, salt or solvate according to claim 1 wherein D is H, C$_1$–C$_6$ alkyl, C$_2$–C$_6$ alkenyl or aryl-(C$_1$–C$_4$) alkyl.

5. A compound, salt or solvate according to claim 4, wherein D is H, C$_1$–C$_3$ alkyl, C$_2$–C$_4$ alkenyl, or phenyl-(C$_1$–C$_3$) alkyl.

6. A compound, salt or solvate according to claim 1 wherein the heterocyclic group of group F is a heteroaromatic ring selected from the group consisting of thiazolyl, oxazolyl, oxadiazolyl, thiadiazolyl, pyridinyl, pyrimidinyl, pyrazolyl, triazoly, pyridazinyl, imidazolyl, furyl, thienyl, pyrrollyl, triazinyl, oxazinyl, isoxazinyl, oxathiazinyl, furanyl, thiophenyl, isoxazolyl and isothiazolyl.

7. A compound, salt or solvate according to claim 1 wherein the heterocyclic group of group F is a 4, 5 or 6 membered saturated or partially saturated heterocyclic ring selected from the group consisting of piperazinyl, azetidinyl, pyrollidinyl, piperizinyl and piperidinyl.

8. A compound, salt or solvate according to claim 1 wherein the heterocyclic group of group F is selected from the group consisting of tetrahydroquinolinyl, tetrahydroisoquinolinyl, indolinyl and isoindolinyl.

9. A compound, salt or solvate according to claim 1 wherein E is a phenyl group substituted with any one or more of OH, or C$_{1-4}$ alkoxy.

10. A compound, salt or solvate according to claim 1 wherein E is a phenyl group substituted with OH or methoxy.

11. A compound, salt or solvate according to claim 1 wherein the heterocyclic group is substituted with a —COOH group, a biolabile ester derivative of a —COOH group, a bio-isostere of a —COOH group, a C$_{1-6}$ alkyl hydrocarbyl group comprising a —COOH group, a C$_{1-6}$ alkyl hydrocarbyl group comprising a bio-isostere of a —COOH group, or a C$_{1-6}$ alkyl hydrocarbyl group comprising a biolabile ester derivative of a —COOH group.

12. A compound, salt or solvate according to claim 11 wherein the heterocyclic group is substituted with a —COOH group, a biolabile ester derivative of a —COOH group, a bio-isostere of a —COOH group; or a group of the formula R$^6$—(CH$_2$)$_m$—Z—(CH$_2$)$_n$— wherein m is 0, 1, 2 or 3, n is 0, 1, 2 or 3; Z is a direct link or O, NR$^a$ (where R$^a$ is H or C$_{1-6}$ alkyl, or other suitable group), S(0)$_p$ where p is 0, 1 or 2; and R$^6$ is —COOH or a biolabile ester derivative or —COOH, or a bio-isostere thereof.

13. A compound, salt or solvate according to claim 1 wherein the compound has the general formula (FIII)

(FIII)

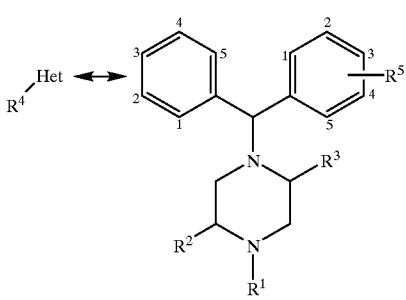

wherein
Het represents the heterocyclic group as recited in claim 1 such that the double arrow means that Het can be linked to the phenyl group;

$R^1$ is H, $C_2$–$C_6$ alkanoyl, $C_1$–$C_6$ alkyl, $C_2$–$C_6$ alkenyl, $C_2$–$C_6$ alkynyl, $C_3$–$C_7$ cycloalkyl, ($C_3$–$C_7$cycloalkyl)-($C_1$–$C_4$ alkyl), ($C_1$–$C_4$ alkoxy)-($C_1$–$C_4$ alkyl), carboxy-($C_1$–$C_4$ alkyl), aryl-($C_1$–$C_4$ alkyl) or heteroaryl-($C_1$–$C_4$ alkyl)

$R^2$ and $R^3$ are each independently H or $C_1$–$C_4$ alkyl;

or $R^1$ and $R^2$ may be taken together to represent $C_{1-6}$ alkylene;

$R^4$ is selected from
(i) —COOH or a bio-isostere thereof or a bio-labile ester derivative of a —COOH group;
(ii) a hydrocarbyl group comprising —COOH or a bio-isostere thereof or a bio-labile ester derivative of a —COOH group or a bio-isostere of a —COOH group, and (iii) a group of the formula

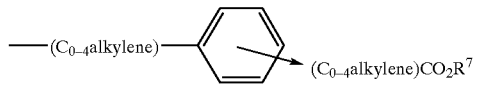

wherein the $C_{0-4}$ alkylene group may be optionally substituted or may be a carbonyl derivative thereof;
wherein $R^7$ is H or $C_1$–$C_4$ alkyl;
and $R^5$ is hydroxy, $C_1$–$C_4$ alkoxy or —NHSO$_2$($C_1$–$C_4$ alkyl), wherein $R^5$ can be attached to any one of positions 1, 2, 3, 4 and 5;
with the proviso that when Z is O, m is 1, 2 or 3 and independently n is 1, 2 or 3.

14. A pharmaceutical composition comprising a compound, salt or solvate according to claim 1 admixed with a pharmaceutically acceptable carrier, diluent or excipient.

15. A veterinary composition comprising a compound, salt or solvate according to claim 1 admixed with a veterinarily acceptable carrier, diluent or excipient.

16. A method for preventing or treating a disease or condition selected from the group consisting of arthritis, psoriasis, asthma, inflammatory bowel disease, disorders of respiratory function, gastro-intestinal disorders, functional bowel disease, functional GI disorders irritable bowel syndrome, functional diarrhea, functional distension, functional pain, non-ulcerogenic dyspepisa, disorders of motility or secretion, urogenital tract disorders, incontinence, pain, non-somatic pain, rejection in organ transplant and skin graft by administering to a mammal a therapeutically effective amount of a compound, salt or solvate of claim 1.

* * * * *